United States Patent
Missling et al.

(10) Patent No.: US 12,383,526 B2
(45) Date of Patent: *Aug. 12, 2025

(54) OPTIMIZED SIGMA-1 AGONIST METHOD OF RESPONDER SELECTION AND TREATMENT

(71) Applicant: ANAVEX LIFE SCIENCES CORP., New York, NY (US)

(72) Inventors: Christopher U. Missling, New York, NY (US); Mohammad Michel Afshar, Paris (FR); Frédéric Parmentier, Fresnes (FR)

(73) Assignee: ANAVEX LIFE SCIENCES CORP., New York, NY (US)

( * ) Notice: Subject to any disclaimer, the term of this patent is extended or adjusted under 35 U.S.C. 154(b) by 370 days.

This patent is subject to a terminal disclaimer.

(21) Appl. No.: 17/056,600

(22) PCT Filed: May 20, 2019

(86) PCT No.: PCT/US2019/033161
§ 371 (c)(1),
(2) Date: Nov. 18, 2020

(87) PCT Pub. No.: WO2019/222754
PCT Pub. Date: Nov. 21, 2019

(65) Prior Publication Data
US 2022/0226278 A1    Jul. 21, 2022

Related U.S. Application Data

(60) Provisional application No. 62/673,369, filed on May 18, 2018.

(51) Int. Cl.
| | | |
|---|---|---|
| *C12Q 1/6883* | (2018.01) | |
| *A61K 31/13* | (2006.01) | |
| *A61K 31/135* | (2006.01) | |
| *A61K 31/15* | (2006.01) | |
| *A61K 31/27* | (2006.01) | |
| *A61K 31/341* | (2006.01) | |
| *A61K 31/4045* | (2006.01) | |
| *A61K 31/438* | (2006.01) | |
| *A61K 31/439* | (2006.01) | |
| *A61K 31/445* | (2006.01) | |
| *A61K 31/485* | (2006.01) | |
| *A61K 31/495* | (2006.01) | |
| *A61K 31/5375* | (2006.01) | |
| *A61K 31/55* | (2006.01) | |
| *A61P 25/28* | (2006.01) | |

(52) U.S. Cl.
CPC ............ *A61K 31/341* (2013.01); *A61K 31/13* (2013.01); *A61K 31/135* (2013.01); *A61K 31/15* (2013.01); *A61K 31/27* (2013.01); *A61K 31/4045* (2013.01); *A61K 31/438* (2013.01); *A61K 31/439* (2013.01); *A61K 31/445* (2013.01); *A61K 31/485* (2013.01); *A61K 31/495* (2013.01); *A61K 31/5375* (2013.01); *A61K 31/55* (2013.01); *A61P 25/28* (2018.01); *C12Q 1/6883* (2013.01); *C12Q 2600/106* (2013.01); *C12Q 2600/156* (2013.01)

(58) Field of Classification Search
CPC ........ C12Q 2600/156; C12Q 2600/106; C12Q 1/6883; C12Q 2600/172; C12Q 16/6827; C12Q 2600/112; C12Q 2600/118; A61K 31/341; A61K 2300/00
See application file for complete search history.

(56) References Cited

U.S. PATENT DOCUMENTS

| | | | |
|---|---|---|---|
| 6,861,217 B1 * | 3/2005 | Liggett | C12Q 1/6883 536/23.5 |
| 2005/0250118 A1 | 11/2005 | Aerssens et al. | |
| 2010/0144781 A1 * | 6/2010 | Fu | A61K 31/4375 514/300 |
| 2011/0176993 A1 * | 7/2011 | Schneider | C12Q 1/6883 424/1.11 |
| 2016/0230227 A1 | 8/2016 | Sproul et al. | |

FOREIGN PATENT DOCUMENTS

| | | |
|---|---|---|
| CN | 101516401 A | 8/2009 |
| CN | 107072990 A | 8/2017 |
| JP | 2012500004 A | 1/2012 |
| JP | 2012531195 A | 12/2012 |
| WO | 2008095261 A1 | 8/2008 |
| WO | 2017013496 A1 | 1/2017 |

OTHER PUBLICATIONS

Takizawa et al., Association between sigma-1 receptor gene polymorphism and prefrontal hemodynamic response induced by cognitive activation in schizophrenia, Progress in Neuro-Psychopharmacology & Biological Psychiatry, vol. 33, pp. 491-498. (Year: 2009).*

Ohi et al., The SIGMAR1 gene is associated with a risk of schizophrenia and activation of the prefrontal cortex, Progress in Neuro-Psychopharmacology & Biological Psychiatry, vol. 35, pp. 1309-1315. (Year: 2011).*

Fehér et al. Association between a variant of the sigma-1 receptor gene and Alzheimer's disease, Neuroscience Letters, vol. 517, pp. 136-139. (Year: 2012).*

Lövkvist et al. Variations in apolipoprotein D and sigma non-opioid intracellular receptor 1 genes with relation to risk, severity and outcome of ischemic stroke, BMC Neurology, vol. 14:191, 10 pages. (Year: 2014).*

(Continued)

*Primary Examiner* — Dana H Shin
(74) *Attorney, Agent, or Firm* — Polsinelli PC

(57) ABSTRACT

The present disclosure provides genetic polymorphisms associated with an altered response of a subject to Sigma-1 receptor therapy. Also described is use of the polymorphisms to personalize treatment for subjects in need of Sigma-1 receptor therapy such as treatment of neurodevelopmental and neurodegenerative diseases and conditions.

8 Claims, 18 Drawing Sheets
(16 of 18 Drawing Sheet(s) Filed in Color)

(56) References Cited

OTHER PUBLICATIONS

Mandelli et al., The impact of a single nucleotide polymorphism in SIGMAR1 on depressive symptoms in major depressive disorder and bipolar disorder, Advances in Therapy, vol. 34, pp. 713-724. (Year: 2017).*
Kringel et al., Emergent biomarker derived from next-generation sequencing to identify pain patients requiring uncommonly high opioid doses, The Pharmacogenomics Journal, vol. 17, pp. 419-426. (Year: 2017).*
Michele G. Sullivan, Sigma 1 agonist presses forward after positive results in small Alzheimer's trial, Caring for the Ages, vol. 18, issue 3, pp. 28-29. (Year: 2017).*
Hajjar et al., Cross-sectional and longitudinal association between antihypertensive medications and cognitive impairment in an elderly population, Journal of Gerontology: Medical Sciences, vol. 60A, pp. 67-73. (Year: 2005).*
Ramon Cacabelos, Pharmacogenetic basis for therapeutic optimization in Alzheimer's disease, Molecular Diagnosis & Therapy, vol. 11, pp. 385-405. (Year: 2007).*
Weng et al., CHRNA7 polymorphisms and response to cholinesterase inhibitors in Alzheimer's disease, PLOS ONE, vol. 8, issue 12, e84059, pp. 1-8. (Year: 2013).*
Ishikawa et al., High occupancy of sigma1 receptors in the human brain after single oral administration of donepezil: a positron emission tomography study using [11C]SA4503, International Journal of Neuropsychopharmacology, vol. 12, pp. 1127-1131 (Year: 2009).*
Oslin et al., A functional polymorphism of the mu-opioid receptor gene is associated with naltrexone receptor in alcohol-dependent patients, Neuropsychopharmacology, vol. 28, pp. 1546-1552. (Year: 2003).*
International Search Report and Written Opinion issued Aug. 16, 2019 in corresponding International Patent Application No. PCT/US2019/033161.
Sullivan, "Development of a sigma 1 receptor agonist for Alzheimer's proceeds based on 2-year phase 2 data", Clinical Neurology News, Nov. 21, 2017.
Huang, et al., "Genetic Polymorphisms in Sigma-1 Receptor and Apolipoprotein E Interact to Influence the Severity of Alzheimer's Disease", Current Alzheimer Research, Nov. 2011.
Kishi T., et al., "Association Analysis of SIGMAR1 with Major Depressive Disorder and SSRI Response," Neuropharmacology, Feb. 12, 2010, vol. 58, pp. 1168-1173.
Office Action for Canadian Application No. 3, 100,897, mailed on Dec. 27, 2023, 10 pages.
Communication Pursuant to Article 94(3) EPC for Application No. 19802944.9, mailed on Sep. 20, 2023, 6 pages.
First Office Action and Search Report for Chinese Patent Application No. 201980045659.X, dated Apr. 25, 2023, 24 pages.
International Preliminary Report on Patentability for International Application No. PCT/US2019/033161, mailed Dec. 3, 2020, 9 pages.
Klimkowicz-Mrowiec A., et al., "Influence of rs1080985 Single Nucleotide Polymorphism of the CYP2D6 Gene on Response to Treatment with Donepezil in Patients with Alzheimer's Disease," Neuropsychiatric Disease and Treatment, 2013, vol. 9, pp. 1029-1033.
Notice of Reasons for Rejection for Japanese Application No. 2020-564752, mailed on Jun. 27, 2023, 5 pages.
Petit A-C., et al., "The Association of β-Arrestin2 Polymorphisms with Response to Antidepressant Treatment in Depressed Patients," Progress in Neuro-Psychopharmacology and Biological Psychiatry, 2018, vol. 81, pp. 74-79.
Ruscher K., et al., "The Involvement of the Sigma-1 Receptor in Neurodegeneration and Neurorestoration," Journal of Pharmacological Sciences, 2014, pp. 1-6.
Ruscher K., et al., "The Involvement of the Sigma-1 Receptor in Neurodegeneration and Neurorestoration," Journal of Pharmacological Sciences, 2015, vol. 127, pp. 30-35.
Sheikh H., et al., "Exome Sequencing in Bipolar Disorder with Comorbid Panic: Gene Set and Pathway Based-Analyses Suggest a Role for Glutamate and Calcium Signaling," European Neuropsychopharmacology, 2017, vol. 27, p. 19.
Office Action for Japanese Patent Application No. 2020-564752, mailed on Jul. 2, 2024, 3 pages.
Partial European Search Report for Application No. 25152481.5, dated May 8, 2025, 19 pages.
Examination Report for Australian Patent Application No. 2019269739, dated Mar. 12, 2025, 5 pages.
Eddings, Chelsy R., et al., "Pridopidine protects neurons from mutant-huntingtin toxicity via the sigma-1 receptor," Neurobiology of Disease, May 17, 2019, vol. 129, 21 pages.
Hampel, Harald, et al., "A precision medicine framework using artificial intelligence for the identification and confirmation of genomic biomarkers of response to an Alzheimer's disease therapy: Analysis of the blarcamesine (ANAVEX2-73) Phase 2a clinical study," Alzheimer's & Dementia: Translational Research & Clinical Interventions, Feb. 17, 2020, vol. 6, No. 1, 15 pages.
Jia, Jia, et al., "Sigma-1 Receptor-modulated Neuroinflammation in Neurological Diseases," Frontiers in Cellular Neuroscience, Sep. 20, 2018, vol. 12, 7 pages.
Ueda, N., et al., "Plasma Levels of Catecholamine Metabolites Predict the Response to Sulpiride or Fluvoxamine in Major Depression," Pharmacopsychiatry, Georg Thieme Verlag, Stuttgart, DE., vol. 35, No. 5, Sep. 1, 2002, pp. 175-181.
Yamagata, B., et al., "Preliminary use of insulin-like growth factor-I as a biomarker for sorting high-dose donepezil responders among Japanese patients with Alzheimer's disease," Regulatory Peptides, Elsevier Science BV, NL, vol. 163, No. 1-3, Aug. 9, 2010, pp. 137-142.

* cited by examiner

FIG. 10A

| A | | | | |
|---|---|---|---|---|
| ABCA7 | CNTN1 | IFNG | PDE4D | SNCA |
| ADAMTS9 | COMT | IL10 | PDE7A | SORL1 |
| AFF3 | CR1 | IL17A | PER1 | SRRM4 |
| AMT | CRY1 | IL18 | PER2 | ST3GAL3 |
| APOE | CRY2 | INPP5D | PER3 | SUOX |
| APP | CTNNBL1 | KANSL1 | PICALM | TCF4 |
| ARFGEF2 | DAG1 | KCNH1 | PLD3 | THRB |
| ARNT | DPYD | KMT2D | PPARG | TOMM40 |
| BCA7 | DSG2 | LARGE 1 | PSEN1 | TREM2 |
| BCHE | DTNBP1 | LRRK2 | PSEN2 | UBA7 |
| BCL11A | EPHA1 | MAPT | PTK2B | UBQLN1 |
| BDNF | ERCC8 | MDH1 | RAB10 | VSNL1 |
| BIN1 | FERMT2 | MEF2C | REST | ZCWPW1 |
| C12orf65 | FMR1 | MS4A4A | RIN3 | ZNF224 |
| CASS4 | FOXP1 | MS4A4E | RORA | |
| CD2AP | FRMD4A | MS4A6E | RORB | |
| CD33 | GBA | MTUS1 | RTN1 | |
| CELF1 | GCKR | NFIX | SHANK3 | |
| CHN1 | GMPPB | NME8 | SIGMAR1 | |
| CLN3 | GRIN2B | NPAS2 | SLC14A1 | |
| CLOCK | HLA-DRB1 | NR1D1 | SLC24A4 | |
| CLU | HLA-DRB4 | PCP4 | SNAP25 | |

FIG. 10B

| B | | | | |
|---|---|---|---|---|
| CYP1A1 | CYP2C58P | CYP2W1 | CYP4A26P | CYP4F35P | CYP7B1 |
| CYP1A2 | CYP2C59P | CYP20A1 | CYP4A27P | CYP4F36P | PTGIS |
| CYP1B1 | CYP2C60P | CYP21A1P | CYP4A43P | CYP4F44P | CYP8B1 |
| CYP1D1P | CYP2C61P | CYP21A2 | CYP4A44P | CYP4F45P | AS3MT |
| CYP11A1 | CYP2C63P | CYP24A1 | CYP4B1 | CYP4F59P | ASMT |
| CYP11B1 | CYP2C64P | CYP26A1 | CYP4F10P | CYP4F60P | COMT |
| CYP11B2 | CYP2C8 | CYP26B1 | CYP4F11 | CYP4F61P | GAMT |
| CYP17A1 | CYP2C9 | CYP26C1 | CYP4F12 | CYP4F62P | GNMT |
| CYP19A1 | CYP2D6 | CYP27A1 | CYP4F2 | CYP4F8 | HNMT |
| CYP2A13 | CYP2D7 | CYP27B1 | CYP4F22 | CYP4F9P | INMT |
| CYP2A6 | CYP2D8P | CYP27C1 | CYP4F23P | CYP4V2 | NNMT |
| CYP2A7 | CYP2E1 | CYP3A137P | CYP4F24P | CYP4X1 | PNMT |
| CYP2A7P1 | CYP2F1 | CYP3A4 | CYP4F25P | CYP4Z1 | TPMT |
| CYP2AB1P | CYP2F2P | CYP3A43 | CYP4F26P | CYP4Z2P | |
| CYP2AC1P | CYP2G1P | CYP3A5 | CYP4F27P | CYP46A1 | |
| CYP2B6 | CYP2G2P | CYP3A51P | CYP4F29P | CYP46A4P | |
| CYP2B7P | CYP2J2 | CYP3A52P | CYP4F3 | TBXAS1 | |
| CYP2C115P | CYP2R1 | CYP3A54P | CYP4F30P | CYP51A1 | |
| CYP2C18 | CYP2S1 | CYP3A7 | CYP4F31P | CYP51A1P1 | |
| CYP2C19 | CYP2T1P | CYP39A1 | CYP4F32P | CYP51A1P2 | |
| CYP2C23P | CYP2T3P | CYP4A11 | CYP4F33P | CYP51A1P3 | |
| CYP2C56P | CYP2U1 | CYP4A22 | CYP4F34P | CYP7A1 | |

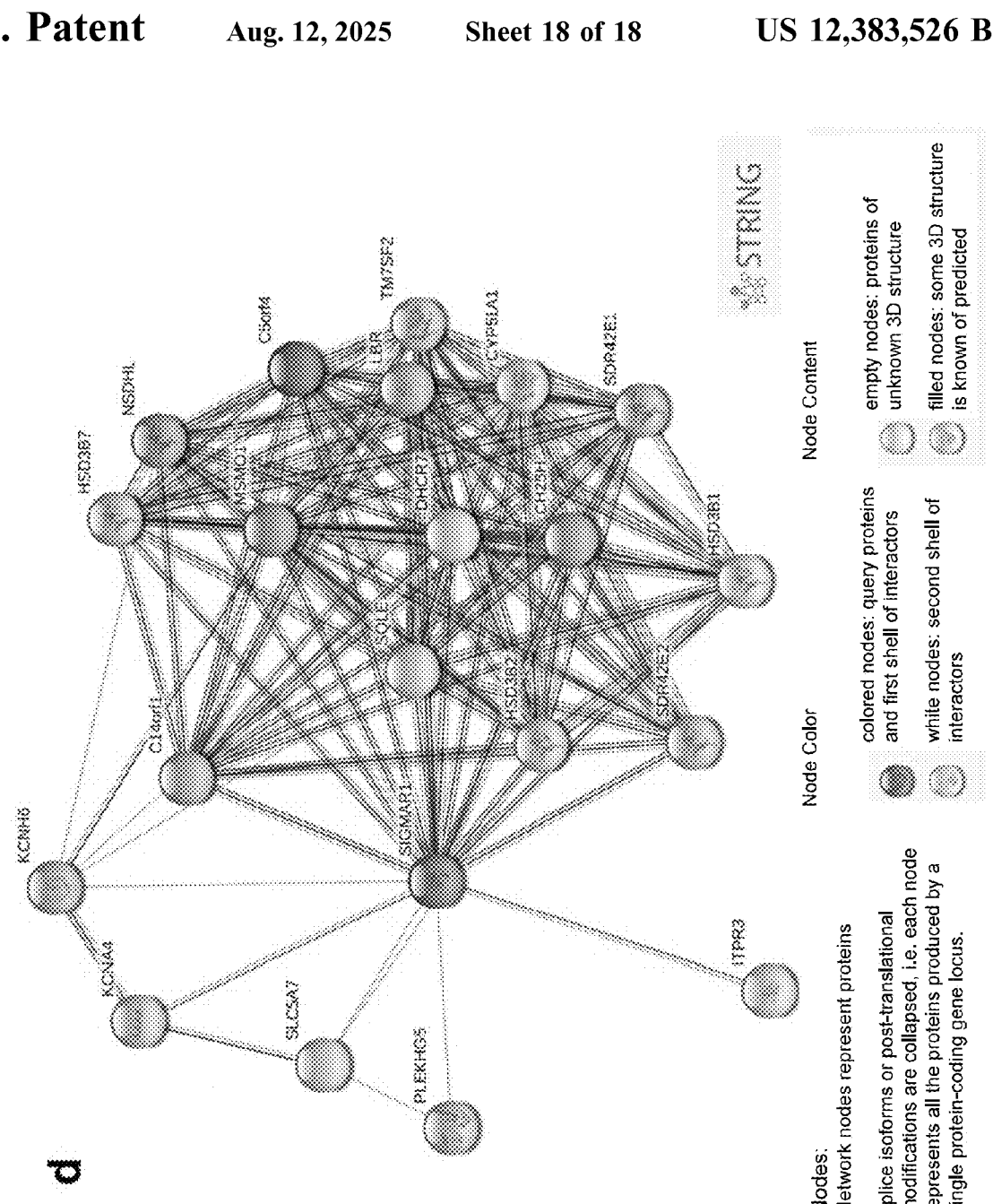

OPTIMIZED SIGMA-1 AGONIST METHOD OF RESPONDER SELECTION AND TREATMENT

CROSS-REFERENCE TO RELATED APPLICATIONS

This application is the 35 U.S.C. 371 National Stage of International Application Number PCT/US2019/033161, filed May 20, 2019, which claims the benefit of U.S. Provisional Patent Application No. 62/673,369, filed May 18, 2018, the entire disclosure of both of which is incorporated herein by reference.

FIELD OF THE INVENTION

The present invention relates generally to methods of determining if a subject is responsive or non-responsive to Sigma-1 receptor agonist therapy.

BACKGROUND OF THE INVENTION

Alzheimer's disease (AD) is a progressive neurodegenerative disorder characterized by loss of memory and other cognitive functions, leading to interference in daily life activities. At present, there is a dearth of pharmacological treatments that have been shown to alter progression of the disease. Sigma-1 receptor (SIGMAR1), a modulator of calcium homeostasis and mitochondrial function, is a new target relevant to conditions variously known as neurodegenerative and neurodevelopmental disorders or indications, including AD. SIGMAR1 activation has been shown to reduce key pathophysiological processes in AD including hyperphosphorylation of tau, neuroprotection, neurodegeneration, and oxidative stress. Activation of SIGMAR1 also leads to increase in autophagic flux in human cells and in vivo. However, genetic heterogeneity of the AD patient population and lack of objective efficacy measures or predictive biomarkers of response to treatment contribute to severe limitations in treatment efficacy. This heterogeneity is a background noise that can obscure successful treatments.

Therefore, there is a need for predictive biomarkers and methods for developing personalized protocols for treating patients in need of Sigma-1 receptor therapy.

SUMMARY OF THE INVENTION

One aspect of the present disclosure encompasses a method of selecting a subject responsive to Sigma-1 receptor agonist therapy. The method comprises obtaining or having obtained the results of a test of a biological sample from the subject which determines the presence of at least one polymorphism selected from the group consisting of SIGMAR1_Q2P, COMT_L146fs, KANSL1_P1010L/P304L/P946L, DHCR7_M220T, HLA-DRB1_A244T, HLA-DRB1_S66Y, HLA-DRB1_Y89S, MS4A6E_M59T, RIN3_H215R, DPYD_1543V, and combinations thereof in the subject. The method further comprises excluding the subject as non-responsive to Sigma-1 receptor agonist therapy if a polymorphism is present in the subject.

Another aspect of the present disclosure encompasses a method of selecting subjects responsive to Sigma-1 receptor agonist therapy. The method comprises detecting or having detected if at least one polymorphism is present at a genetic locus in a biological sample obtained from the subject by sequencing the genetic locus comprising the polymorphism. The method further comprises excluding the subject as non-responsive to Sigma-1 receptor agonist therapy if a polymorphism is present in the subject the subject. The at least one polymorphism is selected from the group consisting of SIGMAR1_Q2P, COMT_L146fs, KANSL1_P1010L/P304L/P946L, DHCR7_M220T, HLA-DRB1_A244T, HLA-DRB1_S66Y, HLA-DRB1_Y89S, MS4A6E_M59T, RIN3_H215R, DPYD_1543V, and combinations thereof.

Yet another aspect of the present disclosure encompasses a method of selecting subjects responsive to Sigma-1 receptor agonist therapy. The method comprises obtaining or having obtained the results of a test of a biological sample from the subject which determines the level of expression of RNA encoded by at least gene selected from the group consisting of SIGMAR1, COMT, KANSL1, DHCR7, HLA-DRB1, MS4A6E, RIN3, DPYD, and combinations thereof, and comparing the level of the RNA in the test sample to the level of the RNA in a subject responsive to Sigma-1 receptor therapy. A level of the RNA in the test sample substantially similar to the level of the RNA in the subject responsive to Sigma-1 receptor therapy identifies a subject responsive to Sigma-1 receptor therapy.

Another aspect of the present disclosure encompasses a method of selecting subjects responsive to Sigma-1 receptor agonist therapy. The method comprises determining or having determined the level of expression of RNA encoded by at least gene selected from the group consisting of SIGMAR1, COMT, KANSL1, DHCR7, HLA-DRB1, MS4A6E, RIN3, DPYD, and combinations thereof. The method also comprises excluding the subject as non-responsive to Sigma-1 receptor agonist therapy if the level of the RNA in the test sample is substantially different from the level of the RNA in a subject responsive to Sigma-1 receptor therapy.

One aspect of the present disclosure encompasses a method of treating a subject in need of Sigma-1 receptor agonist therapy. The method comprises obtaining or having obtained the results of a test of a biological sample from the subject which detects the presence of at least one polymorphism selected from the group consisting of SIGMAR1_Q2P, COMT_L146fs, KANSL1_P1010L/P304L/P946L, DHCR7_M220T, HLA-DRB1_A244T, HLA-DRB1_S66Y, HLA-DRB1_Y89S, MS4A6E_M59T, RIN3_H215R, DPYD_1543V, and combinations thereof in the subject. The method also comprises administering a therapeutically effective amount of a Sigma-1 receptor agonist to the subject if a polymorphism is not present in the subject.

Another aspect of the present disclosure encompasses a method of treating a subject in need of Sigma-1 receptor agonist therapy. The method comprises, obtaining or having obtained the results of a test of a biological sample from the subject which determines the level of expression of RNA encoded by at least gene selected from the group consisting of SIGMAR1, COMT, KANSL1, DHCR7, HLA-DRB1, MS4A6E, RIN3, DPYD, and combinations thereof. The method further comprises comparing the level of the RNA in the test sample to the level of the RNA in a subject responsive to Sigma-1 receptor therapy, and administering a therapeutically effective amount of a Sigma-1 receptor agonist to the subject if a level of the RNA in the test sample is substantially similar to the level of the RNA in a subject responsive to Sigma-1 receptor therapy.

Yet another aspect of the present disclosure encompasses a method of detecting the presence of a polymorphism associated with response to Sigma-1 receptor therapy in a subject. The method comprises obtaining or having obtained a biological sample from the subject, and detecting the polymorphism in the biological sample by evaluating the sequence of a genetic locus comprising the polymorphism. The at least one polymorphism is selected from the group consisting of SIGMAR1_Q2P, COMT_L146fs, KANSL1_P1010L/P304L/P946L, DHCR7_M220T, HLA-DRB1_A244T, HLA-DRB1_S66Y, HLA-DRB1_Y89S, MS4A6E_M59T, RIN3_H215R, DPYD_1543V, and combinations thereof in the subject.

REFERENCE TO COLOR FIGURES

The application file contains at least one drawing executed in color. Copies of this patent application publication with color drawings will be provided by the Office upon request and payment of the necessary fee.

BRIEF DESCRIPTION OF THE FIGURES

FIG. 1 is an illustrative overview of study design, data availability and analytical methods.

FIG. 2A: Dose administration cross-over design including eight possible administration schemes, where a single dose regime is given in each period (Intravenous (IV) or Orally (Oral)), either beginning with an IV or Oral administration with two possible doses allocated randomly. FIG. 2B: Pharmacokinetics parameter area under curve between 0 and infinity (AUC0-inf) of ANAVEX2-73 after first administration (24h first hours of the trial) in 57-week study Part A with different randomized administration dosages. FIG. 2C: Boxplot of mean concentration groups of ANAVEX2-73 in the plasma.

FIG. 4A: MMRM-LME-adjusted slopes for the high concentration (Green) cohort versus low and medium concentration patient cohort (Magenta) with time (in weeks) against adjusted Delta MMSE. Average adjusted values with residuals at the population level were plotted at each time point (dotted line). FIG. 4B: MMRM-LME-adjusted slopes for the high concentration (Green) cohort versus low and medium concentration patient cohort (Magenta) with time (in weeks) against adjusted Delta MMSE. Average adjusted values with residuals at the population level were plotted at each time point (dotted line).

FIG. 8A: Plot showing that the frameshift COMT Leu146 mutation is strongly linked to a high ADCS-ADL Delta from baseline (BL). FIG. 8B: Plot showing that the absence of KANSL1 Pro304/946/1010 mutation is strongly linked to a high ADCS-ADL Delta from BL. FIG. 8C: Plot showing that the absence of SIGMAR1 Pro2 mutation is strongly linked to a high ADCS-ADL Delta from BL. FIG. 8D: Plot showing that the absence of frameshift COMT Leu146 mutation is strongly linked to a high MMSE delta from BL. FIG. 8E: Plot showing that the absence of KANSL1 Pro304/946/1010 mutation is strongly linked to a high MMSE delta from BL.

FIG. 8F: Plot showing that the absence of SIGMAR1 Pro2 mutation is strongly linked to a high MMSE delta from BL.

FIGS. 10A-10D provide the 243 genes selected from the 27,155 mapped sequences obtained from NGS analysis (shown in FIGS. 10A-10C). FIG. 10A lists the 102 genes selected on the basis of their involvement in neurodegenerative diseases. FIG. 10B provides the added 113 genes of the cytochrome P450s gene family and 10 genes from the methyltransferase gene family. FIGS. 10C-10D shows the 20 genes selected as part of a SIGMAR1's functional interactome, based on a confidence score of 0.150 obtained from the STRING database (January 2018).

DETAILED DESCRIPTION

Figure 1A:
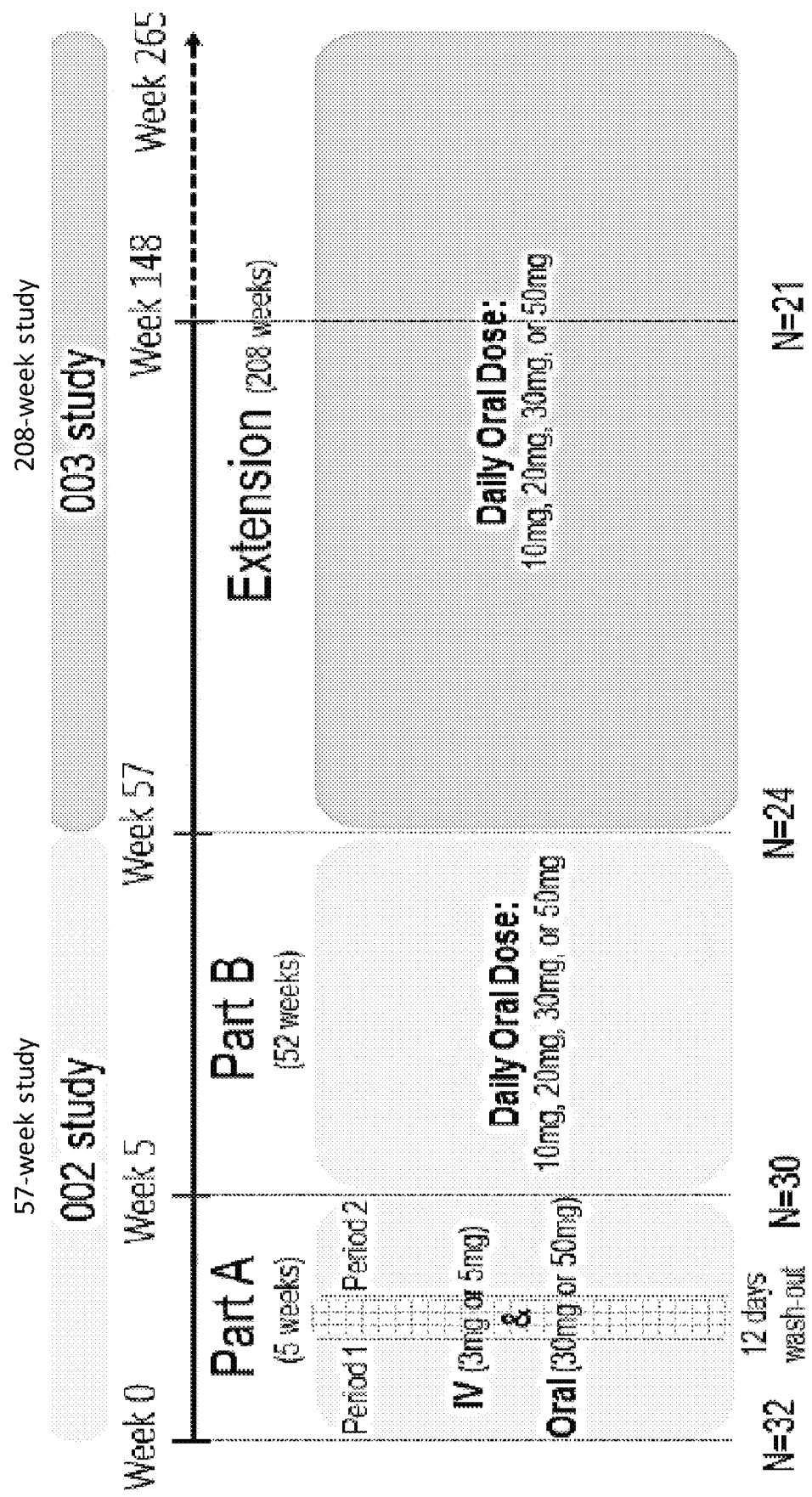
FIG. 1A: Summary of consecutive clinical trials involving two parts: Part A over 5 weeks and Part B over 52 weeks (57-week study), and 208-week study extension study over a planned 208 week period following immediately after the initial trial, totaling in a cumulative 265-weeks.

The present disclosure is based in part on the discovery of methods of determining if a subject is responsive or non-responsive to Sigma-1 receptor therapy. The methods can comprise detecting the presence of a polymorphism associated with an altered response to Sigma-1 receptor therapy. The method can also comprise determining the level of expression of RNA encoded by a gene associated with an altered response to Sigma-1 receptor therapy. The methods can be used to optimize treatment for subjects in need of Sigma-1 receptor therapy. Based on the predicted responsiveness of a subject to the therapy, personalized treatment can be provided to each subject. For instance, responsive subjects can be selected for treatment using a Sigma-1 receptor agonist, whereas non-responsive subjects may be provided alternative, more appropriate treatment regimens early in the disease development process and/or even before treatment is started. This is in contrast to current methods wherein a subject is determined to be responsive or non-responsive after an extended period of treatment. The polymorphisms, methods of identifying the polymorphisms, and methods of using the polymorphisms are described below.

I. Polymorphisms Associated with Response of a Subject to Sigma-1 Receptor Therapy One aspect of the present invention encompasses genetic polymorphisms predictive of reduced therapeutic response to treatment using Sigma-1 receptor therapy. Polymorphisms of interest can be at any genetic locus in the genome in a subject provided the polymorphism is associated with a positive response of a subject to Sigma-1 receptor therapy. For instance, the polymorphism can be in a coding region or noncoding region of the genome of the subject, including mitochondrial DNA. The polymorphism can result from an insertion, a deletion, or a single nucleotide polymorphism (SNP) in a gene or genetic locus.

In some aspects, the polymorphism associated with response to Sigma-1 receptor therapy is in a gene selected from SIGMAR1, COMT, KANSL1, DHCR7, HLA-DRB1, MS4A6E, RIN3, GAMT, IL10, MTUS1, PPARG, and combinations thereof. In one aspect, the polymorphism is in a gene selected from SIGMAR1, COMT, KANSL1, DHCR7, HLA-DRB1, MS4A6E, RIN3, and combinations thereof. In another aspect, the polymorphism is in a gene selected from SIGMAR1, COMT, KANSL1, and combinations thereof.

In some aspects, the polymorphism associated with response to Sigma-1 receptor therapy is selected from the group consisting of SIGMAR1_Q2P, COMT_L146fs, COMT_L146fs, KANSL1_P1010L/P304L/P946L, DHCR7_M220T, HLA-DRB1_A244T, HLA-DRB1_S66Y, HLA-DRB1_Y89S, MS4A6E_M59T, RIN3_H215R, DPYD_I543V, or combinations thereof. Table 1 details these polymorphisms.

TABLE 1

Polymorphisms Highly Associated with Substance Dependence

| SNP number | Polymorphism | Gene | Description |
| --- | --- | --- | --- |
| rs1800866 | SIGMAR1_Q2P | SIGMAR1 | Replaces Q2 with P |
| rs113895332 | COMT_L146fs | COMT | Stop after L146 |
| rs61143203 | COMT_L146fs | COMT | Stop after L146 |
| rs115755772 | KANSL1_P1010L/P304L/P946L | KANSL1 | Replaces P1010 with L, P304 with L, and P946 with L |
| rs760241 | DHCR7_M220T | DHCR7 | Replaces M220 with T |
|  | HLA-DRB1_A244T | HLA-DRB1 | Replaces A244 with T |
|  | HLA-DRB1_S66Y | HLA-DRB1 | Replaces S66 with Y |
| rs1059586 | HLA-DRB1_Y89S | HLA-DRB1 | Replaces Y89 with S |
| rs12798157 | MS4A6E_M59T | MS4A6E | Replaces M59 with T |
| rs3829947 | RIN3_H215R | RIN3 | Replaces H215 with R |
| re1801159 | DPYD_I543V | DPYD | Replaces I543 with V |

In one aspect, the polymorphism associated with response to Sigma-1 receptor therapy is selected from the group consisting of SIGMAR1_Q2P, COMT_L146fs (rs113895332/rs61143203), KANSL1_P1010L/P304L/P946L, and combinations thereof. In another aspect, the polymorphism associated with response to Sigma-1 receptor therapy is selected from the group consisting of SIGMAR1_Q2P, COMT_L146fs (rs113895332 or rs61143203), KANSL1_P1010L/P304L/P946L, and combinations thereof. In yet another aspect, the polymorphism associated with response to Sigma-1 receptor therapy is SIGMAR1_Q2P. In one aspect, the polymorphism associated with response to Sigma-1 receptor therapy is COMT_L146fs (rs113895332 or rs61143203). In another aspect, the polymorphism associated with response to Sigma-1 receptor therapy is KANSL1_P1010L/P304L/P946L.

II. Method of Determining the Responsiveness of a Subject to Sigma-1 Receptor Therapy Another aspect of the present invention provides methods of determining if a subject is responsive or non-responsive to Sigma-1 receptor therapy. The method can comprise detecting the presence of a polymorphism associated with an altered response to Sigma-1 receptor therapy. The method can also comprise determining the level of expression of RNA encoded by at least one gene associated with an altered response to Sigma-1 receptor therapy.

In one aspect, the method comprises detecting the presence of at least one polymorphism associated with an altered response to Sigma-1 receptor therapy. The presence of at least one polymorphism identifies a subject responsive to Sigma-1 receptor therapy. The polymorphisms and the genes comprising the polymorphisms are as described in Section I.

The presence of one or more than one polymorphism can be detected. For instance, the presence of 1, 2, 3, 4, 5, 6, 7, 8, 9, 10, or more polymorphisms can be detected. In some aspects, the presence of 1, 2, 3, 4, 5, 6, 7, 8, 9, or 10 polymorphisms can be detected. In other aspects, the presence of 1, 2, 3, 4, or 5 polymorphisms can be detected. In yet other aspects, the presence of 1, 2, or 3 polymorphisms can be detected.

The presence or absence of polymorphisms can be detected by evaluating nucleic acid sequences in the subject. Alternatively, the presence or absence of polymorphisms can be detected by evaluating the expression of a nucleic acid or protein from a gene or genetic locus comprising the polymorphism.

In some aspects, the presence or absence of polymorphisms can be detected by evaluating nucleic acid sequences for the presence of a polymorphism at the locus comprising the polymorphism. The nucleic acid sequence can be a DNA or an RNA sequence expressed from a genetic locus comprising the polymorphism. Methods suitable for detecting the polymorphism are well known in the art. For instance, the methods include shotgun sequencing, bridge PCR, high throughput methods, allele-specific real time PCR, 5'-nuclease assays, template-directed dye-terminator incorporation, molecular beacon allele-specific oligonucleotide assays, assays employing invasive cleavage with Flap nucleases, allele-specific hybridization (ASH), array based hybridization, allele-specific ligation, primer extension, single-base extension (SBE) assays, sequencing, pyrophosphate sequencing, real-time pyrophosphate sequencing, sequence length polymorphism analysis, restriction length fragment polymorphisms (RFLP), RFLP-PCR, single-stranded conformational polymorphism (SSCP), PCR-SSCP, fragment sizing capillary electrophoresis, heteroduplex analysis, and mass array systems. Analysis of amplified sequences may be performed using various technologies such as microchips, fluorescence polarization assays, and matrix-assisted laser desorption ionization (MALDI) mass spectrometry. High throughput sequencing methods include massively parallel signature sequencing (MPSS), polony sequencing, 454 pyrosequencing, illumina (Solexa) sequencing, combinatorial probe anchor synthesis (cPAS), SOLiD sequencing, ion Torrent semiconductor sequencing, DNA nanoball sequencing, heliscope single molecule sequencing, single molecule real time (SMRT) sequencing, nanopore DNA sequencing, tunneling currents DNA sequencing, sequencing by hybridization, sequencing with mass spectrometry, microfluidic Sanger sequencing, microscopy-based techniques, RNAP sequencing, and in vitro virus high-throughput sequencing.

In another aspect, the method comprises determining the level of expression of RNA encoded by at least one gene associated with an altered response to Sigma-1 receptor therapy. According to the method, a level of the RNA substantially similar to the level of the RNA in the subject responsive to Sigma-1 receptor therapy identifies a subject responsive to Sigma-1 receptor therapy. The genes associated with an altered response to Sigma-1 receptor therapy are selected from the group consisting of SIGMAR1, COMT, KANSL1, DHCR7, HLA-DRB1, MS4A6E, RIN3, DPYD, and combinations thereof.

For instance, the level of expression of RNA encoded by 1, 2, 3, 4, 5, 6, 7, 8, 9, 10, or more genes can be detected. In some aspects, the level of expression of RNA encoded by 1, 2, 3, 4, 5, 6, 7, 8, 9, or 10 genes can be detected. In other aspects, the level of expression of RNA encoded by 1, 2, 3, 4, or 5 genes can be detected. In yet other aspects, the level of expression of RNA encoded by of 1, 2, or 3 genes can be detected.

Measuring the level of RNA expression may be accomplished by a variety of methods including northern blotting, quantitative real-time PCR (qRT-PCR), nucleic acid microarrays, Luminex microspheres, and nuclease protection assay. Methods of determining a substantially different level of RNA expression are known in the art, and include distribution analysis. In some aspects, a substantially different level of RNA expression is determined by normalizing RNA expression values as Transcripts Per Kilobase Million (TPM).

In other aspects, determining if a subject is responsive or non-responsive to Sigma-1 receptor therapy can be detected by measuring the level of a protein expressed from a gene comprising the polymorphism. Methods of measuring protein expression include a variety of methods such as high-performance liquid chromatography (HPLC), liquid chromatography-mass spectrometry (LC/MS), enzyme-linked immunosorbent assay (ELISA), protein immunoprecipitation, immunoelectrophoresis, western blotting, and protein immunostaining.

Determining if a subject is responsive or non-responsive to Sigma-1 receptor therapy can be detected in the subject in vivo or in vitro. Typically, responsiveness of a subject to Sigma-1 receptor therapy can be by analyzing a nucleic acid or protein in vitro in a biological sample obtained from the subject. The nucleic acid or protein can be isolated from the biological sample using methods commonly known in the art. For more information, see Ausubel et al., 2003, or Sambrook & Russell, 2001. Commercially available nucleic acid and protein extraction kits or commercially available extraction reagents may be used to isolate the nucleic acid from the biological sample.

Non-limiting examples of suitable biological samples include fluid samples, biopsy samples, skin samples, and hair samples. Fluid samples may include blood, serum, saliva, tears, and lymph. In some aspects the biological sample is blood. Methods of collecting a biological sample from a subject are well known in the art.

In some aspects the method of determining if a subject is responsive or non-responsive to Sigma-1 receptor therapy comprises obtaining the results of a test of a biological sample from the subject which determines the presence of at least one polymorphism. In other aspects, the method of determining responsiveness of a subject to Sigma-1 receptor therapy comprises detecting if at least one polymorphism is present at a genetic locus in a biological sample obtained from the subject by sequencing the genetic locus comprising the polymorphism. In yet other aspects, the method of determining if a subject is responsive or non-responsive to Sigma-1 receptor therapy comprises obtaining the results of a test of a biological sample from the subject which determines the level of at least one RNA encoded by a gene associated with an altered response to Sigma-1 receptor therapy. In other aspects, the method of determining responsiveness of a subject to Sigma-1 receptor therapy comprises detecting if at least one polymorphism is present at a genetic locus in a biological sample obtained from the subject by determining the level of expression of at least one RNA encoded by a gene associated with an altered response to Sigma-1 receptor therapy.

III. Methods of Using

The methods can be used to optimize treatment for subjects in need of Sigma-1 receptor agonist therapy. For instance, the methods can be used to select a subject responsive to Sigma-1 receptor therapy prior to initiating a treatment protocol for the subject. Conversely, the methods can be used to exclude, prior to treatment, a subject if the subject is found to be non-responsive to Sigma-1 receptor therapy. Polymorphisms can be used to determine, prior to treatment, if a subject will develop toxicity if treated with a Sigma-1 receptor agonist. Additionally, the methods can be used to determine if or when a treatment with a Sigma-1 receptor agonist should be discontinued in a subject. Additionally, the methods can be used in evaluating the response of a subject to a substance cessation treatment.

The methods comprise detecting the presence of a polymorphism in a subject, and determining if a subject is a candidate for Sigma-1 receptor therapy. The methods can also comprise determining the level of expression of RNA from one or more genes associated with an altered response to Sigma-1 receptor therapy. The polymorphisms, the genes associated with an altered response to Sigma-1 receptor therapy, the methods of detecting the polymorphisms, and the methods of determining the level of RNA expression can be as described in Section I, and methods of detecting the polymorphisms can be as described in Section II.

As used herein, the term "responsive" can be used to describe any subject that experiences a positive outcome when treated with a Sigma-1 receptor agonist. Methods of determining responsiveness of a subject to Sigma-1 receptor therapy can and will vary depending on the condition or disease, the subject, the treatment protocol, among other variables, and can be determined experimentally. Responsiveness can be as determined at any time point considered appropriate by an individual of skill in the art for a disease or condition. For instance, treatment outcome can be determined at about 57 weeks, about 148 weeks, or about 208 weeks after initiation of treatment.

When treatment is used for Alzheimer's disease (AD), positive outcomes can be as measured by Delta or Slope MMSE (Mini-Mental State Examination) or ADCS-ADL (Alzheimer's Disease Cooperative Study—Activities of Daily Living). Responsive subjects are characterized by having a positive or null MMSE and/or ADCS-ASL slope, whereas non-responsive subjects are characterized by having a negative MMSE and/or ADCS-ASL slope. Responsive subjects are also characterized by having a high MMSE and/or ADCS-ASL delta, whereas non-responsive subjects are characterized by having a low MMSE and/or ADCS-ASL delta. A low MMSE delta may range from about −9 to about −6, from about −6 to about −2, or from about −9 to about −2, whereas a hish MMSE delta may range from about −6 to −2 or from about −2 to about 6. Methods of determining Delta or Slope MMSE or ADCS-ADL can be as described in the examples herein.

In some aspects, the method is used to select a subject responsive to Sigma-1 receptor agonist therapy. The method comprises obtaining the results of a test of a biological sample from the subject which determines the presence of at least one polymorphism, and excluding the subject as non-responsive to Sigma-1 receptor agonist therapy if a polymorphism is present in the subject. Alternatively, a subject can be included as responsive to the therapy if a polymorphism is not present in the subject. In one aspect, the polymorphism is selected from the group consisting of SIGMAR1_Q2P, COMT_L146fs, KANSL1_P1010L/P304L/P946L, DHCR7_M220T, HLA-DRB1_A244T, HLA-DRB1_S66Y, HLA-DRB1_Y89S, MS4A6E_M59T, RIN3_H215R, DPYD_1543V, and combinations thereof. In another aspect, the polymorphism is selected from the group consisting of SIGMAR1_Q2P, COMT_L146fs, COMT_L146fs, KANSL1_P1010L/P304L/P946L, and combinations thereof. The presence of the polymorphism can be obtained by evaluating nucleic acid sequences.

In other aspects, the method is used to select a subject responsive to Sigma-1 receptor agonist therapy. The method comprises detecting if at least one polymorphism is present at a genetic locus in a biological sample obtained from the subject by sequencing the genetic locus comprising the polymorphism, and excluding the subject as non-responsive to Sigma-1 receptor agonist therapy if a polymorphism is present in the subject. Alternatively, a subject can be included as responsive to the therapy if a polymorphism is not present in the subject. In one aspect, the polymorphism is selected from the group consisting of SIGMAR1_Q2P, COMT_L146fs, KANSL1_P1010L/P304L/P946L, DHCR7_M220T, HLA-DRB1_A244T, HLA-DRB1_S66Y, HLA-DRB1_Y89S, MS4A6E_M59T, RIN3_H215R, DPYD_1543V, and combinations thereof. In another aspect, the polymorphism is selected from the group consisting of SIGMAR1_Q2P, COMT_L146fs, and combinations thereof. The presence of the polymorphism can be detected by evaluating nucleic acid sequences.

In other aspects, the method is used to select a subject responsive to Sigma-1 receptor agonist therapy. The method comprises obtaining the results of a test of a biological sample from the subject which determines the level of expression of RNA encoded by at least one gene selected from the group consisting of SIGMAR1, COMT, KANSL1, DHCR7, HLA-DRB1, MS4A6E, RIN3, and combinations thereof, and excluding the subject as non-responsive to Sigma-1 receptor agonist therapy if a level of RNA is substantially different from the level of RNA in a subject responsive to Sigma-1 receptor therapy. Alternatively, a subject can be included as responsive to the therapy if a level of RNA is substantially similar to the level of the RNA in a subject responsive to Sigma-1 receptor therapy. In one aspect, the level of expression of RNA encoded by a gene selected from the group consisting of SIGMAR1, COMT, KANSL1, and combinations thereof.

In some aspects, the method is used to select subjects responsive to Sigma-1 receptor agonist therapy. The method comprises detecting RNA expression in a test of a biological sample from the subject which determines the level of expression of RNA encoded by at least one gene selected from the group consisting of SIGMAR1, COMT, KANSL1, DHCR7, HLA-DRB1, MS4A6E, RIN3, and combinations thereof. The method comprises excluding the subject as non-responsive to Sigma-1 receptor agonist therapy if a level of RNA is substantially different from the level of RNA in a subject responsive to Sigma-1 receptor therapy. Alternatively, the method comprises identifying the subject as responsive to Sigma-1 receptor agonist therapy if a level of RNA is substantially similar to the level of RNA in a subject responsive to Sigma-1 receptor therapy. In one aspect, the level of expression of RNA encoded by a gene selected from the group consisting of SIGMAR1, COMT, KANSL1, and combinations thereof, is determined.

In some aspects, the method is used to treat a subject in need of Sigma-1 receptor agonist therapy. The method comprises obtaining the results of a test of a biological sample from the subject which determines the presence of at least one polymorphism. If a polymorphism is not present in the subject, a therapeutically effective amount of a Sigma-1 receptor agonist is administered to the subject. Alternatively, if a polymorphism is present in the subject, a therapeutically effective amount of an alternative to Sigma-1 receptor agonist is administered to the subject. In one aspect, the polymorphism is selected from the group consisting of SIGMAR1_Q2P, COMT_L146fs, KANSL1_P1010L/P304L/P946L, DHCR7_M220T, HLA-DRB1_A244T, HLA-DRB1_S66Y, HLA-DRB1_Y89S, MS4A6E_M59T, RIN3_H215R, DPYD_1543V, and combinations thereof. In another aspect, the polymorphism is selected from the group consisting of SIGMAR1_Q2P, COMT_L146fs, COMT_L146fs, KANSL1_P1010L/P304L/P946L, and combinations thereof. The presence of the polymorphism can be obtained by evaluating nucleic acid sequences.

In other aspects, the method is used to treat a subject in need of Sigma-1 receptor agonist therapy. The method comprises obtaining the results of a test of a biological sample from the subject which determines the level of expression of RNA encoded by a gene selected from the group consisting of SIGMAR1, COMT, KANSL1, DHCR7, HLA-DRB1, MS4A6E, RIN3, and combinations thereof. If the level of RNA in the test sample is substantially similar to the level of RNA obtained from a subject responsive to Sigma-1 receptor therapy, a therapeutically effective amount of a Sigma-1 receptor agonist is administered to the subject. Alternatively, if the level of RNA in the test sample is substantially different from the level of RNA obtained from a subject responsive to Sigma-1 receptor therapy, a therapeutically effective amount of an alternative to Sigma-1 receptor agonist is administered to the subject. In another aspect, the level of expression of RNA encoded by a gene selected from the group consisting of SIGMAR1, COMT, KANSL1, and combinations thereof, is determined.

It will be recognized that a subject can have more than one polymorphism. For instance, the subject can have 1, 2, 3, 4, 5, 6, 7, 8, 9, 10, or more polymorphisms. In some aspects, the subject has 1, 2, 3, 4, 5, 6, 7, 8, 9, or 10 polymorphisms. In other aspects, the subject has 1, 2, 3, 4, or 5 polymorphisms. In yet other aspects, the subject has 1, 2, or 3 polymorphisms.

IV. Treating a Subject in Need of Sigma-1 Receptor Agonist

Sig-1R expression or activity is linked to neurodegeneration, and the activation of Sig-1R is associated with neuroprotection in human subjects and in different in vitro and in vivo models. Therefore, one aspect of the disclosure encompasses treatment of any Sigma-1 receptor-related disease or condition which primarily affects the neuronal system in a subject. Such conditions include conditions variously known as neurodevelopmental and neurodegenerative diseases and conditions, and can be used for neuroprotection. Non-limiting examples of neurodegenerative diseases include Alzheimer's disease, Parkinson's disease, prion diseases, Huntington's disease, motor neuron diseases (MND) such as amyotrophic lateral sclerosis, spinocerebellar ataxia (SCA), spinal muscular atrophy (SMA), dementia, autism spectrum disorder, cerebral palsy, Rett syndrome, Angelman syndrome, Williams syndrome, pervasive developmental disorder not otherwise specified (PDD-NOS), multiple sclerosis, childhood disintegrative disorder, Fragile X, infantile spasms and Smith-Magenis syndrome, schizophrenia, post-traumatic stress disorder (PTSD), and any neuronal injury such as injury resulting from a stroke, traumatic brain injury, and spinal cord injury.

SIGMAR1 is also useful as a target for cancer treatment. As such, one aspect of the disclosure encompasses treatment of any Sigma-1 receptor-related cancer or neoplasm. As it will be recognized by individuals skilled in the art, cancer as used throughout the instant disclosure may be one or more neoplasm or cancer. The neoplasm may be malignant or benign, the cancer may be primary or metastatic, the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenstrom), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

The method comprises administering a therapeutically effective amount of an alternative to Sigma-1 receptor agonist when a subject in need of Sigma-1 receptor agonist therapy is determined to be non-responsive to the therapy. Non-limiting examples of alternatives to Sigma-1 receptor agonist include galantamine, memantine, and rivastigmine.

The method comprises administering a therapeutically effective amount of a Sigma-1 receptor agonist when a subject in need of Sigma-1 receptor agonist therapy is determined to be responsive to the therapy. A sigma-1 receptor agonist may be any therapeutic or active agent capable of treating a subject in need of Sigma-1 receptor agonist therapy. For instance, a receptor agonist can be a biological compound such as an antibody or a peptide, or a small molecule active agent. Non-limiting examples of Sigma-1 receptor agonists include entacapone, nebicapone, nitecapone, opicapone, tolcapone, tetrahydro-N,N-dimethyl-2,2-diphenyl-3-furanmethanamine hydrochloride (ANAVEX2-73, AV2-73, or A2-73), 1-(2,2-diphenyltetrahydrofuran-3-yl)-N-methylmethanamine hydrochloride (ANAVEX19-144, or A19-144), aminotetrahydrofuran derivative tetrahydro-N,N-dimethyl-5,5-diphenyl-3-furanmethanamine hydrochloride (ANAVEX1-41), 1-(3-4(((1R, 3S,5S)-adamantan-1-yl)(phenyl)methyl)propyl)-4-methylpiperazine (ANAVEX™ 1066 or "AV1066"), ANAVEX3-71 (also known as AF710B), PRE-084, donepezil, fluvoxamine, amitriptyline, L-687,384, and combinations thereof. Sigma-1 receptor agonists may also be antibodies In one aspect, the Sigma-1 receptor agonist is A2-73. When the agonist is A2-73, the therapeutically effective amount of A2-73 can range from about 0.5 mg to about 20 mg, about 1 mg to about 60 mg, about 30 mg to about 50 mg, or about 3 mg to about 5 mg. In one aspect, the therapeutically effective amount of A2-73 ranges about 20 to about 60 mg when administered orally. In another aspect, the therapeutically effective amount of A2-73 ranges from about 1 to about 20 mg when administered intravenously. In another aspect, the therapeutically effective amount of A2-73 ranges from about 40 mg to about 60 mg/day. The therapeutically effective amount of A2-73 can range from about 0.5 mg/day to about 100 mg/day, from about 1 to about 60 mg/day, from about 20 to about 50 mg/day, from about 20 to about 30 mg/day, or from about 15 to about 25 mg/day. Administering the anti-neurodegenerative effective amount of A2-73 can provide blood levels of about 10 ng/ml, about 12 ng/ml of A2-73.

A2-73 can be administered to the subject daily or more than once daily. Further, A2-73 can be administered every 2, 3, 4, 5, 6, 7, 14, or every 30 days. A2-73 can be administered over a period ranging from about 1 day to about 1 year, from about 1 day to about 1 week, from about 3 days to about 1 month, from about 2 weeks to about 6 months, or from about 2 months to about 4 months. A2-73 can also be administered over a period of about 1 day, about 7 days, about 30 days, about 60 days, about 120 days, or about 180 days or more. In some aspects, A2-73 is administered over a period of about 57 weeks, about 148 weeks, about 208 weeks, indefinitely, or until resolution of the condition being treated.

Other methods of administering A2-73 can be found in, e.g., U.S. Pat. No. 9,750,746, U.S. Patent Publication No. 20170360798, U.S. Patent Publication No. 20190022052, U.S. Patent Publication No. 20180360796, U.S. Patent Publication No. 20180169059, U.S. Patent Publication No. 20180177756, U.S. Patent Publication No. 20180169060, and U.S. Patent Publication No. 20190117615, the disclosures of which are incorporated herein in their entirety.

V. Pharmaceutical Formulations

One aspect of the disclosure encompasses a pharmaceutical formulation for diagnosis and delivery of Sigma-1 receptor agonists. A pharmaceutical formulation comprises a therapeutically effective amount of agonists and any pharmaceutically acceptable salt thereof.

Pharmaceutically acceptable salts of the compound comprising Formulas (II) or (IIa) include, without limitation, acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methylbromide, methanesulfonate, monohydrate, mucate, nitrate, oxalate, phenylpropionate, phosphate, phthalate, propionate, pyruvate, salicylate, stearate, succinate, sulfate, tannate, tartrate, terephthalate, valerate, and the like.

When the Sigma-1 receptor agonist is A2-73, a formulation can comprise from about 1 mg to about 50 g, from about 0.1 to about 5 g, from about 0.5 g to about 3 g, from about 1 mg to about 55 mg, from about 40 mg to about 60 mg, from about 80 mg to about 120 mg, from about 180 mg to about 220 mg, from about 0.1 g to about 5 g, or from about 0.5 g to about 3 g of A2-73. Formulations comprising A2-73 can be found in, e.g., U.S. Pat. No. 9,750,746, U.S. Patent Publication No. 20170360798, U.S. Patent Publication No. 20190022052, U.S. Patent Publication No. 20180360796, U.S. Patent Publication No. 20180169059, U.S. Patent Publication No. 20180177756, U.S. Patent Publication No. 20180169060, and U.S. Patent Publication No. 20190117615, the disclosures of which are incorporated herein in their entirety.

Sigma-1 receptor agonists can be formulated and administered to a subject by several different means. For instance, a composition can generally be administered parenterally, intraperitoneally, intravascularly, transdermally, subcutaneously, or intrapulmonarily in dosage unit formulations containing conventional nontoxic pharmaceutically acceptable adjuvants, carriers, excipients, and vehicles as desired. The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

A pharmaceutical formulation comprises one or more pharmaceutically acceptable excipients. Non-limiting examples of excipients include chemical enhancers, humectants, pressure sensitive adhesives, antioxidants, solubilizers, thickening agents, plasticizers, adjuvants, carriers, excipients, vehicles, coatings, and any combinations thereof. One or more excipients can be selected for oral, transdermal, parenteral, intraperitoneal, intravascular, subcutaneous, by inhalation spray, rectal, or intrapulmonary administration.

A Sigma-1 receptor agonist can in general be formulated for improving patient compliance, preventing a subject from removing the drug-delivery device. For instance, Sigma-1 receptor agonists could be formulated for improved patient compliance and preventing removal of a drug-delivery device by providing formulations for extended delivery. Extended delivery can range for periods ranging from more than one day, to months. This may be especially relevant for patients with compromised cognitive and/or motor-control abilities. Extended delivery for periods can range from about 1 day to about 1 year, from about 1 day to about 1 week, from about 3 days to about 1 month, from about 2 weeks to about 6 months, or from about 2 months to about 4 months.

Extended release formulations could be used for substantially continuous delivery of drug at a preselected rate. For example, for crystalline A2-73, the drug can be delivered at a rate of from about 1 mg to about 100 mg/day, from about 40 to about 60 gm/day, or from about 10 to about 30 gm/day. Appropriate amounts of crystalline A2-73 can be readily determined by the ordinarily skilled artisan based upon, for example, the intended duration of administration of the drug by the extended release formulation, the delivery mechanism, the particular formulation, and the relative potency of the drug among other factors.

i. Binders

Non-limiting examples of binders suitable for the formulations of various aspects include starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohols, polyethylene glycol, polyols, saccharides, oligosaccharides, polypeptides, oligopeptides, and combinations thereof. The polypeptide may be any arrangement of amino acids ranging from about 100 to about 300,000 Daltons.

The binder can be introduced into the mixture to be granulated in a solid form, including but not limited to a crystal, a particle, a powder, or any other finely divided solid form known in the art. Alternatively, the binder can be dissolved or suspended in a solvent and sprayed onto the mixture in a granulation device as a binder fluid during granulation.

ii. Diluents

Non-limiting examples of diluents (also referred to as "fillers" or "thinners") include carbohydrates, inorganic compounds, and biocompatible polymers, such as polyvinylpyrrolidone (PVP). Other non-limiting examples of diluents include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, saccharides such as sucrose, dextrose, lactose, microcrystalline cellulose, fructose, xylitol, and sorbitol, polyhydric alcohols; starches; pre-manufactured direct compression diluents; and mixtures of any of the foregoing.

iii. Disintegrants

Disintegrants can be effervescent or non-effervescent. Non-limiting examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include but are not limited to sodium bicarbonate in combination with citric acid, and sodium bicarbonate in combination with tartaric acid.

iv. Preservatives

Non-limiting examples of preservatives include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

v. Flavor-Modifying Agents

Suitable flavor-modifying agents include flavorants, taste-masking agents, sweeteners, and the like. Flavorants include, but are not limited to, synthetic flavor oils and flavoring aromatics and/or natural oils, extracts from plants, leaves, flowers, fruits, and combinations thereof. Other non-limiting examples of flavors include cinnamon oils, oil of wintergreen, peppermint oils, clover oil, hay oil, anise oil, eucalyptus, vanilla, citrus oils such as lemon oil, orange oil, grape and grapefruit oil, fruit essences including apple, peach, pear, strawberry, raspberry, cherry, plum, pineapple, and apricot.

Taste-masking agents include but are not limited to cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other aspects, additional taste-masking agents contemplated are those described in U.S. Pat. Nos. 4,851,226; 5,075,114; and 5,876,759, each of which is hereby incorporated by reference in its entirety.

Non-limiting examples of sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia rebaudiana (Stevioside); chloro derivatives of sucrose such as sucralose; sugar alcohols such as sorbitol, mannitol, sylitol, hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

vi. Lubricants and Glidants

The lubricant compositions may be utilized to lubricate ingredients that form a pharmaceutical composition. As a glidant, the lubricant facilitates removal of solid dosage forms during the manufacturing process. Non-limiting examples of lubricants and glidants include magnesium stearate, calcium stearate, zinc stearate, hydrogenated vegetable oils, sterotex, polyoxyethylene monostearate, talc, polyethylene glycol, sodium benzoate, sodium lauryl sulfate, magnesium lauryl sulfate, and light mineral oil. The pharmaceutical composition will generally comprise from about 0.01% to about 10% by weight of a lubricant. In some aspects, the pharmaceutical composition will comprise from about 0.1% to about 5% by weight of a lubricant. In a further aspect, the pharmaceutical composition will comprise from about 0.5% to about 2% by weight of a lubricant.

vii. Dispersants

Dispersants may include but are not limited to starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants.

viii. Colorants

Depending upon the aspect of the disclosure, it may be desirable to include a coloring agent. Suitable color additives include but are not limited to food, drug and cosmetic colors (FD&C), drug and cosmetic colors (D&C), or external drug and cosmetic colors (Ext. D&C). These colors or dyes, along with their corresponding lakes, and certain natural and derived colorants, may be suitable for use in various aspects of the disclosure.

ix. pH Modifiers

Non-limiting examples of pH modifiers include citric acid, acetic acid, tartaric acid, malic acid, fumaric acid, lactic acid, phosphoric acid, sorbic acid, benzoic acid, sodium carbonate and sodium bicarbonate.

x. Chelating Agents

A chelating agent may be included as an excipient to immobilize oxidative groups, including but not limited to metal ions, in order to inhibit the oxidative degradation of the morphinan by these oxidative groups. Non-limiting examples of chelating agents include lysine, methionine, glycine, gluconate, polysaccharides, glutamate, aspartate, and disodium ethylenediaminetetraacetate ($Na_2EDTA$).

xi. Antimicrobial Agents

An antimicrobial agent may be included as an excipient to minimize the degradation of the compound according to this disclosure by microbial agents, including but not limited to bacteria and fungi. Non-limiting examples of antimicrobials include parabens, chlorobutanol, phenol, calcium propionate, sodium nitrate, sodium nitrite, $Na_2EDTA$, and sulfites including but not limited to sulfur dioxide, sodium bisulfite, and potassium hydrogen sulfite.

xii. Release-Controlling Polymers

Release-controlling polymers may be included in the various aspects of the solid dosage pharmaceutical compositions incorporating compounds according to this disclosure. In one aspect, the release-controlling polymers may be used as a tablet coating. In other aspects, including but not limited to bilayer tablets, a release-controlling polymer may be mixed with the granules and other excipients prior to the formation of a tablet by a known process including but not limited to compression in a tablet mold. Suitable release-controlling polymers include but are not limited to hydrophilic polymers and hydrophobic polymers.

Suitable hydrophilic release-controlling polymers include, but are not limited to, cellulose acetate, cellulose diacetate, cellulose triacetate, cellulose ethers, hydroxyethyl cellulose, hydroxypropyl cellulose, hydroxypropyl methylcellulose, microcrystalline cellulose, nitrocellulose, cross-linked starch, agar, casein, chitin, collagen, gelatin, maltose, mannitol, maltodextrin, pectin, pullulan, sorbitol, xylitol, polysaccharides, ammonia alginate, sodium alginate, calcium alginate, potassium alginate, propylene glycol alginate, alginate sodium carmellose, calcium carmellose, carrageenan, fucoidan, furcellaran, arabic gum, carrageens gum, ghafti gum, guar gum, karaya gum, locust bean gum, okra gum, tragacanth gum, scleroglucan gum, xanthan gum, hypnea, laminaran, acrylic polymers, acrylate polymers, carboxyvinyl polymers, copolymers of maleic anhydride and styrene, copolymers of maleic anhydride and ethylene, copolymers of maleic anhydride propylene or copolymers of maleic anhydride isobutylene), crosslinked polyvinyl alcohol and poly N-vinyl-2-pyrrolidone, diesters of polyglucan, polyacrylamides, polyacrylic acid, polyamides, polyethylene glycols, polyethylene oxides, poly(hydroxyalkyl methacrylate), polyvinyl acetate, polyvinyl alcohol, polyvinyl chloride, polystyrenes, polyvinylpyrrolidone, anionic and cationic hydrogels, and combinations thereof.

xiii. Coatings

A solid dosage comprising a compound according to this disclosure may comprise a coating, wherein such a coating may control release of the compound, act as a moisture barrier, or buffer or modify pH. A "control releasing coat" or "controlled release coat" as used herein is defined to mean a functional coat which can for example comprise at least one pH independent polymer, pH dependent polymer (for example enteric or reverse enteric type polymers), soluble polymer, insoluble polymer, lipids, lipidic materials, or combinations thereof. The coating, when applied onto a dosage form, may slow (for example when applied to a normal release matrix dosage form), further slow (for example when applied to a controlled release matrix dosage form) or modify the rate of release of a compound according to this disclosure when applied to an uncoated dosage form. For example, the control releasing coat can be designed such that when the control releasing coat is applied to a dosage form, the dosage form in conjunction with the control releasing coat can exhibit the release of the compound according to this disclosure, such as a "modified-release", "controlled-release", "sustained-release", "extended-release", "delayed-release", "prolonged-release," or combinations thereof. The "control releasing coat" may optionally comprise additional materials that may alter the functionality of the control releasing coat.

The term "moisture barrier" as used herein is one which impedes or retards the absorption of moisture. Compounds according to this disclosure may be hygroscopic and, as such, may be susceptible to decomposition over time under highly humid conditions. The proportion of the components of the moisture barrier and the amount of the moisture barrier optionally applied onto the control-releasing coating or onto the core are typically such that the moisture barrier does not fall within the USP definition and requirement for an enteric coat. Suitably, the moisture barrier may comprise an enteric and/or acrylic polymer, suitably an acrylic polymer, optionally a plasticizer, and a permeation enhancer. The permeation enhancer is a hydrophilic substance, which allows water to enter without physical disruption of the coating. The moisture barrier may additionally comprise other conventional inert excipients, which may improve processing of an extended-release formulation.

Coating and matrix materials which may be used in accordance with the invention are those known in the art for use in controlled-release formulations, such as synthetic polymers of the polyvinyl type, e.g., polyvinylchloride, polyvinylacetate and copolymers thereof, polyvinylalcohol, and polyvinylpyrrolidone; synthetic polymers of the polyethylene type, e.g., polyethylene and polystyrene; acrylic acid polymers; biopolymers or modified biopolymers, such as cellulosic polymers, shellac and gelatin; fats, oils, higher fatty acids and higher alcohols (i.e., acids and alcohols containing alkyl chains of at least 10 carbon atoms), for example aluminum monostearate, cetylalcohol, hydrogenated beef tallow, hydrogenated castor oil, 12-hydroxystearl alcohol, glyceryl mono- or dipalmitate; glyceryl mono-, di- or tristearate; myristyl alcohol, stearic acid, stearyl alcohol, and polyethyleneglycols; waxes; sugars and sugar alcohols.

The pH-buffering properties of a coating may be strengthened by introducing into the coating substances chosen from a group of compounds usually used in antacid formulations, for example magnesium oxide, hydroxide or carbonate, aluminum or calcium hydroxide, carbonate or silicate; composite aluminum/magnesium compounds, for example $Al_2O_3 \cdot 6MgO \cdot CO_2 \cdot 12H_2O$, $(Mg_6Al_2(OH)_{16}CO_3 \cdot 4H_2O)$, $MgO \cdot Al_2O_3 \cdot 2SiO_2 \cdot nH_2O$, aluminum bicarbonate coprecipitate or similar compounds; or other pharmaceutically acceptable pH-buffering compounds, for example the sodium, potassium, calcium, magnesium and aluminum salts of phosphoric, carbonic, citric or other suitable, weak, inorganic or organic acids; or suitable organic bases, including basic amino acids; and salts or combinations thereof.

A pH-dependent coating serves to release the drug in desired areas of the gastrointestinal (GI) tract, e.g., the stomach or small intestine. When a pH-independent coating is desired, the coating is designed to achieve optimal release regardless of pH-changes in the environmental fluid, e.g., the GI tract. When the coating is formulated to release a compound according to this disclosure in the intestines (especially the upper small intestines), the coating is often called an "enteric coating". A pH-dependent coating may include, but is not limited to, acrylic acid polymers and copolymers, for example polymers formed from acrylic acid, methacrylic acid, methyl acrylate, ammonio methylacrylate, ethyl acrylate, methyl methacrylate and/or ethyl methacrylate (e.g., Eudragit™); cellulosic polymers such as hydroxypropyl cellulose, hydroxyethyl cellulose, hydroxypropyl methyl cellulose, methyl cellulose, ethyl cellulose, cellulose acetate, cellulose acetate phthalate (CAP), cellulose acetate trimellitate, hydroxypropylmethyl cellulose phthalate, hydroxypropylmethyl cellulose succinate and carboxymethylcellulose sodium; shellac (purified lac); vinyl polymers and copolymers such as polyvinyl pyrrolidone, polyvinyl acetate, polyvinylacetate phthalate (PVAP), vinylacetate crotonic acid copolymer, and ethylene-vinyl acetate copolymers; zein; and salts and combinations thereof.

VI. Dosage Forms

One aspect of the disclosure encompasses dosage forms of Sigma-1 receptor agonists. When the agonist is A2-73, the dosage form can comprise from about 1 mg to about 50 g, from about 1 mg to about 500 mg, from about 1 mg to about 100 mg, from about 1 mg to about 500 mg, from about 50 to about 400 mg, from about 75 to about 150 mg, from about 150 to about 200 mg, from about 40 mg to about 60 mg, from about 80 mg to about 120 mg, or from about 180 mg to about 220 mg of A2-73. For instance, the dosage form can comprise 1, 10, 20, 30, 40, 50, 60, 70, 80, 90, 100, 120, 140, 160, 180, 200, 220, 240, 260, 280, or 300 or more mg of A2-73. In some aspects, dosage forms can comprise from about 1 mg to about 500 mg, or about 1 mg to about 100 mg of A2-73.

Dosage forms include those formulated for extended or slow release, and those formulated for immediate release. For example, an immediate release dosage form may include a crystalline form of A2-73 as the free base or as a A2-73 salt as disclosed herein. For example, a fast-dissolve oral dosage form may include for example an A2-73 salt, such as the HCl salt. Alternatively, a dosage form may include a crystalline form of A2-73 as the free base or as a A2-73 salt formulated for inhalation drug delivery, either as a dry powder or aerosol spray.

Dosage forms also include those formulated for topical administration. For instance, a dosage form can be formulated as one or more of a gel, ointment, emulsion, microemulsion, solution, suspension, paste, gel, foam, spray, lotion, or cream. In one aspect, a topical administration dosage form is a transdermal patch. When the dosage form is formulated as a transdermal patch, the transdermal patch can contain from about 40 mg to about 60 mg, from about 80 mg to about 120 mg, or from about 180 mg to about 220 mg of A2-73 freebase in crystalline form.

Dosage forms can alternatively be formulated for oral administration. Dosage forms formulated for oral administration can be tablets to swallow, chew, or dissolve in water or under the tongue, capsules and chewable capsules, powders, granules, teas, drops, or liquid medications or syrups. In some aspects, the dosage form is an enteric coated oral formulation.

When the dosage form is an enteric coated oral formulation, the formulation can comprise from about 0.1 mg to about 60 mg A2-73 freebase, preferably from about 1 mg to about 50 mg A2-73 freebase.

An enteric coated oral formulation can also contain A2-73 salt in crystalline form. The A2-73 salt can be a fumarate salt, a sulfate salt, a mesylate salt, a dihydrogen phosphate salt, an edisylate salt, a benzoate salt, a hydrochloride salt, and an oxalate salt. In one aspect, the A2-73 salt is a fumarate salt. When the A2-73 salt is a fumarate salt, the enteric coated oral formulation can comprise from about 0.1 to about 100 mg of A2-73 fumarate salt, preferably from about 1 mg to about 55 mg of A2-73 fumarate salt.

Dosage forms also encompass those formulated for subcutaneous and/or intramuscular injection. For example, an intramuscular dosage form may comprise A2-73 in the free base form, dissolved in an oil matrix for intramuscular injection, or alternatively prepared as a suspension of the free base for intramuscular injection. A dosage form formulated for subcutaneous or intramuscular injection may comprise A2-73 in a salt or free base form as disclosed herein, prepared as microspheres using methods known in the art. Alternatively, A2-73 in free base or salt form may be coated, for example using Atomic Layer Deposition (ALD) techniques, with a thin layer coating such as a coating of zinc oxide, and used in a formulation for subcutaneous or intramuscular injection. Alternatively, A2-73 free base may be dissolved in a biodegradable polymer matrix, and then implanted subcutaneously (or used in a transdermal patch as detailed further below).

VII. Kits

A further aspect of the present disclosure provides kits comprising one or more reagents for use with a method of the disclosure. The kits may comprise cell growth media, selection media, nucleic acid sequencing and purification reagents, protein purification reagents, buffers, and the like. The kits provided herein generally include instructions for carrying out the methods detailed below. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions Definitions Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above-described cells and methods without departing from the scope of the invention, it is intended that all matter contained in the above description and in the examples given below, shall be interpreted as illustrative and not in a limiting sense.

The term "comprising" means "including, but not necessarily limited to"; it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

As used herein, the term "genotype" means an unphased 5' to 3' sequence of nucleotide pairs found at one or more polymorphic sites in a locus on a pair of homologous chromosomes in an individual. As used herein, genotype includes a full-genotype and/or a sub-genotype.

As used herein, the terms "locus" or "genetic locus" are used interchangeably and refer to a location on a chromosome or DNA molecule corresponding to a gene or a physical or phenotypic feature.

As used herein, the term "mutant" means any heritable variation from the wild-type that is the result of a mutation, e.g., single nucleotide polymorphisms ("SNP") and insertions/deletions. The term "mutant" is used interchangeably with the terms "marker", "biomarker", and "target" throughout the specification.

As used herein, the term "medical condition" includes, but is not limited to, any condition or disease manifested as one or more physical and/or psychological symptoms for which treatment is desirable, and includes previously and newly identified diseases and other disorders.

As used herein, the term "nucleotide pair" means the nucleotides found at a polymorphic site on the two copies of a chromosome from an individual.

As used herein, the terms "polymorphism", "polymorphic variant", and "polymorphic site" are used interchangeably and refer to a position within a locus at which at least two alternative sequences are found. A polymorphic variant of a gene can lead to the abnormal expression or to the production of an abnormal form of the protein, this abnormality may cause or be associated with disease.

As used herein, the term "polynucleotide" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "polypeptide" means any polypeptide comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well-known in the art. Such modifications are well described in basic texts and in more detailed monographs, as well as in a voluminous research literature.

As used herein, the term "single nucleotide polymorphism (SNP)" means nucleotide variability at a single position in the genome, in which two alternative bases occur at appreciable frequency (i.e., >1%) in the human population. A SNP may occur within a gene or within intergenic regions of the genome. SNP probes according to the invention are oligonucleotides that are complementary to a SNP and its flanking nucleic acid sequence(s).

As used herein, the term "subject" means that preferably the subject is a mammal, such as a human, but can also be an animal, e.g., domestic animals (e.g., dogs, cats and the like), farm animals (e.g., cows, sheep, pigs, horses and the like) and laboratory animals (e.g., cynomolgus monkey, rats, mice, guinea pigs and the like).

As used herein, the administration of an agent or drug to a subject or patient includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

EXAMPLES

The publications discussed above are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Figure 1B:
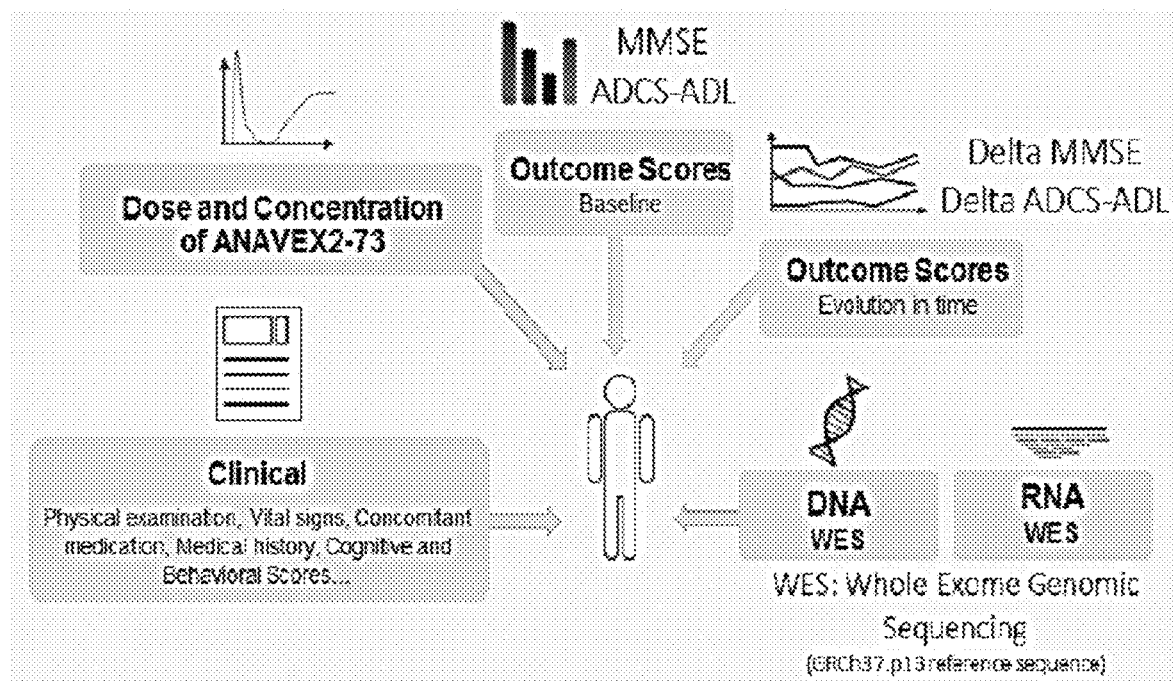
FIG. 1B: Summary of integrated data sources.

Example 1. Study Design, Safety, and Tolerability of ANAVEX2-73, and Patient Characteristics ANAVEX2-73, an agonist of SIGMAR1, has been shown by PET scan to directly bind its target and to modulate cholinergic muscarinic receptors in mice. ANAVEX2-73's clinical potential in AD was initially assessed in mice, followed by a Phase 1 study in healthy volunteers and a 57-week Phase 2a AD study. This study, a 57-week study (FIG. 1A), enrolled 32 patients with mild to moderate AD and met its primary endpoint of safety and tolerability (Table 2), leading to a 208-week extension study, termed the 208-week study (FIG. 1A). Patients enrolled in the 2 studies were characterized at baseline and at each visit, including collection of data on clinical descriptors, physical examination, pharmacokinetics and MMSE and ADCS-ADL as efficacy measures (FIG. 1B and Table 3).

TABLE 2

Summary of subject disposition in 57-week study and the 208-week extension study.

|  |  | Enrolled, N | Completed or still-ongoing*, N (%) | Discontinued, N (%) |
|---|---|---|---|---|
| 57-week study | Part A | 32 | 30 (93.8) | 2 (6.3) |
|  | Part B | 30 | 25 (83.3) | 5 (16.7) |
| 208-week study | Ext. Study | 24 | 21* (87.5) | 3* (12.5) |

Ext. study: extension study
*number of patients in on-going trial ANAVEX2-73-003 at interim cumulative week 148

TABLE 3

Baseline Characteristics

|  | All patients at baseline (N = 32) | Patients having genomic data (N = 21) |
|---|---|---|
| Age, mean ± SD | 68.9 ± 9.84 | 67.9 ± 9.85 |
| Male, n (%) | 19 (59.4) | 10 (47.6) |
| Height (cm), mean ± SD | 169.9 ± 10.38 | 169.2 ± 9.84 |
| Weight (cm), mean ± SD | 76.8 ± 14.79 | 78.3 ± 16.31 |
| Cardiovascular disease, n (%) | 20 (62.5) | 12 (57.1) |
| Donepezil on-going treatment, n (%) | 25 (78.1) | 16 (76.2) |
| ApoE e4-positive, n (%) | 18 (56.3) | 10 (47.6) |
| ApoE e3/e4, n (%) | 14 (43.6) | 7 (33.3) |
| ApoE e4/e4, n (%) | 4 (12.6) | 3 (14.3) |
| Mini-Mental State Examination (MMSE), mean ± SD | 21.0 ± 3.16 | 21.0 ± 2.73 |
| ADCS-ADL, mean ± SD | 69.0 ± 6.83 | 70.6 ± 4.08 |
| Rosen Modified Hachinski Ischemic score, mean ± SD | 1.0 ± 0.67 | 1.0 ± 0.63 |
| Hamilton Psychiatric Rating Scale for Depression (HAM-D), mean ± SD | 2.1 ± 2.18 | 2.2 ± 2.48 |

Example 2. Identification of Genomic Biomarkers

Figure 1C:
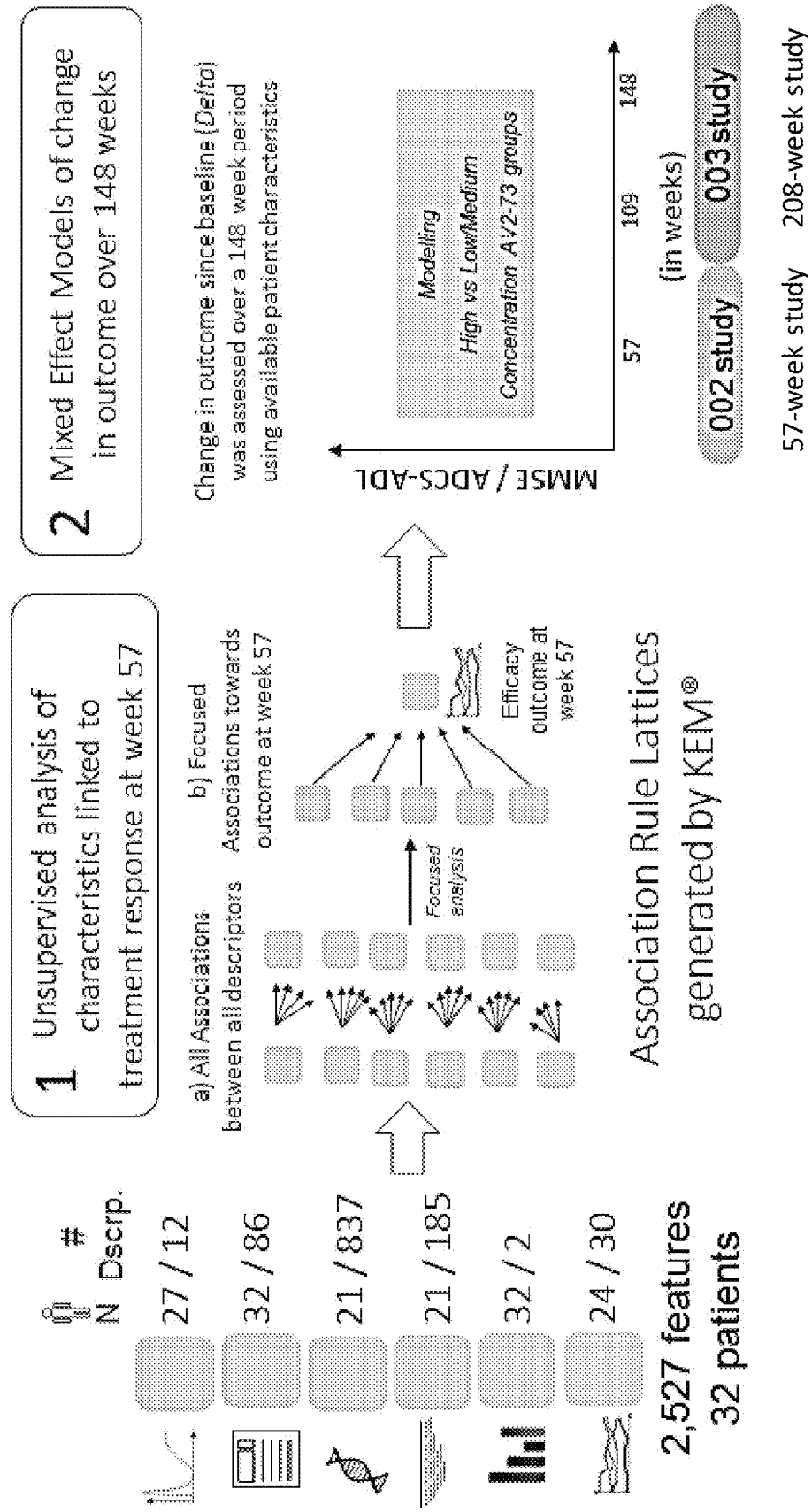
FIG. 1C: Description of number of patient descriptors incorporated in the two analytical steps applied in the study 1) Unsupervised FCA rule-based analysis of response at week 57, 2) Longitudinal confirmation using Mixed Effect modelling of response over 148 weeks incorporating markers found at week 57 to model two groups of ANAVEX2-73 concentrations.

Genomic characterization of patients' tumors is routinely performed in oncology studies to identify and rank genomic biomarkers of disease and therapeutic response. Genetic polymorphisms are associated with variations in treatment response, modulating therapeutic response in a patient population. In this study, Whole Exome Sequencing (WES) and gene expression analysis (RNAseq) were performed at 109-135 weeks (FIG. 1B) for the 21 patients remaining in the extension trial. Genomic data integrated with longitudinal clinical and other patient characteristics including efficacy outcome measures and derived measures of progression, leads to phenotypic and genotypic precision medicine analysis (FIGS. 1B-C).

A small cohort, with the number of patient observations orders of magnitude smaller than number of attributes, constitutes an analytical challenge. In this study, an unsupervised Formal Concept Analysis method (FCA), based on Galois lattices, as implemented in the KEM software (v.3.6.2), was used to identify and rank phenotypic and genotypic biomarkers. No link is assumed in this analysis between biomarkers and outcomes, enabling a hypothesis free, data-driven, generation of all relations.

Figure 2A:
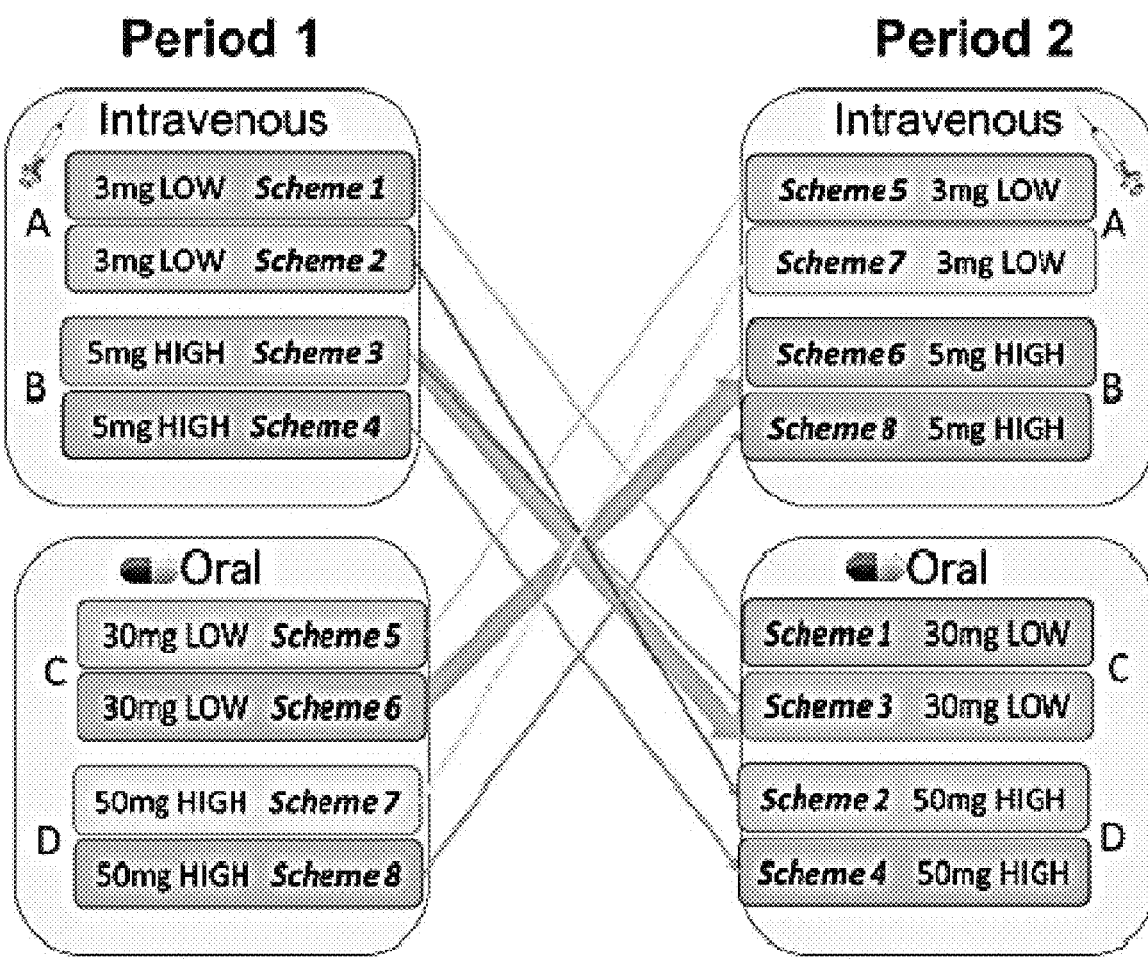
FIGS. 2A-2C. Schematic illustrations of dosages and plasma concentration of ANAVEX2-73 and ANAVEX19-144.
Figure 2B:
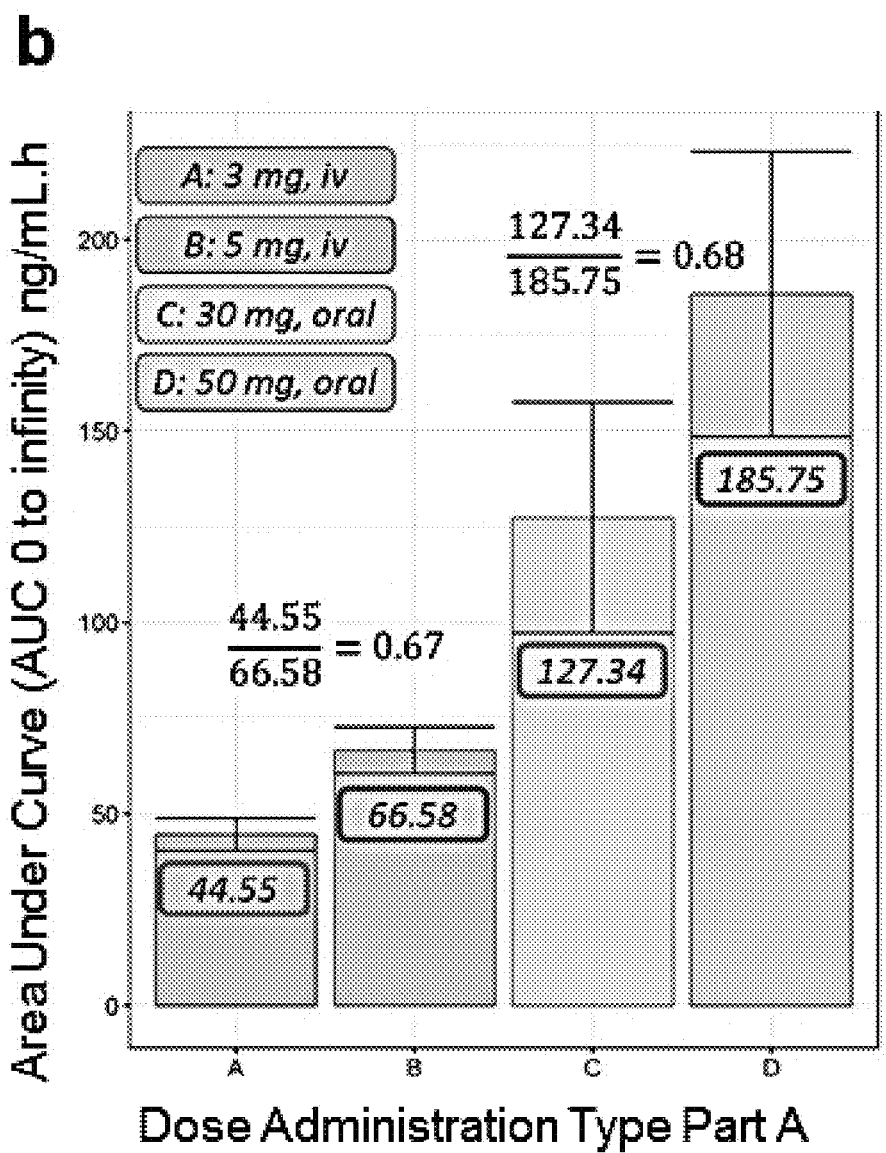
Figure 2C:
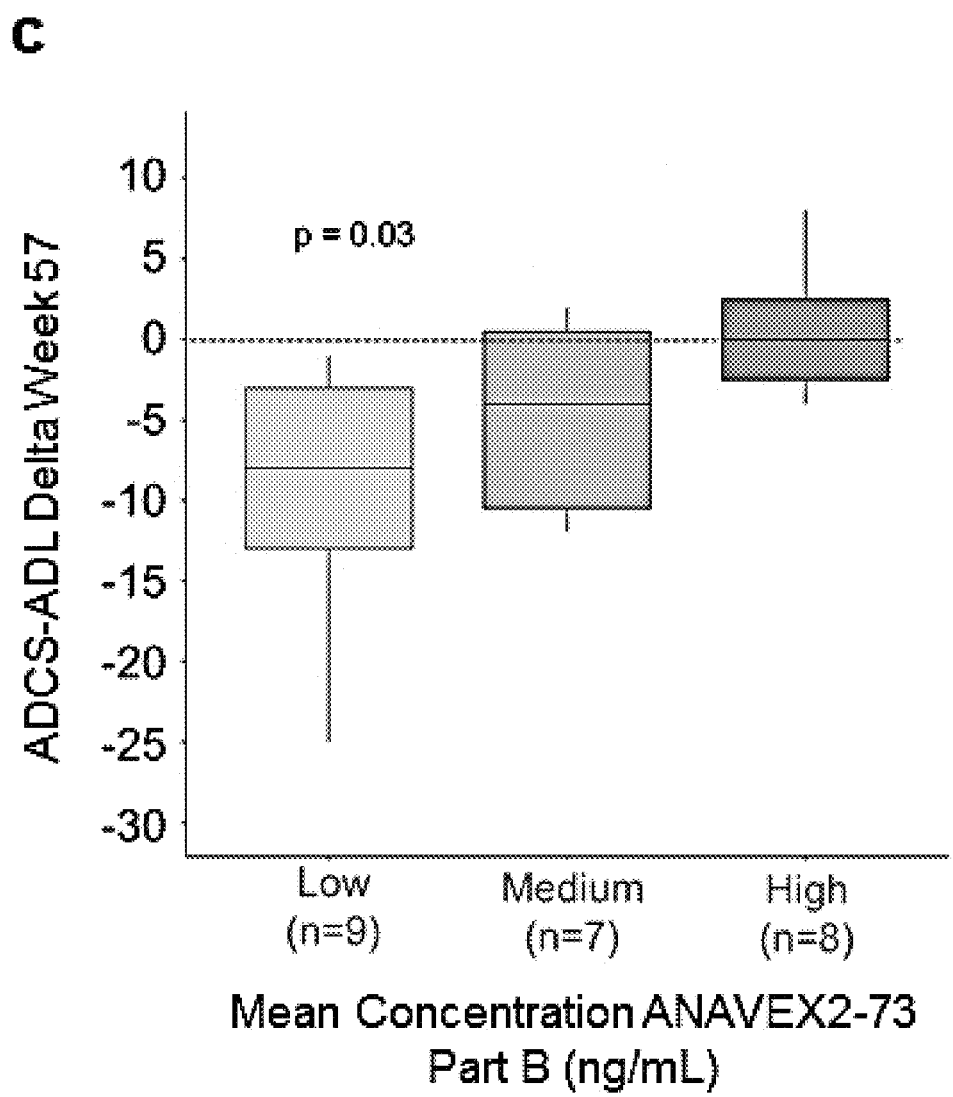

A total of 3,145,630 relations between all available features were explored. Stringent filtering excluded rules containing variables coding for the absence of DNA variants and medium RNA expression groups. Numerical filtering of rules involved the following thresholds: support ($n>3$), confidence ($>50\%$), lift ($\geq 1.2$) and p-value (Fisher Exact Test or Mann-Whitney-Wilcoxon<0.05). The filtering steps led to a subset of 1,019 association rules linking clinical, genomic and transcriptomics patient characteristics with response at multiple time points. A second filtering step focused on relationships with response at week 57 only, raising support$\leq 5$, and lift$\geq 1.5$, and excluding RNA expression, CYP variants and dose/concentration from Part A. This further reduced the number of rules to 15 associations linked to outcome as measured by Delta (with binarized discretization) or Slope of MMSE or ADCS-ADL at week 57. The 15 rules are presented in order of highest confidence and highest lift. The stringent filtering focused on relationships of response at week 57 (end of Part B), reduced the number of associations to only 15 linked to outcomes as measured by Delta or Slope MMSE or ADCS-ADL (Table 4). Within the 15 relations identified, average blood concentration of ANAVEX2-73 above 4 ng/mL in Part B increased the probability of improved MMSE outcome 1.88-fold at week 57 (Table 4). Higher concentrations improved Delta ADCS-ADL scores ($p=0.03$) (FIG. 2C). Lower MMSE baseline scores (<20) increased the relative probability (lift) of worse MMSE outcome by 1.5-fold, while higher MMSE baseline scores (>20) increased the relative probability of improved MMSE by 1.62-fold, both at week 57.

TABLE 4

| Antecedent X Patient Characteristic | Consequent Y | | | | Support | Confidence | Lift | Fisher Exact Test P-value | Mann-Whitney-Wilcoxon P-value | $n_x$ | $n_y$ |
|---|---|---|---|---|---|---|---|---|---|---|---|
|  | Endpoint | Deriv. | Outcome | Week | | | | | | | |
| SIGMAR1 Q2P variant | MMSE | Delta | Worsen | 57 | 5 | 1 | 1.75 | 0.039 | 0.081 | 5 | 12 |
| COMT L146fs variant | MMSE | Delta | Worsen | 57 | 5 | 1 | 1.75 | 0.039 | 0.106 | 5 | 12 |
| RmHis Hypertension history FALSE | ADCS-ADL | Delta | Worsen | 57 | 9 | 1 | 1.62 | 0.002 | 0.001 | 9 | 13 |

TABLE 4-continued

| Antecedent X Patient Characteristic | Consequent Y | | | | | | | Fisher Exact Test P-value | Mann-Whitney-Wilcoxon P-value | $n_x$ | $n_y$ |
| --- | --- | --- | --- | --- | --- | --- | --- | --- | --- | --- | --- |
| | Endpoint | Deriv. | Outcome | Week | Support | Confidence | Lift | | | | |
| MS4A6E M59T variant | ADCS-ADL | Delta | Worsen | 57 | 6 | 1 | 1.62 | 0.032 | 0.101 | 6 | 13 |
| COMT L146fs variant | ADCS-ADL | Delta | Worsen | 57 | 5 | 1 | 1.62 | 0.063 | 0.007 | 5 | 13 |
| SIGMAR1 Q2P variant | ADCS-ADL | Delta | Worsen | 57 | 5 | 1 | 1.62 | 0.063 | 0.035 | 5 | 13 |
| Baseline Score MMSE Low | MMSE | Slope | Worsen | 57 | 8 | 1 | 1.5 | 0.015 | 0.109 | 8 | 14 |
| HLA-DRB1 Y89S variant | MMSE | Slope | Worsen | 57 | 7 | 1 | 1.5 | 0.03 | 0.039 | 7 | 14 |
| HLA-DRB1 Y89S variant | MMSE | Delta | Worsen | 57 | 6 | 0.86 | 1.5 | 0.078 | 0.039 | 7 | 12 |
| DPYD I543V variant | MMSE | Delta | Improve | 57 | 5 | 0.71 | 1.67 | 0.08 | 0.043 | 7 | 9 |
| High Baseline Score ISRL | MMSE | Delta | Improve | 57 | 7 | 0.7 | 1.63 | 0.024 | 0.006 | 10 | 9 |
| RmHis Hypertension history TRUE | ADCS-ADL | Delta | Improve | 57 | 8 | 0.67 | 1.75 | 0.002 | 0.001 | 12 | 8 |
| High Concentration AV2-73 Part B | MMSE | Slope | Improve | 57 | 5 | 0.63 | 1.88 | 0.041 | 0.308 | 8 | 7 |
| High Baseline ScoremISRL | MMSE | Slope | Improve | 57 | 6 | 0.6 | 1.8 | 0.021 | 0.006 | 10 | 7 |
| High Baseline Score MMSE | MMSE | Slope | Improve | 57 | 7 | 0.54 | 1.62 | 0.015 | 0.109 | 13 | 7 |

Further focusing on relations displaying a 100% confidence and true for both Delta MMSE and Delta ADCS-ADL, two DNA variants were identified, SIGMAR1_Q2P and COMT_L146fs. Table 5 shows a summary of integrated data sources. A total of 2,527 features, from 1,152 descriptors, were used for each subject including 837 genomic sequences with amino acid changes, from a total of 27,155 annotated genes, and 185 RNA expression profiles. Patient descriptors are shown in grey and outcomes in pink. c. Description of number of patient descriptors incorporated in the two analytical steps applied in the study 1) Unsupervised FCA rule-based analysis of response at week 57, 2) Longitudinal confirmation using Mixed Effect modelling of response over 148 weeks incorporating markers found at week 57 to model two groups of ANAVEX2-73 concentrations.

Cytosol and, is believed to interact with other ligands. The identified SIGMAR1 variant (Glutamine (Gln) at position 2 changed into Proline-SIGMAR1_p.Q2P) is located at the N terminus of the protein and may hence have structural and functional implications. The Gln (Q) to Proline (P) alteration impacts the length of the side chain (extended in Gln) and may impact the ability of the amino acid to form an alpha helix. Proline is considered as a "helix breaker" which, in some instances, has been attributed to unwinding the N terminus of a helix. Retrospective exclusion of patients with SIGMAR1_Q2P or COMT_46fs variants and low baseline MMSE score, improved MMSE and ADS-ADL scores at week 57. Daily treatment with ANAVEX2-73 for 57 weeks for the entire Phase 2a cohort had effect sizes of 0.57 and 0.18 for Delta MMSE and Delta ADCS-ADL, respectively, when compared to standard of care (Table 6). If patients with

TABLE 5

| Antecedent X | | Consequent Y | | | | | | | | Fisher Exact Test p-value | Mann-Whitney Wilcoxon p-value |
| --- | --- | --- | --- | --- | --- | --- | --- | --- | --- | --- | --- |
| Variant | $n_x$ | Endpoint | Deriv. | Outcome | Week | $n_y$ | Support | Confidence | Lift | | |
| COMT L146fs | 5 | MMSE | Delta | Worsen | 57 | 12 | 5 | 1.00 | 1.75 | 0.039 | 0.106 |
| COMT L146fs | 5 | ADCS-ADL | Delta | Worsen | 57 | 13 | 5 | 1.00 | 1.62 | 0.063 | 0.007 |
| SIGMAR1 Q2P | 5 | MMSE | Delta | Worsen | 57 | 12 | 5 | 1.00 | 1.75 | 0.039 | 0.081 |
| SIGMAR1 Q2P | 5 | ADCS-ADL | Delta | Worsen | 57 | 13 | 5 | 1.00 | 1.62 | 0.063 | 0.035 |

Figure 3:
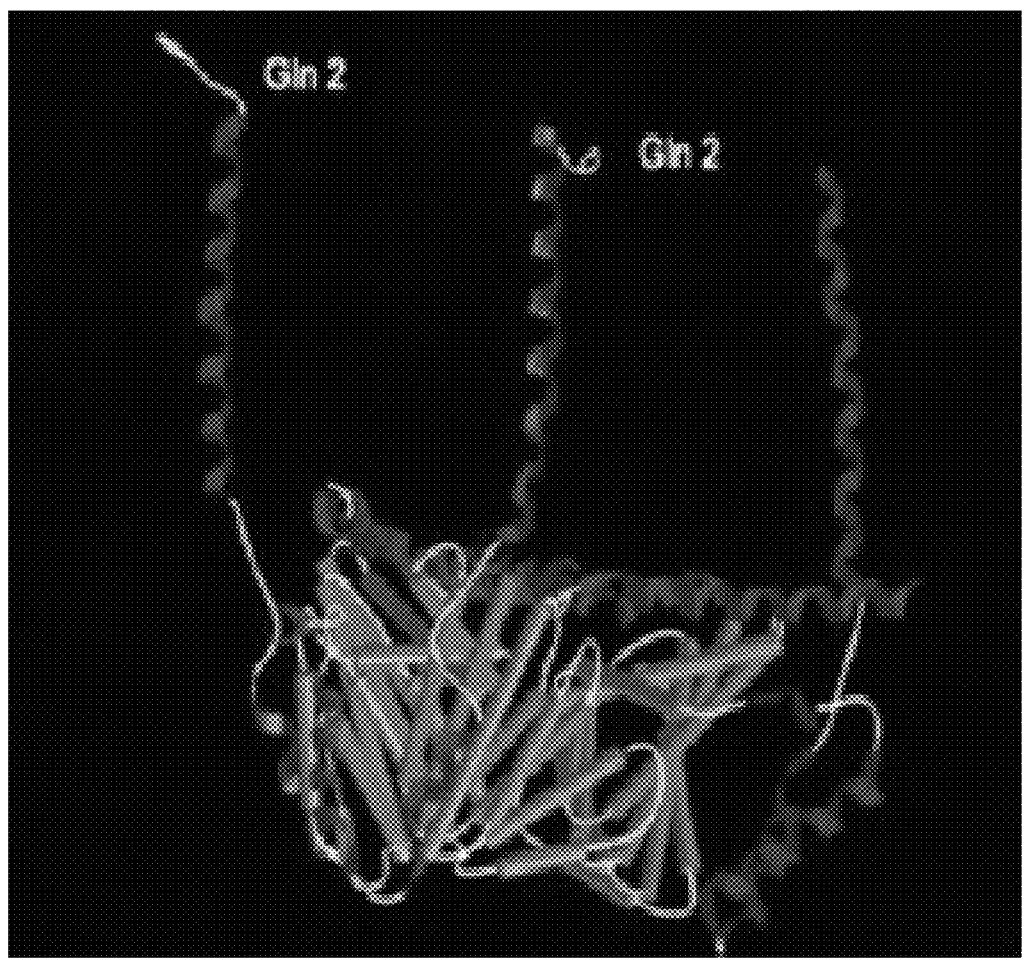
FIG. 3: 3D crystal structure of SIGMAR1 visualized using VistaPDB 1.0 software.

The 3D structural impact of SIGMAR1 Q2P was also investigated. The 3D crystal structure of SIGMAR1 was visualized using VistaPDB 1.0 software (FIG. 3). Each monomer displays an N terminal trans-membrane alpha helix. The N terminus of the protein is believed to face the the SIGMAR1_Q2P and COMT_L146fs variants and low Baseline MMSE score (9 out of 21 patients) were excluded, effect sizes increased to 1.05 and 0.93 for MMSE and ADCS-ADL, respectively (Table 6), both considered 'large' according to Cohen's d guidelines.

TABLE 6

Summary of mean Delta MMSE and mean Delta ADCS-ADL scores at week 57, Cohen's d effect size calculation when compared to standard of care depending on genomic variant status of SIGMAR1_Q2P and COMT_L146fs, and/or baseline MMSE score.

| Subject characteristics | MMSE | | | ADCS-ADL | | |
|---|---|---|---|---|---|---|
| | Mean Δ at 57 weeks | Cohen's d | N (%) | Mean Δ at 57 weeks | Cohen's d | N (%) |
| All | −1.52 ± 4.15 | 0.57* | 21 (100.0%) | −5.19 ± 8.46 | 0.18 | 21 (100.0%) |
| Baseline MMSE ≥20 | −0.15 ± 4.06 | 0.94** | 13 (61.9%) | −2.00 ± 5.93 | 0.66* | 13 (61.9%) |
| Absence of SIGMAR1_Q2P variant | −0.62 ± 4.11 | 0.81** | 16 (76.2%) | −3.31 ± 7.64 | 0.43 | 16 (76.2%) |
| Absence of COMT_L146fs variant | −0.62 ± 4.05 | 0.81** | 16 (76.2%) | −2.37 ± 6.96 | 0.57* | 16 (76.2%) |
| Absence of SIGNAR1_Q2P variant & Baseline MMSE ≥20 | 0.27 ± 4.29 | 1.01** | 11 (52.4%) | −1.27 ± 6.13 | 0.76* | 11 (52.4%) |
| Absence of COMT_L146fs variant & Baseline MMSE ≥20 | 0.18 ± 4.35 | 0.98** | 11 (52.4%) | −0.63 ± 5.33 | 0.89** | 11 (52.4%) |
| Absence of SIGMAR1_Q2P variant & Absence of COMT_L145fs variant & Baseline MMSE ≥20 | 0.50 ± 4.45 | 1.05** | 10 (47.6%) | −0.30 ± 5.50 | 0.93** | 10 (47.6%) |

Example 3. Validation of Results

Figure 4:
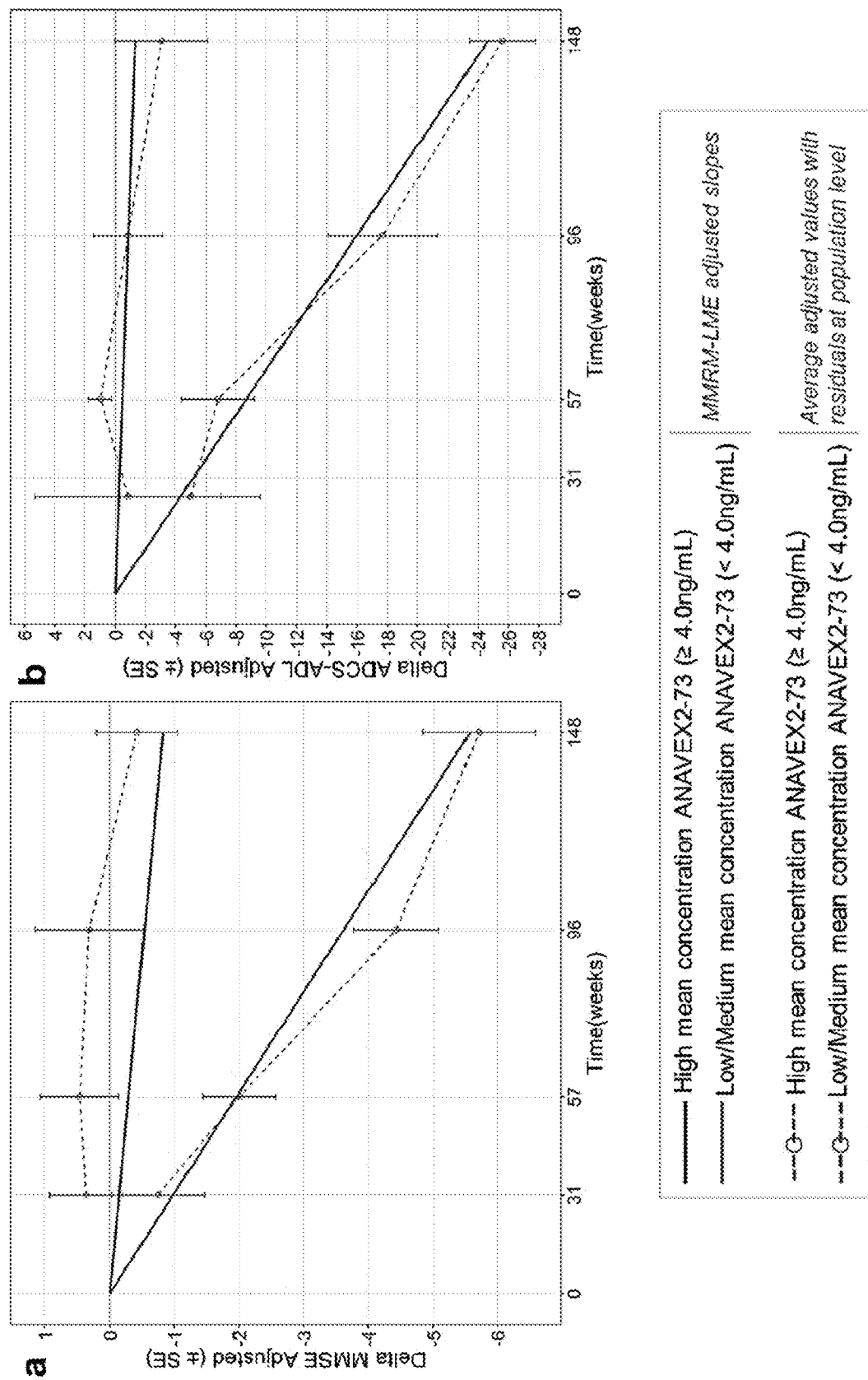
FIGS. 4A-4B. Plots depicting MMRM-LME models of MMSE and ADCS-ADL change from baseline over 148 weeks.
Figure 5:
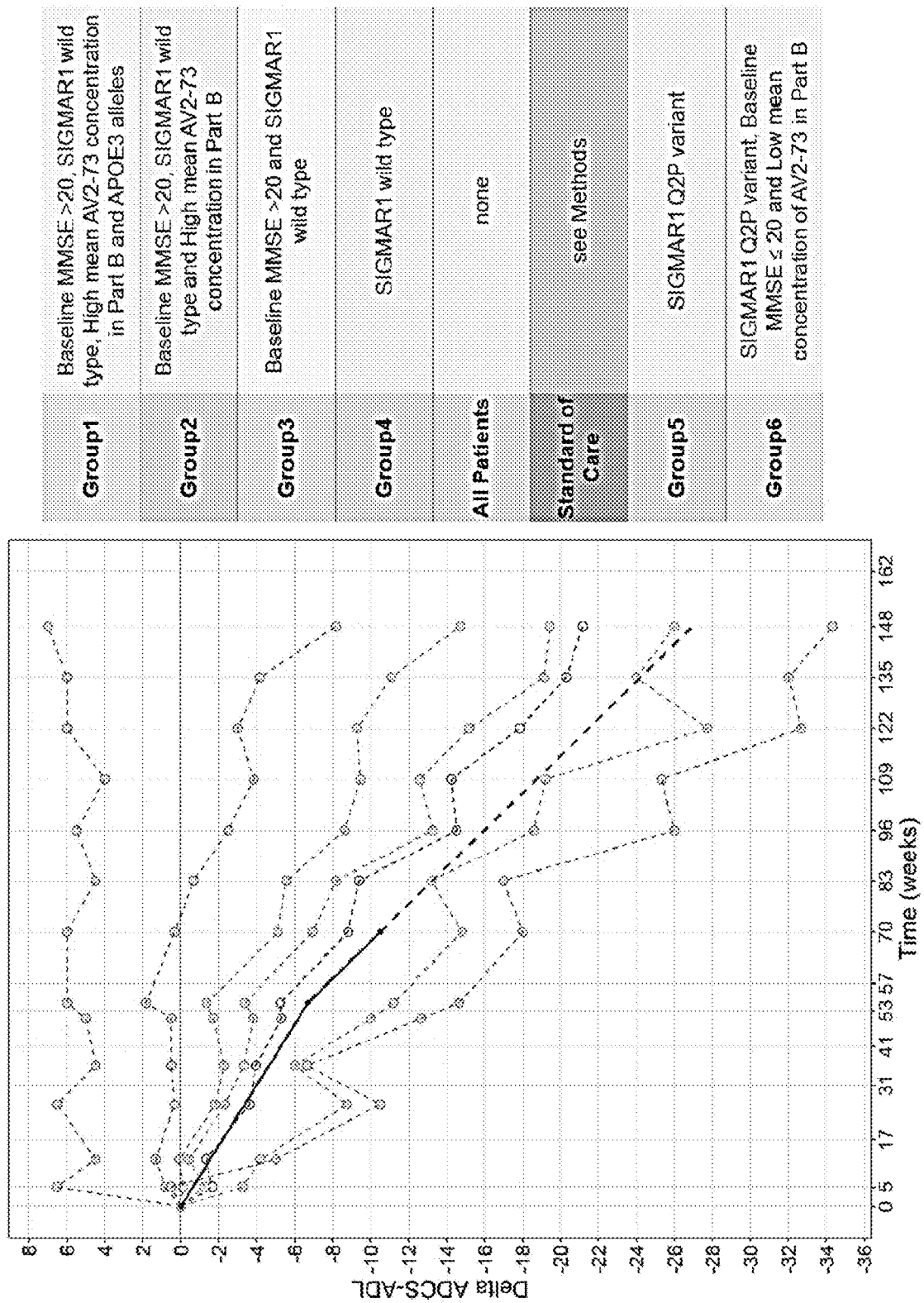
FIG. 5. Plot of unadjusted values of Delta ADCS-ADL over 148 weeks. The plot presents (unadjusted) mean trajectories of Delta ADCS-ADL score through interim 148 weeks of subgroups of patients in the 208-week study depending on biomarker status (absent or present) and of patients given standard of care. The subgroups of patients in the 208-week study are represented (blue, green, orange, pink, purple and turquoise) plot depending on identified biomarker and baseline criteria characteristics.
Figure 6A:
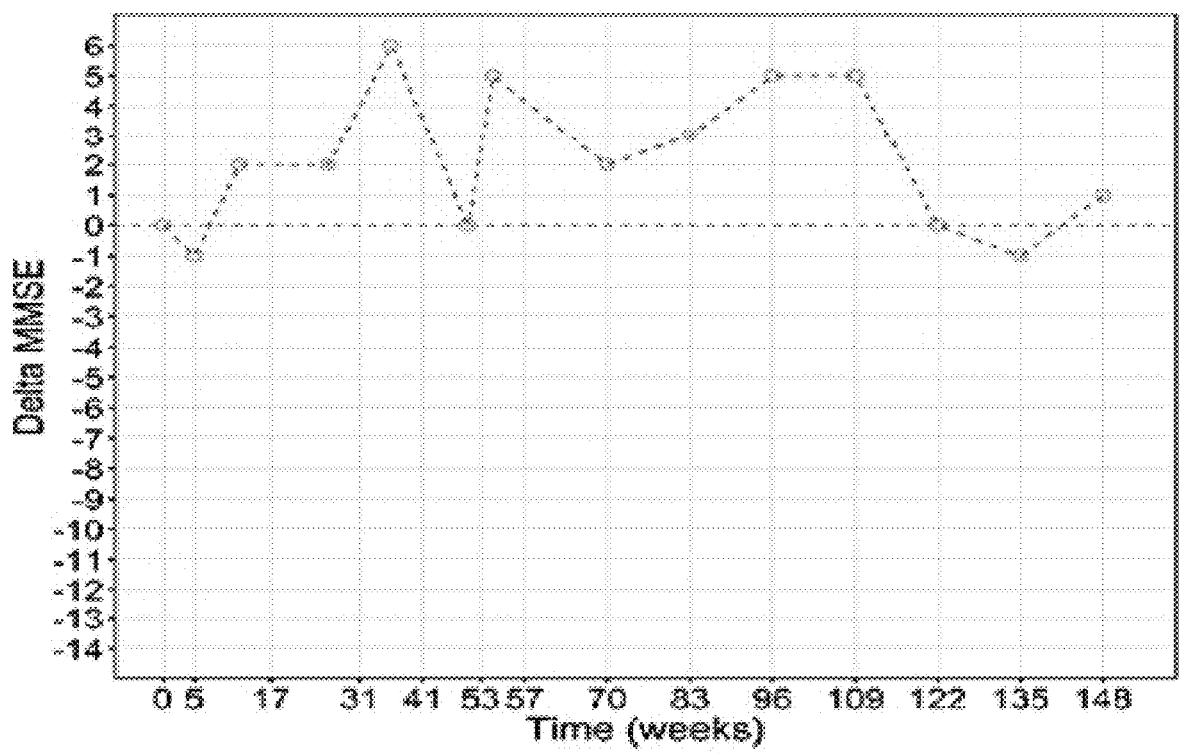
FIGS. 6A-6B. Plots showing the therapeutic response showing Longitudinal Delta MMSE and Delta ADCS-ADL over 148 week of combined studies. The patient presented in FIG. 6A and FIG. 6B has SIGMAR1 gene wild type, mean high concentration levels of ANAVEX2-73 in plasma in Part B and baseline MMSE≥20.
Figure 6A:
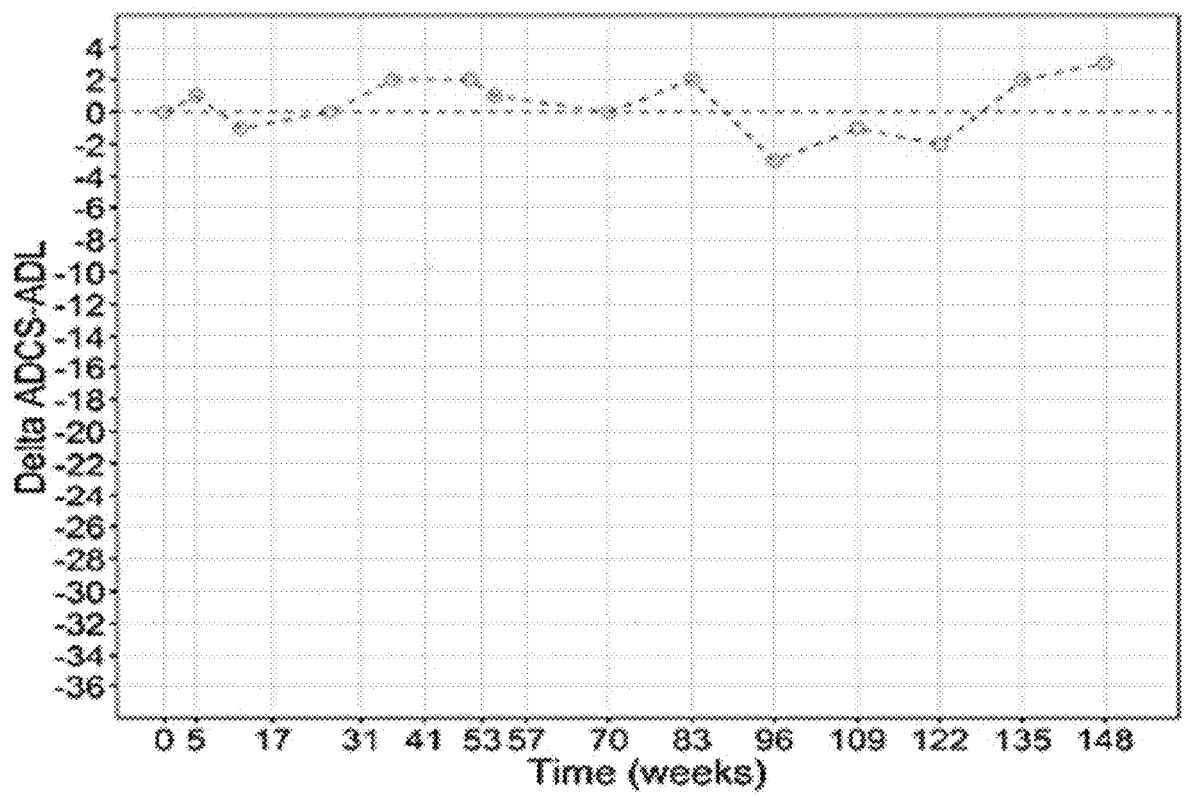
Figure 6B:
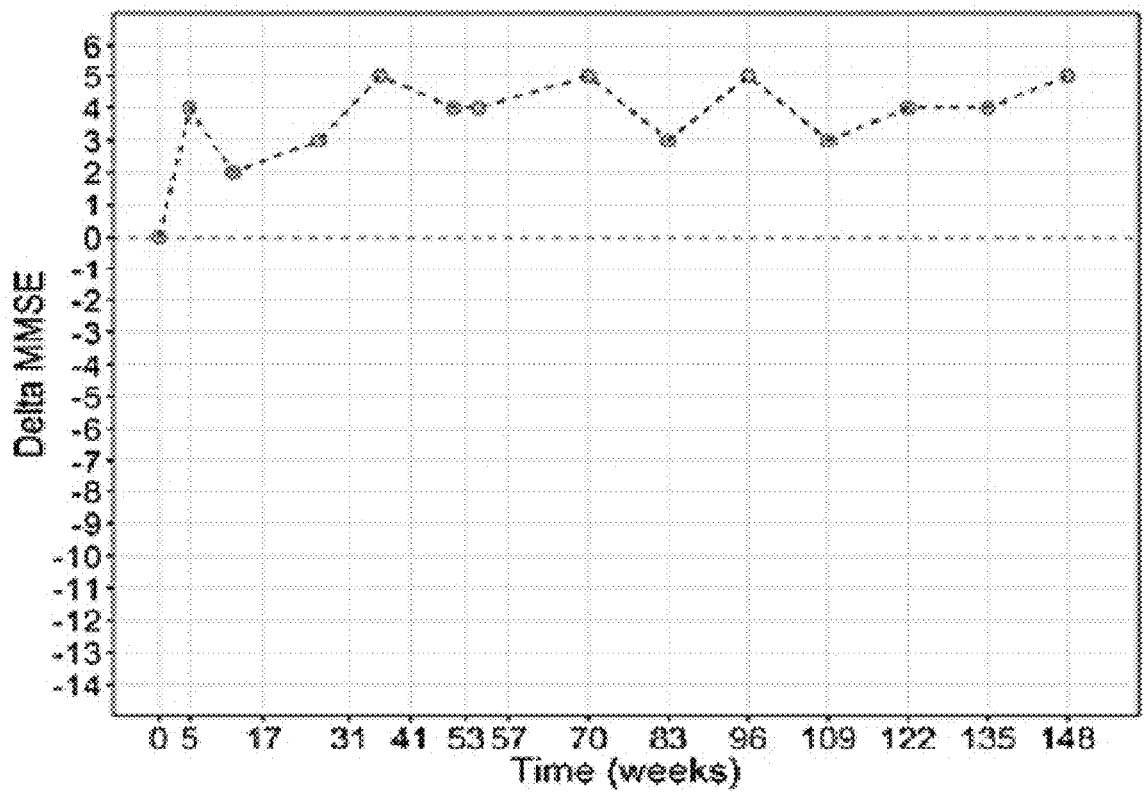
Figure 6B:
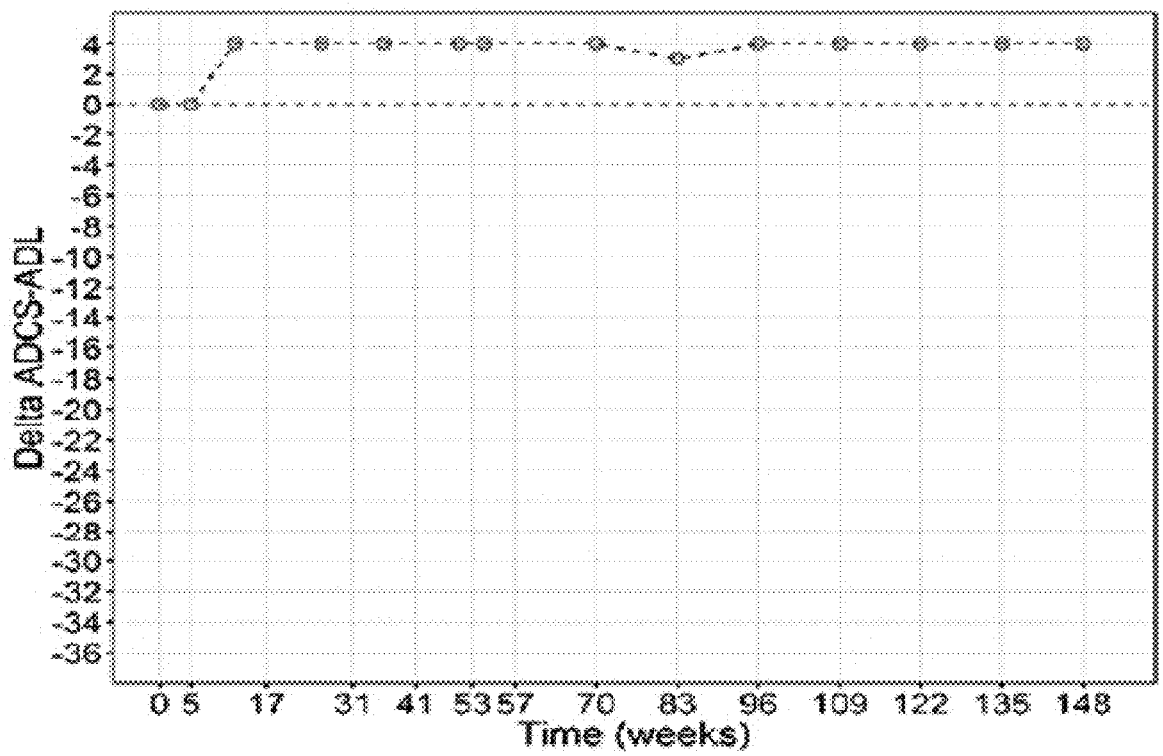

As an internal validation of results at week 57, predictors of response at week 57 were tested with longitudinal data at the interim week 148 in the 208-week study extension study, using regression analyses. This analysis included 21 patients with genomic data and 287 observations for 14 time points (Table 7). ANAVEX2-73 concentration in Part B, identified as predictor of outcome at week 57, was used to define 2 arms for the MMRM-LME model. In addition to parameters identified at week 57 (ANAVEX2-73 concentration levels, Baseline MMSE score, SIGMAR1_Q2P and COMT_L146fs variants), age, sex, APOE E4 status, and donepezil co-medication were included in the MMRM-LME models of Delta MMSE and Delta ADCS-ADL. This analysis showed that the higher ANAVEX2-73 concentration arm had favorable differences of 78% and 88% in adjusted MMSE and adjusted ADCS-ADL, respectively, when compared with the low/medium arm over 148 weeks (p-values<0.0008 and <0.0001, respectively). In addition to time, APOE E4 status (p<0.0001) and ANAVEX2-73 mean concentration were significant predictors (FIGS. 4A-B and Table 8 and Table 6A). Furthermore, SIGMAR1_Q2P, COMT_L146fs, and APOE4 E4 status interactions with time were significant variables. Unadjusted measures corroborated these results; patients with positive biomarkers of response had better Delta ADCS-ADL over 148 weeks than those without the biomarkers or than reference populations receiving standard of care (FIG. 5 and Table 9). Two patients showed exceptional therapeutic response during the longitudinal study (148 weeks period). Both subjects had SIGMAR1 wild type, high mean concentration of ANAVEX2-73 in plasma and baseline MMSE≥20 (FIG. 6). Clinical benefits reported included improvements in mood and alertness and increased independent activity.

TABLE 6A

MMRM-LME model output for Delta ADCS-ADL outcome

| Patient descriptor | P-value (F test) |
|---|---|
| Time | <0.001 |
| AV-2-73 Concentration (=High) | 0.38 |
| Gender (=Male) | 0.535 |
| APOE4 status (=True) | 0.643 |
| Age (=Low) | 0.946 |
| Donepezil treatment (=True) | 0.959 |
| Time: AV2-73 Concentration (=High) | <0.0001 |
| Time: APOE4 status (=True) | <0.0001 |
| AV2-73 Concentration (=High): APOE4 status (=True) | 0.762 |
| Baseline MMSE (=Low) | 0.315 |
| SIGMAR1 Q2P variant (=True) | 0.704 |
| COMT variant (=True) | 0.523 |
| SIGMAR1 variant Q2P (=True): Time | <0.01 |
| COMT variant (=True): Time | <0.01 |
| SIGMAR1 Q2P variant (=True): AV2-73 Concentration (=High) | 0.716 |

TABLE 7

MMRM-LME model output for Delta MMSE outcome

| Patient descriptor | P-value (F test) |
|---|---|
| Time | <0.0001 |
| Age (=Low) | 0.801 |
| Gender (=Male) | 0.146 |
| Baseline MMSE (=Low) | 0.129 |
| APOE4 status (=True) | 0.812 |
| SIGMAR1 Q2P variant (=True) | 0.292 |
| AV2-73 Conc (=High) | 0.726 |
| Time: APOE4 status (=True) | <0.0001 |
| Time: AV2-73 Conc (=High) | <0.0001 |
| SIGMAR1 Q2P variant (=True): AV2-73 Conc (=High) | 0.684 |

TABLE 8

MMRM-LME model output for Delta ADCS-ADL outcome

| Patient descriptor | P-value (F test) |
|---|---|
| Time | <0.001 |
| AV-2-73 Concentration (=High) | 0.38 |
| Gender (=Male) | 0.535 |
| APOE4 status (=True) | 0.643 |
| Age (=Low) | 0.946 |
| Donepezil treatment (=True) | 0.959 |
| Time: AV2-73 Concentration (=High) | <0.0001 |
| Time: APOE4 status (=True) | <0.0001 |
| AV2-73 Concentration (=High): APOE4 status (=True) | 0.762 |
| Baseline MMSE (=Low) | 0.315 |
| SIGMAR1 Q2P variant (=True) | 0.704 |
| COMT variant (=True) | 0.523 |
| SIGMAR1 variant Q2P (=True): Time | <0.01 |
| COMT variant (=True): Time | <0.01 |
| SIGMAR1 Q2P variant (=True): AV2-73 Concentration (=High) | 0.716 |

TABLE 9

Summary of the mean and standard deviations of different patient groups unadjusted change in ADCS-ADL scores at 14 time points (Week 0, 5, 12, 26, 36, 48, 57, 83, 96, 109, 122, 135 and 148). All patients in ANAVEX2-73 study are presented along with each patient subgroup depending on inclusion criteria. The standard of care mean change from baseline for ADCS-ADL scores were obtained from literature with −6.7 point change in one year 42 and −10.5 change in 18 months/70 weeks 43.

| Week | All Patients (N = 21) Mean ± Std. Dev | n | Standard of Care Mean ± Std. Dev | Group1 Mean ± Std. Dev | n | Group2 Mean ± Std. Dev | n |
|---|---|---|---|---|---|---|---|
| 0 | 0 ± 0 | 21 | 0 | 0.00 ± 0.00 | 2 | 0.00 ± 0.00 | 6 |
| 5 | −1.65 ± 6.71 | 20 | −0.64 | 6.50 ± 9.19 | 2 | 0.83 ± 6.59 | 6 |
| 17 | −1.33 ± 3.85 | 21 | −1.55 | 4.50 ± 0.71 | 2 | 1.33 ± 2.80 | 6 |
| 31 | −3.60 ± 8.09 | 20 | −3.35 | 6.50 ± 3.54 | 2 | 0.33 ± 5.39 | 6 |
| 41 | −3.95 ± 6.34 | 21 | −4.64 | 4.50 ± 0.71 | 2 | 0.50 ± 4.09 | 6 |
| 53 | −5.29 ± 7.47 | 21 | −6.18 | 5.00 ± 1.41 | 2 | 0.50 ± 4.18 | 6 |
| 57 | −5.24 ± 8.42 | 21 | −6.70 ± 4.90 | 6.00 ± 2.83 | 2 | 1.83 ± 3.66 | 6 |
| 70 | −8.81 ± 10.90 | 21 | −10.50 | 6.00 ± 2.83 | 2 | 0.33 ± 4.93 | 6 |
| 83 | −9.38 ± 12.69 | 21 | −13.24 | 4.50 ± 2.12 | 2 | −0.67 ± 5.85 | 6 |
| 96 | −14.52 ± 15.61 | 21 | −15.99 | 5.50 ± 2.12 | 2 | −2.50 ± 7.71 | 6 |
| 109 | −14.25 ± 14.56 | 20 | −18.73 | 4.00 ± 0.00 | 2 | −3.83 ± 7.96 | 6 |
| 122 | −17.84 ± 18.89 | 19 | −21.48 | 6.00 ± 2.83 | 2 | −3.00 ± 6.72 | 6 |
| 135 | −20.29 ± 18.37 | 21 | −24.22 | 6.00 ± 2.83 | 2 | −4.17 ± 10.42 | 6 |
| 148 | −21.16 ± 17.73 | 19 | −26.07 ± 18.14 | 7.00 ± 4.24 | 2 | −8.17 ± 15.96 | 6 |

| Week | Group 3 Mean ± Std. Dev | n | Group 4 Mean ± Std. Dev | n | Group 5 Mean ± Std. Dev | n | Group 6 Mean ± Std. Dev | n |
|---|---|---|---|---|---|---|---|---|
| 0 | 0.00 ± 0.00 | 11 | 0.00 ± 0.00 | 16 | 0.00 ± 0.00 | 5 | 0.00 ± 0.00 | 3 |
| 5 | −0.09 ± 6.32 | 11 | −1.25 ± 5.54 | 16 | −3.25 ± 11.30 | 4 | 0.50 ± 9.19 | 2 |
| 17 | 0.09 ± 3.45 | 11 | −0.44 ± 3.42 | 16 | −4.20 ± 4.09 | 5 | −5.00 ± 5.20 | 3 |
| 31 | −1.82 ± 5.71 | 11 | −2.31 ± 6.00 | 16 | −8.75 ± 3.30 | 4 | −10.50 ± 3.54 | 2 |
| 41 | −2.27 ± 6.40 | 11 | −3.31 ± 7.03 | 16 | 6.00 ± 3.00 | 5 | −6.67 ± 4.04 | 3 |
| 53 | −1.73 ± 5.61 | 11 | 3.81 ± 7.24 | 16 | −10.00 ± 6.78 | 5 | −12.67 ± 8.02 | 3 |
| 57 | −1.36 ± 6.09 | 11 | −3.38 ± 7.60 | 16 | −11.20 ± 8.93 | 5 | −14.67 ± 10.50 | 3 |
| 70 | −5.09 ± 10.70 | 11 | −6.94 ± 10.87 | 16 | −14.80 ± 9.63 | 5 | −18.00 ± 12.12 | 3 |
| 83 | −5.55 ± 12.65 | 11 | −8.19 ± 1316 | 16 | −13.20 ± 11.52 | 5 | −17.00 ± 14.11 | 3 |
| 96 | −8.64 ± 16.10 | 11 | −13.25 ± 16.77 | 16 | −18.60 ± 11.67 | 5 | −26.00 ± 8.19 | 3 |
| 109 | −9.45 ± 15.13 | 11 | −12.60 ± 15.00 | 15 | −19.20 ± 13.31 | 5 | 25.33 ± 14.47 | 3 |
| 122 | −9.27 ± 12.17 | 11 | −15.20 ± 17.30 | 15 | −27.75 ± 12.26 | 4 | −32.67 ± 8.96 | 3 |
| 135 | 11.09 ± 16.16 | 11 | −19.12 ± 19.67 | 16 | −24.00 ± 14.65 | 5 | −32.00 ± 13.75 | 3 |
| 148 | −14.73 ± 17.70 | 11 | −19.43 ± 18.50 | 14 | −26.00 ± 16.17 | 5 | −34.33 ± 15.82 | 3 |

Discussion for Examples 1-3

This study is, to the best of our knowledge, the first reported genome-wide search for biomarkers associated with drug response in AD. The approach we used was different from standard classification or searches for "signatures". KEM framework-based FCA was used as a method for identification and ranking of predictors of response by association rules consistent with the clinical studies' data. As shown in this work, the FCA machine learning methodology enabled exploring a very large combinatorial space, typically $10^9$ and larger; extracting smaller sets, typically $2-3 \times 10^6$; and finally focusing on dozens of important relations. In contrast with "black box" numerical methods, this approach allows the identification of patients verifying each identified rule (as shown in Tables 4 and 5) and puts in place objective and explicit filtering strategies to select the most relevant biomarkers.

Negative results generated around the "amyloid hypothesis" have encouraged the AD community to hypothesize that the Aβ plaques may appear at an advanced stage of the disease, which may be beyond the reach of existing anti-BACE or anti-tau interventions. However, characterizing the disease at earlier stages has also been challenging, since reliable genomic markers that may be prognostic of the onset of MCI caused by AD have not yet been identified. APOE status alone does not have sufficient predictive power, because only about 25% of the population carry the APOE4 genotype. Studies have identified a genetic variant, TOMM40 that could be used for the early detection of Mild Cognitive Impairment (MCI). This hypothesis was tested in the TOMORROW study. However, the TOMORROW study including 3,494 patients (out of 24,136 screened) was not able to reach its primary objective of biomarker qualification. In this context, the search for alternative druggable targets for AD is becoming a priority and SIGMAR1 targeted by ANAVEX2-73 may be an important drug target to maintain cellular homeostasis, and which may potentially delay or halt neurodegeneration and even allow compensatory responses.

This paper presents a data-driven, unbiased analysis of data from two clinical studies, which enabled the identification of parameters associated with improved outcome. By searching for and selecting biomarkers that are consistently associated with clinical response over multiple time points and multiple endpoints, a reliable identification and ranking of patient selection markers is possible. It is noteworthy that the approach described in this study, without any a priori hypotheses, identifies in addition to a COMT variant (rs113895332/rs61143203), ANAVEX2-73 mean concentration, baseline MMSE and a specific variant of the SIGMAR1 gene (rs1800866) as the top 20 drivers of clinical response, amongst the >3 million retained subset of rules. Low baseline MMSE is thought to be associated with an AD stage that has progressed beyond the reach of a number of therapeutic approaches. SIGMAR1 is the confirmed in vivo target of ANAVEX2-73. COMT is a gene that has been previously described as involved in memory and other neurobehavioral functions.

The MMRM-LME analysis at interim week 148 showed a significant difference in response between the 2 concentration arms related to adjusted mean Delta ADCS-ADL (88%) and adjusted mean Delta MMSE (78%). It is noted that these differences are significant and quite large. These values compare favorably with recent results obtained in other studies for e.g. data presented at CTAD 2018 for BAN2401 after 72 weeks: 47% in adjusted mean change from baseline in ADAS-Cog and 30% adjusted mean change in ADCOMS54, where about 18% of the changes may be due to the imbalance of the APOE4 status in the respective arms.

An analysis of 39,974 DNA variants (Table 10) showed SIGMAR1_Q2P and COMT_L146fs were retained in the top associations. Due to limited data availability, the standard of care measure of Delta MMSE and Delta ADCS-ADL obtained from the literature to calculate effect size corresponded to 52 weeks instead of 57 weeks, the actual time point used in this study. Finally, the RNA analysis was limited due to collection time (109-135 weeks) and no baseline transcriptome measure was available for comparison. However, an exploratory analysis found that high SIGMAR1 expression was associated with better outcome (Table 11).

TABLE 10

| Number of variants in cluster | Variants | Outcome at Week 57 (Binarized) | Support | Confidence | Lift | Fisher's exact test P-value | $n_x$ | $n_y$ | N |
|---|---|---|---|---|---|---|---|---|---|
| 2 | ALCAM_p.T250M\|<br>ALCAM_p.T301M | ADCSADL High | 6 | 1.00 | 2.63 | 0.0005 | 6 | 8 | 21 |
| 3 | NSD1_p.S457P\|<br>NSD1_p.S623P\|<br>NSD1_p.S726P | ADCSADL High | 5 | 1.00 | 2.63 | 0.0028 | 5 | 8 | 21 |
| 1 | AGPAT4_p.S114R | ADCSADL High | 5 | 1.00 | 2.63 | 0.0028 | 5 | 8 | 21 |
| 3 | ALPL_p.Y186H\|<br>ALPL_p.Y208H\|<br>ALPL_p.Y263H | ADCSADL High | 5 | 1.00 | 2.63 | 0.0028 | 5 | 8 | 21 |
| 4 | CYP4F2_p.W12G\|<br>OR10H4_p.H144R\|<br>OR10H4_p.N100K\|<br>OR10H4_p.T281A | ADCSADL High | 5 | 1.00 | 2.63 | 0.0028 | 5 | 8 | 21 |
| 1 | KRT1_p.K633R | ADCSADL High | 5 | 1.00 | 2.63 | 0.0028 | 5 | 8 | 21 |
| 1 | TRBV7-3_p.A9M | MMSE High | 6 | 1.00 | 2.33 | 0.0015 | 6 | 9 | 21 |
| 4 | PLEKHN1_p.S476P\|<br>PLEKHN1_p.S511P\|<br>PLEKHN1_p.S563P\|<br>PLEKHN1_p.S76P | MMSE High | 6 | 1.00 | 2.33 | 0.0015 | 6 | 9 | 21 |
| 1 | AHNAK2_p.R3076H | MMSE High | 6 | 1.00 | 2.33 | 0.0015 | 6 | 9 | 21 |
| 1 | KDM6B_p.P482S | MMSE High | 5 | 1.00 | 2.33 | 0.0062 | 5 | 9 | 21 |
| 4 | PRAMEF2_p.L73F\|<br>PRAMEF4_p.R270C\|<br>PRAMEF4_p.R419fs\|<br>PRAMEF4_p.V412L | MMSE High | 5 | 1.00 | 2.33 | 0.0062 | 5 | 9 | 21 |
| 1 | USP48_p.S659fs | MMSE High | 5 | 1.00 | 2.33 | 0.0062 | 5 | 9 | 21 |
| 9 | C5orf42_p.F1037C\|<br>C5orf42_p.F1081C\|<br>C5orf42_p.F2033C\|<br>C5orf42_p.F913C\|<br>C5orf42_p.P1794L\|<br>C5orf42_p.P675L\|<br>C5orf42_p.F799L\| | MMSE High | 5 | 1.00 | 2.33 | 0.0062 | 5 | 9 | 21 |

TABLE 10-continued

| Number of variants in cluster | Variants | Outcome at Week 57 (Binarized) | Support | Confidence | Lift | Fisher's exact test P-value | $n_x$ | $n_y$ | N |
|---|---|---|---|---|---|---|---|---|---|
| | C5orf42_p.P842L\| NIPBL_p.N674S | | | | | | | | |
| 2 | TACC3_p.C275Y\| TACC3_p.G287S | MMSE High | 5 | 1.00 | 2.33 | 0.0062 | 5 | 9 | 21 |
| 9 | NUMB_p.G389D\| NUMB_p.G400D\| NUMB_p.G438D\| NUMB_p.G449D\| NUMB_p.G451D\| NUMB_p.G536D\| NUMB_p.G547D\| NUMB_p.G584D\| NUMB_p.G595D | MMSE High | 5 | 1.00 | 2.33 | 0.0062 | 5 | 9 | 21 |
| 1 | ABCB4_p.R652G | MMSE High | 5 | 1.00 | 2.33 | 0.0062 | 5 | 9 | 21 |
| 1 | RERE_p.G123A | MMSE High | 5 | 1.00 | 2.33 | 0.0062 | 5 | 9 | 21 |
| 1 | APOPT1_p.G50S | MMSE Low | 8 | 1.00 | 1.75 | 0.0024 | 8 | 12 | 21 |
| 1 | KLHDC7A_p.R160S | MMSE Low | 7 | 1.00 | 1.75 | 0.0068 | 7 | 12 | 21 |
| 1 | CPPED1_p.A19D | MMSE Low | 7 | 1.00 | 1.75 | 0.0068 | 7 | 12 | 21 |
| 1 | F13A1_p.E652Q | MMSE Low | 7 | 1.00 | 1.75 | 0.0068 | 7 | 12 | 21 |
| 6 | PABPC1_p.R145C\| PABPC1_p.R25C\| PABPC1_p.R2C\| PABPC1_p.R40C\| PABPC1_p.R448C\| PABPC1_p.R493C | MMSE Low | 7 | 1.00 | 1.75 | 0.0068 | 7 | 12 | 21 |
| 7 | PABPC1_p.V169L\| PABPC1_p.V26L\| PABPC1_p.V472L\| PABPC1_p.V485L\| PABPC1_p.V49L\| PABPC1_p.V517L\| PABPC1_p.V64L | MMSE Low | 7 | 1.00 | 1.75 | 0.0068 | 7 | 12 | 21 |
| 1 | PCLO_p.S501P | MMSE Low | 7 | 1.00 | 1.75 | 0.0068 | 7 | 12 | 21 |
| 2 | COL5A3_p.A280P\| COL5A3_p.N226Y | MMSE Low | 7 | 1.00 | 1.75 | 0.0068 | 7 | 12 | 21 |
| 1 | PDXK_p.R81H | MMSE Low | 6 | 1.00 | 1.75 | 0.0170 | 6 | 12 | 21 |
| 1 | SLCO1A2_p.I13T | MMSE Low | 6 | 1.00 | 1.75 | 0.0170 | 6 | 12 | 21 |
| 1 | EFCAB8_p.R7OW | MMSE Low | 6 | 1.00 | 1.75 | 0.0170 | 6 | 12 | 21 |
| 2 | CYP2D6_p.R314H\| CYP2D6_p.R365H | MMSE Low | 6 | 1.00 | 1.75 | 0.0170 | 6 | 12 | 21 |
| 1 | COL21A1_p.E79Q | MMSE Low | 6 | 1.00 | 1.75 | 0.0170 | 6 | 12 | 21 |
| 1 | ERC1_p.S50G | MMSE Low | 6 | 1.00 | 1.75 | 0.0170 | 6 | 12 | 21 |
| 2 | TGM5_p.A270G\| TGM5_p.A352G | MMSE Low | 6 | 1.00 | 1.75 | 0.0170 | 6 | 12 | 21 |
| 3 | ZNF587B_p.V33M\| ZNF587B_p.V82M\| ZNF587B_p.V83M | MMSE Low | 6 | 1.00 | 1.75 | 0.0170 | 6 | 12 | 21 |
| 3 | BDH2_p.N7OS\| LAD1_p.K323E\| LAD1_p.K337E | MMSE Low | 6 | 1.00 | 1.75 | 0.0170 | 6 | 12 | 21 |
| 1 | DLEU1_p.C4S | MMSE Low | 6 | 1.00 | 1.75 | 0.0170 | 6 | 12 | 21 |
| 2 | PRKAG3_p.P46A\| PRKAG3_p.P71A | MMSE Low | 6 | 1.00 | 1.75 | 0.0170 | 6 | 12 | 21 |
| 1 | URB1_p.D63E | MMSE Low | 6 | 1.00 | 1.75 | 0.0170 | 6 | 12 | 21 |
| 1 | AGT_p.T207M | MMSE Low | 6 | 1.00 | 1.75 | 0.0170 | 6 | 12 | 21 |
| 2 | KDM7A_p.R238S\| KDM7A_p.R644S | MMSE Low | 6 | 1.00 | 1.75 | 0.0170 | 6 | 12 | 21 |
| 1 | NPY4R_p.AlaVal275AlaMet | MMSE Low | 6 | 1.00 | 1.75 | 0.0170 | 6 | 12 | 21 |
| 3 | SOGA2_p.D380G\| SOGA2_p.D538G\| SOGA2_p.D898G | MMSE Low | 6 | 1.00 | 1.75 | 0.0170 | 6 | 12 | 21 |
| 1 | ADORA3_p.I248L | MMSE Low | 6 | 1.00 | 1.75 | 0.0170 | 6 | 12 | 21 |
| 1 | BEST4_p.V433L | MMSE Low | 6 | 1.00 | 1.75 | 0.0170 | 6 | 12 | 21 |
| 1 | RNF212_p.Q188* | MMSE Low | 6 | 1.00 | 1.75 | 0.0170 | 6 | 12 | 21 |
| 4 | CAPN10_p.H32V\| CAPN10_p.I39V\| CAPN10_p.I511V\| CAPN10_p.I666V | MMSE Low | 6 | 1.00 | 1.75 | 0.0170 | 6 | 12 | 21 |

TABLE 10-continued

| Number of variants in cluster | Variants | Outcome at Week 57 (Binarized) | Support | Confidence | Lift | Fisher's exact test P-value | $n_x$ | $n_y$ | N |
|---|---|---|---|---|---|---|---|---|---|
| 1 | SLC22A10_p.T474M | MMSE Low | 5 | 1.00 | 1.75 | 0.0389 | 5 | 12 | 21 |
| 1 | IL9_p.T117M | MMSE Low | 5 | 1.00 | 1.75 | 0.0389 | 5 | 12 | 21 |
| 1 | FARP2_p.T260I | MMSE Low | 5 | 1.00 | 1.75 | 0.0389 | 5 | 12 | 21 |
| 1 | HTR3D_p.R90Q | MMSE Low | 5 | 1.00 | 1.75 | 0.0389 | 5 | 12 | 21 |
| 3 | ACACB_p.T1957I\|ACACB_p.T2027I\|ACACB_p.T693I | MMSE Low | 5 | 1.00 | 1.75 | 0.0389 | 5 | 12 | 21 |
| 2 | LY75-CD302_p.K1347R\|LY75_p.K1347R | MMSE Low | 5 | 1.00 | 1.75 | 0.0389 | 5 | 12 | 21 |
| 1 | PAK6_p.M76V | MMSE Low | 5 | 1.00 | 1.75 | 0.0389 | 5 | 12 | 21 |
| 1 | KIAA0556_p.P920L | MMSE Low | 5 | 1.00 | 1.75 | 0.0389 | 5 | 12 | 21 |
| 1 | PVRL4_p.P104T | MMSE Low | 5 | 1.00 | 1.75 | 0.0389 | 5 | 12 | 21 |
| 1 | NDUFS2_p.P352A | MMSE Low | 5 | 1.00 | 1.75 | 0.0389 | 5 | 12 | 21 |
| 2 | HLA-A_p.I306V\|HLA-A_p.K335N | MMSE Low | 5 | 1.00 | 1.75 | 0.0389 | 5 | 12 | 21 |
| 1 | TMC2_p.Q205R | MMSE Low | 5 | 1.00 | 1.75 | 0.0389 | 5 | 12 | 21 |
| 1 | SEL1L2_p.R75C | MMSE Low | 5 | 1.00 | 1.75 | 0.0389 | 5 | 12 | 21 |
| 5 | CYP2C8_p.K297R\|CYP2C8_p.K399R\|CYP2C8_p.R139K\|CYP2C8_p.R37K\|CYP2C8_p.R53K | MMSE Low | 5 | 1.00 | 1.75 | 0.0389 | 5 | 12 | 21 |
| 1 | SIGMAR1_p.Q2P | MMSE Low | 5 | 1.00 | 1.75 | 0.0389 | 5 | 12 | 21 |
| 3 | TTC7A_p.V184L\|TTC7A_p.V504L\|TTC7A_p.V538L | MMSE Low | 5 | 1.00 | 1.75 | 0.0389 | 5 | 12 | 21 |
| 1 | HLA-DQA1_p.I30T | MMSE Low | 5 | 1.00 | 1.75 | 0.0389 | 5 | 12 | 21 |
| 2 | SGOL2_p.I496V\|SGOL2_p.N660S | MMSE Low | 5 | 1.00 | 1.75 | 0.0389 | 5 | 12 | 21 |
| 2 | DNAH11_p.Q639R\|DNAH11_p.S654C | MMSE Low | 5 | 1.00 | 1.75 | 0.0389 | 5 | 12 | 21 |
| 4 | DCLRE1C_p.H123R\|DCLRE1C_p.H128R\|DCLRE1C_p.H243R\|DCLRE1C_p.H97R | MMSE Low | 5 | 1.00 | 1.75 | 0.0389 | 5 | 12 | 21 |
| 1 | COMT_p.L146fs | MMSE Low | 5 | 1.00 | 1.75 | 0.0389 | 5 | 12 | 21 |
| 2 | RP4-576H24.4_p.AspLeu18GluSer\|SIRPB1_p.AspLeu94GluSer | MMSE Low | 5 | 1.00 | 1.75 | 0.0389 | 5 | 12 | 21 |
| 1 | ZC3H3_p.S399G | MMSE Low | 5 | 1.00 | 1.75 | 0.0389 | 5 | 12 | 21 |
| 3 | GAK_p.K1186R\|GAK_p.K1265R\|GAK_p.K420R | MMSE Low | 5 | 1.00 | 1.75 | 0.0389 | 5 | 12 | 21 |
| 3 | PNPLA3_p.C95G\|PNPLA3_p.C99G\|PNPLA3_p.L97R | MMSE Low | 5 | 1.00 | 1.75 | 0.0389 | 5 | 12 | 21 |
| 1 | PCDHGA2_p.F806L | MMSE Low | 5 | 1.00 | 1.75 | 0.0389 | 5 | 12 | 21 |
| 2 | SCARF1_p.G54oS\|SCARF1_p.G626S | MMSE Low | 5 | 1.00 | 1.75 | 0.0389 | 5 | 12 | 21 |
| 1 | C21orf119_p.P10L | MMSE Low | 5 | 1.00 | 1.75 | 0.0389 | 5 | 12 | 21 |
| 4 | LZTFL1_p.D181N\|LZTFL1_p.D229N\|LZTFL1_p.D242N\|LZTFL1_p.D246N | MMSE Low | 5 | 1.00 | 1.75 | 0.0389 | 5 | 12 | 21 |
| 1 | SMCS_p.H682R | MMSE Low | 5 | 1.00 | 1.75 | 0.0389 | 5 | 12 | 21 |
| 3 | LMLN_p.E106D\|LMLN_p.E34D\|LMLN_p.E54D | MMSE Low | 5 | 1.00 | 1.75 | 0.0389 | 5 | 12 | 21 |
| 2 | FOXJ3_p.T343P\|FOXJ3_p.T377P | MMSE Low | 5 | 1.00 | 1.75 | 0.0389 | 5 | 12 | 21 |
| 2 | SVEP1_p.M1421L\|SVEP1_p.M1444L | MMSE Low | 5 | 1.00 | 1.75 | 0.0389 | 5 | 12 | 21 |
| 5 | PABPC1_p.H06T\|PABPC1_p.I1T\|PABPC1_p.I409T\|PABPC1_p.I422T}\|PABPC1_p.I454T | MMSE Low | 5 | 1.00 | 1.75 | 0.0389 | 5 | 12 | 21 |
| 4 | CUL3_p.V20I\|CUL3_p.V501I\|CUL3_p.V543I\|CUL3_p.V567I | MMSE Low | 5 | 1.00 | 1.75 | 0.0389 | 5 | 12 | 21 |
| 2 | RPGRIP1L_p.G1025S\|RPGRIP1L_p.G991S | MMSE Low | 5 | 1.00 | 1.75 | 0.0389 | 5 | 12 | 21 |
| 2 | IL4R_p.S488P\|IL4R_p.S503P | MMSE Low | 5 | 1.00 | 1.75 | 0.0389 | 5 | 12 | 21 |

TABLE 10-continued

| Number of variants in cluster | Variants | Outcome at Week 57 (Binarized) | Support | Confidence | Lift | Fisher's exact test P-value | $n_x$ | $n_y$ | N |
|---|---|---|---|---|---|---|---|---|---|
| 2 | BBX_p.E399del\|TMEM63A_p.L206F | MMSE Low | 5 | 1.00 | 1.75 | 0.0389 | 5 | 12 | 21 |
| 3 | KIAA1522_p.M232V\|KIAA1522_p.M243V\|KIAA1522_p.M291V | MMSE Low | 5 | 1.00 | 1.75 | 0.0389 | 5 | 12 | 21 |
| 2 | TP53BP2_p.Q100K\|TP53BP2_p.Q229K | MMSE Low | 5 | 1.00 | 1.75 | 0.0389 | 5 | 12 | 21 |
| 1 | KIAA1551_p.I59V | MMSE Low | 5 | 1.00 | 1.75 | 0.0389 | 5 | 12 | 21 |
| 1 | PRCC_p.P136S | MMSE Low | 5 | 1.00 | 1.75 | 0.0389 | 5 | 12 | 21 |
| 1 | OR5212_p.L25P | MMSE Low | 5 | 1.00 | 1.75 | 0.0389 | 5 | 12 | 21 |
| 2 | MAVS_p.R218C\|MAVS_p.R77C | MMSE Low | 5 | 1.00 | 1.75 | 0.0389 | 5 | 12 | 21 |
| 2 | OR10H1_p.G16R\|OR10H3_p.S293N | MMSE Low | 5 | 1.00 | 1.75 | 0.0389 | 5 | 12 | 21 |
| 1 | CKAP2L_p.L19F | MMSE Low | 5 | 1.00 | 1.75 | 0.0389 | 5 | 12 | 21 |
| 1 | DMRT3_p.V104A | MMSE Low | 5 | 1.00 | 1.75 | 0.0389 | 5 | 12 | 21 |
| 5 | PAMR1_p.Q431R\|PAMR1_p.Q502R\|PAMR1_p.Q519R\|PAMR1_p.Q542R\|PAMR1_p.Q559R | MMSE Low | 5 | 1.00 | 1.75 | 0.0389 | 5 | 12 | 21 |
| 1 | PRIM2_p.V310G | MMSE Low | 5 | 1.00 | 1.75 | 0.0389 | 5 | 12 | 21 |
| 3 | CPT1B_p.S224C\|CPT1B_p.S393C\|CPT1B_p.S427C | MMSE Low | 5 | 1.00 | 1.75 | 0.0389 | 5 | 12 | 21 |
| 2 | CCDC34_p.N298S\|CCDC34_p.P53S | MMSE Low | 5 | 1.00 | 1.75 | 0.0389 | 5 | 12 | 21 |
| 1 | TRPC6_p.P15S | MMSE Low | 5 | 1.00 | 1.75 | 0.0389 | 5 | 12 | 21 |
| 2 | N4BP2L2_p.N529S\|N4BP2L2_p.N544S | MMSE Low | 5 | 1.00 | 1.75 | 0.0389 | 5 | 12 | 21 |

TABLE 11

Association rules linking SIGMAR1 RNA expression with MMSE and ADCS-ADL endpoints between weeks 57 and 148. Highlighted in blue are time points when blood was collected for RNA expression analysis.

| Antecedent X RNA expression | Consequent Y | | | | Support | Confidence | Lift | Fisher Exact Test P-Value | Mann-Whitney-Wilcoxon P-value | $n_x$ | $n_y$ |
|---|---|---|---|---|---|---|---|---|---|---|---|
| | Endpoint | Deriv. | Outcome | Week | | | | | | | |
| High SIGMAR1 | ADCS-ADL | Slope | Improve | 57 | 4 | 0.57 | 2.4 | 0.025 | 0.067 | 7 | 5 |
| High SIGMAR1 | ADCS-ADL | Delta | Improve | 57 | 5 | 0.71 | 1.88 | 0.041 | 0.067 | 7 | 8 |
| High SIGMAR1 | ADCS-ADL | Delta | Improve | 57 | 5 | 0.71 | 1.88 | 0.041 | 0.067 | 7 | 8 |
| High SIGMAR1 | ADCS-ADL | Delta | Improve | 70 | 5 | 0.71 | 1.5 | 0.14 | 0.036 | 7 | 10 |
| High SIGMAR1 | ADCS-ADL | Delta | Improve | 83 | 5 | 0.71 | 1.67 | 0.08 | 0.025 | 7 | 9 |
| High SIGMAR1 | MMSE | Delta | Improve | 83 | 5 | 0.71 | 1.88 | 0.041 | 0.036 | 7 | 8 |
| High SIGMAR1 | ADCS-ADL | Delta | Improve | 96 | 5 | 0.71 | 2.14 | 0.017 | 0.011 | 7 | 7 |
| High SIGMAR1 | ADCS-ADL | Delta | Improve | 109 | 4 | 0.57 | 1.9 | 0.078 | 0.032 | 7 | 6 |
| High SIGMAR1 | MMSE | Delta | Improve | 122 | 4 | 0.67 | 1.81 | 0.095 | 0.034 | 6 | 7 |
| High SIGMAR1 | MMSE | Delta | Improve | 135 | 5 | 0.71 | 1.88 | 0.041 | 0.033 | 7 | 8 |
| High SIGMAR1 | MMSE | Delta | Improve | 148 | 4 | 0.67 | 1.81 | 0.095 | 0.039 | 6 | 7 |

$n_x$: number of antecedent (patients in RNA expression group) observations
$n_y$: number of consequent (Endpoint) observations
Deriv.: Calculation used for derived endpoint descriptor The methodology that has been described in this work opens the possibility of using data-driven unbiased biomarker identification early in the drug development process. The "white box" and systematic approach of Formal Concept Analysis may be an ideal match for the analysis of early data, where a machine learning platform may explain each finding and be essential for identifying and ranking patient selection biomarkers for therapeutic response. These data analytic methods could become cornerstones for precision medicine drug discovery and development.

Methods for Examples 1-3

(a) Study Design

The present study integrates and analyzes data and samples from two consecutive clinical trials: 57-week study and 208-week study. 57-week study was a multicenter Phase 2a clinical trial of the drug ANAVEX2-73 that recruited a sample of 32 subjects with mild-to-moderate AD. It consisted of two parts: Part A was a simple randomized, open-label, two-period, cross-over, adaptive trial lasting up to 5 weeks. Each period involved one specific administration route and two possible dose levels: in one period the oral dose (30 mg or 50 mg) was administrated and in the other period an intravenous (IV) form (3 mg or 5 mg) was administered, making a total of 8 possible dose administration schemes in Part A (details available in FIG. 2A). The two periods were separated by a wash-out period of 12 days where no dose was given.

Part B, following immediately after Part A, was an open-label extension of the oral daily dose for an additional 52 weeks. The primary endpoint of 57-week study was to establish the safety and tolerability of the drug. Secondary endpoints aimed at establishing the relationship between dosing regimen and pharmacodynamics-exploratory efficacy outcomes of cognition and function. Cognition was assessed by the Mini Mental State Examination (MMSE), while functional abilities by the Alzheimer's Disease Co-operative Study—Activities of Daily Living Inventory (ADCS-ADL). Additional cognitive measures included the Cogstate Brief Battery (CBB), and functional measures of Electroencephalography and Event-Related Potential (EEG and ERP). Part B continued an adaptive oral administration scheme. Table 12 summarizes mean oral dose administration during the 57-week study study.

TABLE 12

Summary statistics and binning thresholds of ANAVEX2-73 mean dose administration in mg at three different time periods: Part A1 (Day 1-2: within 2 days of first oral dose), Part A2 (Day 3-12: after the first two days of first oral dose and before beginning of Part B) and Part B (Week 5 to Week 57). (N = 32 patients).

| | | Mean Dose (mg) | | |
|---|---|---|---|---|
| | | Part A1 | Part A2 | Part B |
| | Min | 10 | 10 | 9.3 |
| | Max | 50 | 50 | 50 |
| | Mean | 38.12 | 30.4 | 21.68 |
| | Std. dev | 10.81 | 9.91 | 11.11 |
| | No. missings | 0 | 0 | 2 |
| Low group | Thr. n | [10, 30] 17 | [10, 25.5] 11 | [9.30, 11) 10 |
| Medium group | Thr. n | / / | (25.5, 30] 11 | [11, 30] 10 |
| High group | Thr. n | (30, 50] 15 | (30, 50] 10 | (30, 50] 10 |

Due to favorable safety and tolerability profile of the 57-week study (Table 2), and in response to requests from patients and caregivers, a 208-week open-label extension study (208-week study) was carried out immediately after completion of 57-week study Part B. 208-week study enrolled the 24 subjects who completed Part B and applied similarly an adaptive daily oral administration scheme. ANAVEX2-73-003 involves continuous evaluation of safety and efficacy as measured by the MMSE and ADCS-ADL. At week 148 (interim time point for analyses), data on the subjects remaining in the study (n=21) was analyzed for efficacy outcomes. This report was drafted using data available at week 148, while ANAVEX2-73-003 is still ongoing.

(b) Subjects

A total of 32 subjects with mild to moderate AD, between 50 and 85 years of age, were enrolled across three sites in Australia from December 2014 through September 2015. Their diagnoses were consistent with Diagnostic and Statistical Manual of Mental Disorders 4th edition (DSM-IV) and National Institute of Neurological and Communicative Disorders and Stroke/Alzheimer's Disease and Related Disorders Association criteria, and included evaluation of MRI and/or CT brain scans. The demographics and baseline characteristics of the 32 participants are summarized in Table 3 along with the group of participating subjects with genomic data collected after protocol amendment and patients consent (N=21). Table 2 presents patient disposition. Seven patients discontinued during the 57-week 57-week study study, thereof six were withdrawal of consent and one due to an Adverse Event (AE). And a total of three patients discontinued during 208-week study up to cumulative 148 interim week of the on-going extension study.

The following assessment scores and criteria were recorded at baseline and at each visit: MMSE, ADCS-ADL, Hamilton Depression Rating Scale (HAM-D) assessment, Rosen Modified Hachinski Ischemic Score (RmHis), CBB, and EEG/ERP. CBB subtests consisted of six different sub-scores: Detection (DET; Processing Speed), Identification (IDN; AttentionNigilance), One-Card-Learning (OCL; Visual Recognition Memory), One-Back (OBK; Working Memory), International Shopping List (ISLT; Verbal Learning), and International Shopping List delayed recall (ISRL; Verbal Memory).

(c) Study Endpoints

A. Safety Endpoints

Safety was evaluated by assessment of incidence and severity of adverse events, vital signs, physical examination, clinical laboratory parameters (hematology, serum chemistry and urinalysis), and electrocardiogram (data not shown).

B. Efficacy Outcomes

Exploratory clinical efficacy in this study was defined as change from baseline of each patient's cognitive (MMSE) and functional ability (ADCS-ADL) scores. The MMSE57 is a widely used, validated instrument in clinical AD research, including as a cognitive outcome measure in drug trials. The range of the scale is from 0 to 30, with a higher score indicating higher cognitive function. The ADCS-ADL58 is undertaken in a structured caregiver interview format and assesses performance in activities of daily living of patients with AD. The scale is from 0 to 78, with a higher score indicating greater function. The ADCS-ADL has shown to have good test-retest reliability 59. The MMSE and the ADCS-ADL were assessed during pre-specified clinical site visits across 14 different time points during the 57-week study (Weeks 0 and 5 in Part A; Weeks 17, 31, 41, 53, and 57 in Part B), and 208-week study (Weeks 70, 83, 96, 109, 122, 135, and 148) studies.

Corresponding Delta scores were calculated using the difference between values at each visit and at baseline for each individual patient, with a focus on Week 57. In addition, to lower the impact of noise in MMSE and ADCS-ADL scores, a Slope was estimated using a linear regression across all available time points for each individual patient. The derived scores describe the progression of exploratory efficacy data from baseline at several specific time points (Deltas) and over a set period of time (Slope). Including sub-scores and derived measures from the same test score did not have an impact on the analytical method applied in this study since it treated and described each relationship independently.

Table 13 summarize Delta scores, with respect to baseline, for the MMSE and the ADCS-ADL at 13 time points in 57-week study (Weeks 5, 12, 26, 36, 48, and 57) and in ANAVEX2-73-003 (Weeks 70, 83, 96, 109, 122, 135, and 148). Summary statistics of Slopes for MMSE and ADCS-ADL are illustrated in Table 13.

TABLE 13

| Patient baseline characteristic | Low group Threshold | Low group Count | High group Threshold | High group Count |
|---|---|---|---|---|
| Age | ≤70 | 16 | >70 | 16 |
| BMI | ≤25 | 13 | >25 | 19 |
| Diastolic Blood Pressure | ≤84 | 22 | >84 | 10 |
| Systolic Blood Pressure | ≤149 | 24 | >149 | 8 |
| Heart Rate | ≤74 | 28 | >74 | 4 |
| Respiration Rate | ≤15 | 28 | >15 | 4 |
| Pulse Oximetry | ≤96 | 3 | >96 | 26 |
| Body Temperature | ≤36.3 | 14 | >36.3 | 18 |

C. Pharmacokinetics

A pharmacokinetics analysis was performed during Part A only. Blood samples were drawn at 12 and 11 time points after the first oral or IV administration during the first and second periods of Part A, respectively. Pharmacokinetic parameters included in the analysis consisted of maximum plasma drug concentration ($C_{max}$), time to maximum plasma concentration during a dosing interval ($t_{max}$), area under the curve from the time of dosing to the last measurable concentration ($AUC_{0-t}$), mean elimination half-life ($t_{1/2}$), and the total body clearance for extravascular administration divided by the fraction of dose absorbed (CL/F). FIG. 2b shows $AUC_{0-inf}$ after first administration (24 first hours).

Steady-state plasma levels of ANAVEX2-73 and its metabolite ANAVEX19-144 were assessed in Part B through blood samples collection at pre-specified time points (Weeks 12, 26, 36 and 48). Mean concentration values in ng/mL of each patient were then averaged. Table 14 illustrates mean plasma concentrations of ANAVEX2-73 and its metabolite ANAVEX19-144 during the 57-week study study.

TABLE 14

Summary statistics and binning thresholds of plasma concentrations of ANAVEX2-73 and its metabolite ANAVEX 19-144 at three time periods: Part A1 (Day 1-2: within 2 days of first oral dose), Part A2 (Day 3-12: after the first two days of first oral dose and before beginning of Part B) and Part B (Week 5 to Week 57). (N = 32 patients).

| | | Mean Concentration ANAVEX2-73 (ng/ML) | | | Mean Concentration ANAVEX19-144 (ng/ml) | | |
|---|---|---|---|---|---|---|---|
| | | Part A1 | Part A2 | Part B | PartA1 | Part A2 | Part B |
| | Min | 0.84 | 0.03 | 0 | 8.03 | 2.55 | 1.38 |
| | Max | 15.9 | 8.44 | 11.58 | 31.61 | 68.55 | 43.2 |
| | Mean | 5.25 | 2.11 | 3.8 | 16.79 | 19.7 | 30.78 |
| | Std. riev | 4.04 | 1.75 | 3.2 | 6.7 | 14.4 | 12.13 |
| | No. missings | 0 | 0 | 5 | 0 | 0 | 5 |
| Low | Thr. | [0.84, 2.92] | [0.026, 0.90] | [0, 2.06] | [8.03, 12.0] | [2.55, 12.4] | [1.38, 10.8] |
| group | n | 11 | 11 | 9 | 11 | 11 | 9 |
| Medium | Thr. | (2.92, 5.32] | (0.99, 2.58] | (2.06, 3.90] | (12.0, 18.5] | (12.4, 20.9] | (10.8, 27.7] |
| group | n | 11 | 11 | 9 | 11 | 11 | 9 |
| High | Thr. | [5.32, 15.9] | (2.58, 8.44] | (3.90, 11.6] | (18.5, 31.6] | (20.9, 68.5] | (27.7, 43.3] |
| group | n | 10 | 10 | 9 | 10 | 10 | 9 |

The relationship between dose and plasma concentration of ANAVEX2-73 was assessed during a Phase 1 study[22], and can be assumed to be linear in the 1-60 mg range in male healthy subjects. The aforementioned dose-dependent increase of plasma concentration of ANAVEX2-73 and metabolite has been also observed in the present study, as illustrated in FIG. 2B.

D. DNA and RNA Extraction and Sequencing

Blood samples were collected from all still participating 21 subjects, between weeks 103-135, depending on the visit date after protocol amendment and approval and patients consent during the ANAVEX2-73-003 extension study. These samples enabled DNA (Whole Exome) and RNA Next Generation Sequencing (NGS) data analysis. 408,551 DNA variants were identified within the cohort. Of these, 39,974 high or moderate impact variants driving an amino acid modification in the protein were kept, RNA expression values were normalized as Transcripts Per Kilobase Million (TPM).

E. Focused Gene Subset 243 genes were selected from the 27,155 mapped sequences obtained from NGS analysis introduced above (FIGS. 10A-C). 102 genes were selected on the basis of their involvement in neurodegenerative diseases (FIG. 10A). 20 genes were selected as part of a SIGMAR1's functional interactome (FIGS. 10C-D), based on a confidence score of 0.150 obtained from the STRING database (January 2018). Moreover, 113 genes of the cytochrome P450s gene family and 10 genes from the methyltransferase gene family were also added (FIG. 10B).

F. Data Analysis

A data analysis using association rule-based FCA was performed to identify markers of response to treatment at week 57. In a subsequent step, confirmatory analyses of identified markers of response at 148 weeks was performed using linear mixed effects. FIG. 1B illustrates the different types of data used in the analyses, whereas FIG. 1C displays the two different types of analyses for identification and validation of markers of drug response.

(d) Association Rules and the KEM® Platform

The KEM® (Knowledge Extraction and Management) v 3.6.2 software was used to systematically extract relations between all variables collected. Based on Galois lattices theory, or Formal Concept Analysis (FCA), KEM® identifies groups of objects with shared properties and generates corresponding association rules. Association rules have been developed to detect patterns and relationships in large heterogeneous databases. This methodology was introduced by Agrawal and Sirikant and it has been successfully used in different domains including: market basket analysis, drug discovery, and genomic characterization of complex diseases. The method has also been successfully used in drug efficacy and patient stratification studies. Association rules may reflect the presence of a causal relationship between two variables. However, the presence of a statistically significant association is neither necessary nor sufficient to indicate the presence of such causal relationships. Hence, the use of the quality measures described below.

An association rule is an implication such as X→Y, with X being the antecedent (or a combination of antecedents, also termed left side) and Y the consequent (or combination of consequents; also termed right side) of the rule, that allows inferring X as an explanation of Y. Considering a dataset composed of N patients, $n_X$, $n_Y$ and $n_{XY}$, respectively are the numbers of patients satisfying the antecedent(s) X of a rule, the consequent(s) Y and both parts of the rule, respectively. For any given rule, it is possible to identify specifically the $n_{xy}$ patients matching this rule.

Six main quality measures are used to describe and rank association rules, namely: Support, Confidence, Lift, two P-values measures of significance and Cohen's d a measure of effect size.

i. Support, Confidence, and Lift

Support is defined as the number of subjects for which the association has been observed:

$$\text{Support}(X \rightarrow Y) = n_{XY}$$

Confidence is defined as the percentage of the characterized patients verifying the rule:

$$\text{Confidence}(X \rightarrow Y) = \frac{n_{XY}}{n_X}$$

The Lift (relative probability) is the ratio of observed support to that expected if X and Y were independent. It measures the performance of a rule to identify a subgroup from a larger population:

$$\text{Lift}(X \rightarrow Y) = \frac{N \times n_{XY}}{n_X \times n_y}$$

ii. Significance Tests

P-values from two statistical tests were calculated for each association rule. A right-sided Fisher's exact test to account for the relationship of the rule, for categorical data and suitable for small sample sizes. And a two-sided Mann-Whitney U test, for comparing continuous outcome measures per descriptor group. Statistical significance was judged for both tests at a level of 0.05.

iii. Effect Size

Cohen's d index is calculated for each association to quantify the effect size, from which the number of patients to be included to determine a significant relationship in future studies can be calculated. Cohen's d indicates the standardized difference between two population means.

In this study, the outcomes were defined by Delta and Slope values of MMSE and ADCS-ADL. Control group values for calculating effect size were obtained combining trial results available in the AD literature receiving standard of care: the control group mean Delta MMSE at 52 weeks was defined as −3.7 with a standard deviation of 3.5, and mean Delta ADCS-ADL at 52 weeks was −6.7 with a standard deviation of 8.0.

Continuous variables such as age were discretized using distribution (see summary of thresholds in Table 13). For instance, MMSE at baseline was discretized in two groups, 'Low' (defined as baseline MMSE<20) and 'High' (defined as baseline MMSE>20). It is noted that the value "20" is not a predefined limit: MMSE baseline score threshold "<20" corresponded to the median of the observed values of all included patients.

(e) Linear Mixed Effect Models

Application of Mixed effect Models for Repeated Measures (MMRM) to model continuous primary endpoints in longitudinal clinical trials and specifically to analyze the outcome of AD clinical studies has become common practice.

The longitudinal relevance of biomarkers identified at week 57 was assessed at week 148 using MMRM, by allocating subjects to one of two arms (High versus Low/Medium) based on ANAVEX2-73 mean blood concentration in Part B. Given the small cohort size, time was treated as a continuous variable in the analyses to avoid over-parameterization and improve robustness. Therefore, a linear component for mixed-effect models (LME) was applied to model time. MMRM-LME, as implemented in R statistical software, was applied to model Delta MMSE and ADCS-ADL scores with ANAVEX2-73 concentration levels over time as well as other identified descriptors of response.

Example 4. DNA & RNA Extraction and Analysis

A total of 27,155 annotated genomic locations corresponding to genes were identified in AD patient sequences, including 616 pathways. An initial panel of 243 genes were defined. The panel consisted of 102 genes implicated in neurodegenerative diseases, 20 genes connected with the SIGMAR1 functional interactome and 12 methyltransferases genes and 111 CYP genes linked to drug metabolism (Table 15).

TABLE 15

| Neuro-degenerative diseases panel | CYP's & Methyl transferases | SIGMAR 1 functional interactions |
|---|---|---|
| ABCA7 | CYP1A1 | CYP51A1 |
| ADAMT59 | CYP1A2 | C14orl1 |
| Aff3 | CYP1B1 | MSMO1 |
| AMT | SYP1D1P | SLC5A7 |
| APOE | CYP11A1 | SOLE |
| APP | CYP11B1 | LBR |
| ARFGEF2 | CYP11B2 | TM75F2 |
| ARMT | CYP17A1 | H5D387 |
| BCA7 | CYP19A1 | CSorl4 |
| BCHE | CYP2A13 | KCNA4 |
| BCL11A | CYP2AG | 5DR42E2 |
| BDNF | CYP2A7 | 5DR42EI |

TABLE 15-continued

| Neuro-degenerative diseases panel | CYP's & Methyl transferases | SIGMAR 1 functional interactions |
|---|---|---|
| BIN1 | CYP2A7P1 | DHCR7 |
| C12orf65 | CYP2AB1P | H5D381 |
| CASS4 | CYP2AC1P | H5D382 |
| CD2AP | CYP2B6 | N5DHL |
| CD33 | CYP2B7P | CH25H |
| CELF1 | CYP2C115P | ITPR3 |
| CHN1 | CYP2C18 | PLEKHG5 |
| CLN3 | CYP2C19 | KCNH5 |
| CLOCK | CYP2C23P | |
| CLU | CYP2C56P | |
| CNTN1 | CYP2C58P | |
| COMT | CYP2C59P | |
| CR1 | CYP2C60P | |
| CRY1 | CYP2C61P | |
| CRY2 | CYP2C63P | |
| CTNNBL1 | CYP2C64P | |
| DAG1 | CYP2C8 | |
| DPYD | CYP2C9 | |
| D5G2 | CYP206 | |
| DTNBP1 | CYP207 | |
| EPHA1 | CYP208P | |
| ERCCB | CYP2E1 | |
| FERMT2 | CYP2F1 | |
| FMR1 | CYP2F2P | |
| FOXP1 | CYP2G1P | |
| FRM04A | CYP2G2P | |
| GBA | CYP2J2 | |
| GCKR | CYP2R1 | |
| GMPPB | CYP251 | |
| GRIN2B | CYP2T1P | |
| HLA-DRB1 | CYP2T3P | |
| HLA-DRB4 | CYP2U1 | |
| IFNG | CYP2W1 | |
| IL10 | CYP20A1 | |
| IL17A | CYP21A1P | |
| IL18 | CYP21A2 | |
| INPPSD | CYP24A1 | |
| KANSL1 | CYP26A1 | |
| KCNH1 | CYP26B1 | |
| KMT2D | CYP26C1 | |
| LARGE1 | CYP27A1 | |
| LRRK2 | CYP27B1 | |
| MAPT | CYP27C1 | |
| MOH1 | CYP3A137P | |
| MEF2C | CYP3A4 | |
| M54MA | CYP3A43 | |
| M54A4E | CYP3A5 | |
| M54AGE | CYP3A51P | |
| MTUS1 | CYP3A52P | |
| NFKK | CYP3A54P | |
| NME8 | CYP3A7 | |
| NPAS2 | CYP39A1 | |
| NR1D1 | CYP4A11 | |
| PCP4 | CYP4A22 | |
| PDE4D | CYP4A26P | |
| PDE7A | CYP4A27P | |
| PER1 | CYP4A43P | |
| PER2 | CYP4A44P | |
| PER3 | CYP4B1 | |
| PICALM | CYP4F10P | |
| PLD3 | CYP4F11 | |
| PPARG | CYP4F12 | |
| PSEN1 | CYP4F2 | |
| PSEN2 | CYP4F22 | |
| PTK2B | CYP4F23P | |
| RAB10 | CYP4F24P | |
| REST | CYP4F25P | |
| RIN3 | CYP4F26P | |
| RDRA | CYP4F27P | |
| RDRA | CYP4F29P | |
| RDRB | CYP4F3 | |
| RTN1 | CYP4F30P | |
| SHANK3 | CYP4F31P | |
| SIGMAR1 | CYP4F32P | |
| SLC14A1 | CYP4F33P | |
| SLC24A4 | CYP4F34P | |
| SNAP25 | CYP4F35P | |
| SNCA | CYP4F36P | |
| SORL1 | CYP4F44P | |
| SRRM4 | CYP4F45P | |
| ST3GAL3 | CYP4F59P | |
| SUOX | CYP4F60P | |
| TCF4 | CYP4F61P | |
| THRB | CYP4F62P | |
| TOMM40 | CYP4F8 | |
| TREM2 | CYP4F9P | |
| UBA7 | CYP4V2 | |
| UBDLN1 | CYP4X1 | |
| VSNL1 | CYP4Z1 | |
| ZCWPWI | CYP422P | |
| ZNF224 | CYP46A1 | |
| | CYP46A4P | |
| | TBXA51 | |
| | CYP51A1 | |
| | CYP51A1P1 | |
| | CYP51A1P2 | |
| | CYP51A1P3 | |
| | CYP7A1 | |
| | CYP7B1 | |
| | PTGIS | |
| | CYP8B1 | |
| | A53MT | |
| | ASMT | |
| | COMT | |
| | GAMT | |
| | GNMT | |
| | HNMT | |
| | INMT | |
| | NNMT | |
| | PNMT | |
| | TPMT | |
| | SIGMAR1 | |

A distribution analysis was performed using TPM (Transcripts Per kilobase Million) values for each RNA gene expression, defining 3 equal size bins: Low, Medium, High. This is calculated as follows:

$$TPMi = \frac{Xi}{li} * \left( \frac{1}{\sum_j \frac{Xj}{lj}} \right) * 10^6$$

noting $X_i$: read count of the mRNA considered; and
$l_i$: length of the mRNA considered.

For COMT, COMT TPM (COMTt) a level of 10.1 or below is considered Low, 10.1>COMTt>=15.2 Medium and COMTt>15.2 High.

For KANSL1, KANSL1 TPM (KANSL1t) a level of 16.9 or below is considered Low, 16.9>KANSL1t>=27.5 Medium and KANSL1t>27.5 High.

For SIGMAR1, SIGMAR1 TPM (SIGMAR1t) a level of 12.7 or below is considered Low, 12.7>SIGMAR1t>=19 Medium and SIGMAR1t>19 High.

Focusing on the initial panel of 243 genes, 185 RNA gene expressions and 837 DNA alterations, at the protein level, were shown to be different for at least one subject out of the total set of 21 subjects. Subjects were further characterized using an additional set of 212 non-genomic characteristics consisting of medical history, concomitant medication and other baseline characteristics. A total of 40 end points were defined as follows:

Mini-Mental State Examination ("MMSE") and Alzheimer's Disease Cooperative Study—Activities of Daily Living ("ADCS-ADL") endpoints were extracted from the data collected in ANAVEX 2-73-002.

Delta MMSE and ADCS-ADL were calculated using the difference between values collected at 6 time points and at baseline.

Similarly, a slope was calculated integrating multiple values. The slope is calculated using a linear regression across all available time-points for each individual patient. The slope calculation has the advantage of smoothing the variability across observed values of these scores.

Figure 7A:
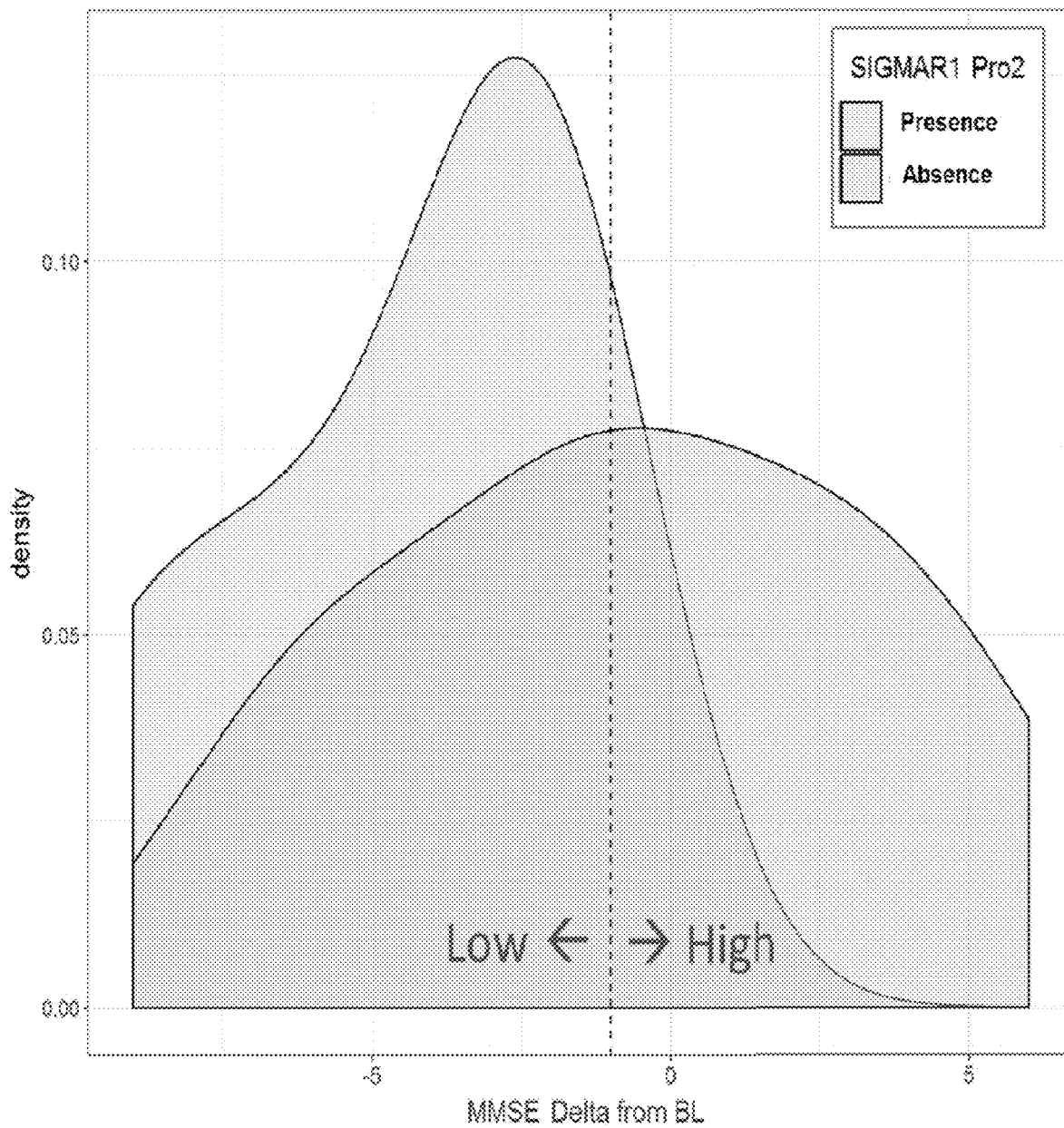
FIGS. 7A-7B. Plots showing that the presence of SIGMAR1 Pro2 mutation is associated with a poor response to a sigma-1 agonist as measured by both MMSE (FIG. 7A) and ADCS-ADL deltas (FIG. 7B).
Figure 7B:
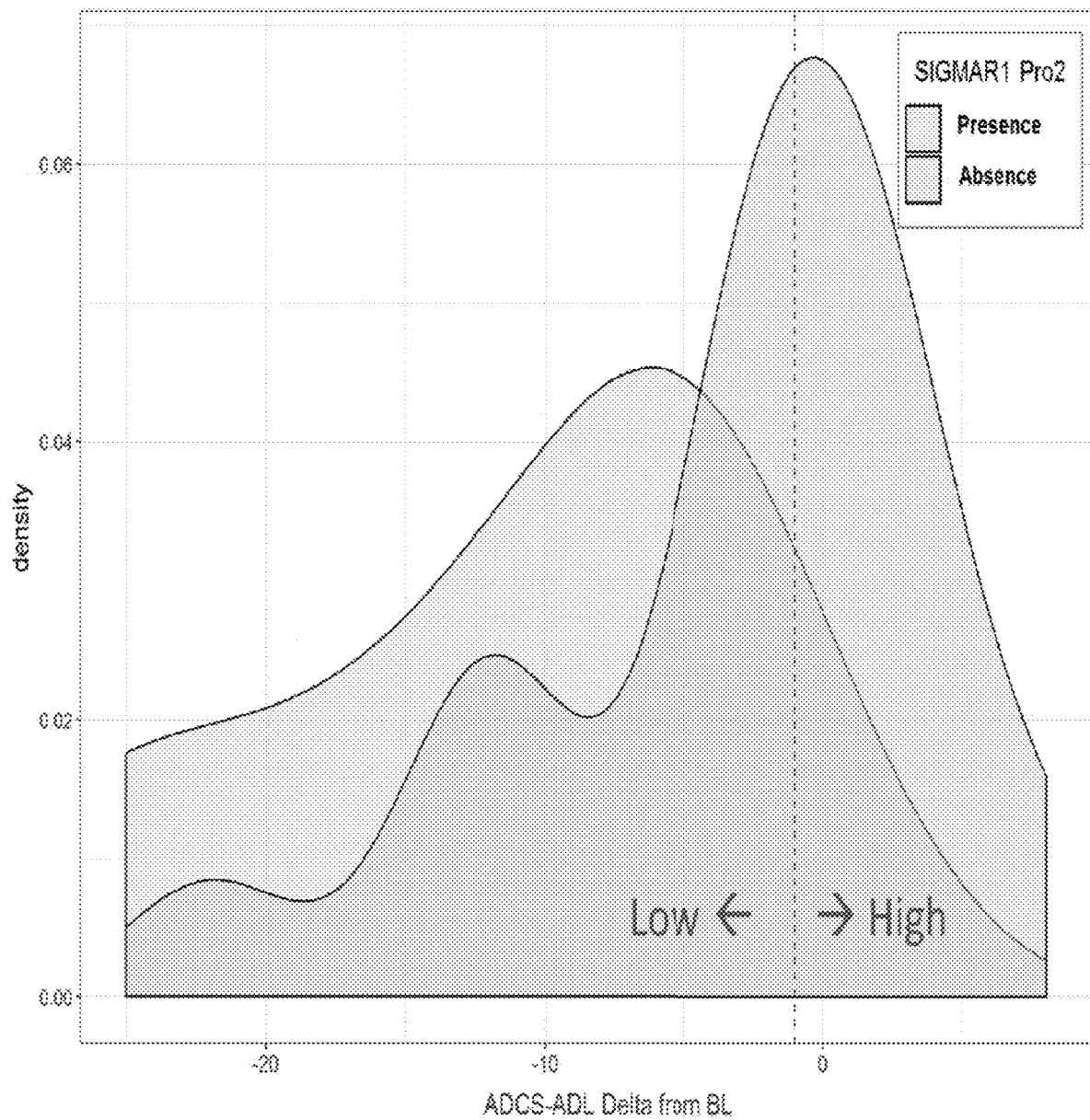

A distribution analysis was performed on the Deltas calculated for both MMSE and ADCS-ADL (FIGS. 7A and 1B). Patients were divided into categories based on third-tiles:

Delta ADCS-ADL: High ($\geq$−1) and Low ($\leq$−2);
Delta MMSE: High ($\geq$−1) and Low ($\leq$−2).

The Medium and Low bins were combined to define a new Low bin. The High bin corresponds to the highest third-tile values. Slope between baseline and week 57 for both MMSE and ADCS-ADL, respectively, was considered as a binary endpoint. Responders were defined as having a positive or null slope. Non responders were defined as displaying a negative slope.

The study contained a total of 2,481 features for each patient. KEM® v 3.6.2 (Knowledge Extraction and Management, available from Ariana Pharmaceuticals, SA) was used to analyze the available data. 3,040,276 relations were generated and analyzed. The relations were analyzed using a set metrics to evaluate their strength:

Support (n) shall mean the number of subjects for which the Association has been observed.

Lift (relative probability) shall mean the frequency of the Association divided by the frequency of the Condition. This parameter measures the enrichment provided by the Condition.

Confidence shall mean the probability of Association when the Condition is True

Cohen's d is an effect size used to indicate the standardized difference between two means. From the association rules we identified some genetic features linked with improved or worsened outcomes (delta MMSE or delta ADCSADL). For each feature we defined Group 1 by patients bearing the desirable feature (if it was linked with improved outcome), or by patients without the feature (if it was linked with worsening outcome). $M_{group1}$ and $SD_{group1}$ are respectively the mean and the standard deviation of the outcome for the group 1. $M_{group2}$ and $SD_{group2}$ are the mean and standard deviation referent values of the outcome, known in the art, for a group of patient with mild Alzheimer disease.

$$d = \frac{M_{group1} - M_{group2}}{SD_{pooled}} \quad SD_{pooled} = \sqrt{(SD^2_{group1} + SD^2_{group2})/2}$$

TABLE 16

Interpretation of effect size suggested by Cohen and Sawilowsky.

| Effect size | d | Reference |
| --- | --- | --- |
| Very small | 0.01 | Sawilowsky, 2009 |
| Small | 0.20 | Cohen, 1988 |
| Medium | 0.50 | Cohen, 1988 |
| Large | 0.80 | Cohen, 1988 |
| Very large | 1.20 | Sawilowsky, 2009 |
| Huge | 2.0 | Sawilowsky, 2009 |

P-value (Fisher's exact test, greater one-tail) evaluates the statistical significance of difference in a 2×2 contingency table.

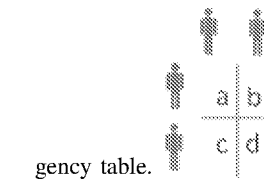

$$p = \frac{\binom{a+b}{a}\binom{c+d}{c}}{\binom{n}{a+c}}$$

Mann-Whitney-Wilcoxon (MWWilc.) is a non-parametric test of the null hypothesis that the distributions in both populations are equal. The MWWilc test ranks values of the union of two populations and compares the sum of their ranks between the two populations. We compare the distribution of the outcome between patients with the feature and patients without the feature.

MAF (Minor allele frequency): refers to the frequency at which the mutation occurs in the general population from the 1000 Genomes database.

The filtering of the relations was performed in 2 steps: a semantic filtering (1) and a numerical filtering (2). At the semantic filtering step, parameters coding for the absence of DNA mutation, medium RNA expression bins, as well as Slope MMSE and Slope ADCS-ADL were excluded. At the numerical filtering step, only relations satisfying metrics based on support (n>3), confidence (>50%), relative probability (lift>=1.2) and p-value (Fisher or Man Whitney Wilcoxon<0.05) were retained.

The filtering steps (1) and (2) leads to a subset of 509 association rules linking Base Line clinical and genomic patient characteristics and RNA expression with response at multiple time points.

Focusing on response at week 57 only, this set was further reduced to 42 associations linking DNA mutations, 27 RNA expression, and 9 involving other parameters at baseline.

The 42 association rules linking the presence of a DNA mutation with response correspond to 22 CYP proteins and 20 non CYP proteins from the gene panel defined in Table 15. The 20 non CYP relations correspond to 12 non-redundant SNPs associated with worsened response at week 57 (Table 18) and 2 associated with improved response at week 57 (Table 17).

The Table 17 data was extracted from the systematic analysis of genomic data (185 gene panel and 837 mutations). It identifies 2 SNP variants significantly linked with improved outcome as measured by delta MMSE or delta ADCS-ADL at week 57: these are HLA-DRB1_p.LysThr134LysAsp and DPYD_p.I543V (re1801159). Rules: n>3 patients, Conf.>0.5, Lift>=1.2, p-Value (Fisher Test or MWWilc.)<0.05.

TABLE 17

Presence of HLA-DRB1-P.LysThr134LysAsp or DPYD V 543 (DPYD_p.I543V) mutations were associated with improved ADCS-ADL or MMSE Delta (High) at week 57 versus baseline.

| Variants | Gene | dbsnp ID | status | timepoint | endpoint | Support |
|---|---|---|---|---|---|---|
| HLA-DRB1_p.LysThr134LysAsp | HLA-DRB1 | — | Improve | Week 57 | ADCSADL | 4 |
| DPYD_p.I543V | DPYD | rs1801159 | Improve | Week 57 | MMSE | 5 |

| Variants | Gene | Conf. | Lift | Pvalue (Fisher exact test) | Pvalue (Mann-Whitney-Wilcoxon) | d.cohen | MAF (Minor allele frequency) |
|---|---|---|---|---|---|---|---|
| HLA-DRB1_p.LysThr134LysAsp | HLA-DRB1 | 0.80 | 2.10 | 0.047 | 0.038 | 1.27 | — |
| DPYD_p.I543V | DPYD | 0.71 | 1.67 | 0.080 | 0.043 | 1.29 | 0.1849 |

TABLE 18

10 SNP variants significantly linked with worsened outcome as measured by delta MMSE or delta ADCS-ADL at week 57. Rules: n > 3 patients; Conf. > 0.5; Lift >= 1.2; p-Value (Fisher Test or MWWilc.) < 0.05

| Trial # | Variants | Gene | dbsnp ID | status |
|---|---|---|---|---|
| 1 | COMT_p.L146fs | COMT | rs113895332/rs61143203 | Worsen |
| 2 | COMT_p.L146fs | COMT | rs113895332/rs61143203 | Worsen |
| 3 | DHCR7_p.M220T | DHCR7 | rs760241 | Worsen |
| 4 | HLA-DRB1_p.A244T | HLA-DRB1 | — | Worsen |
| 5 | HLA-DRB1_p.S66T | HLA-DRB1 | rs16822820 | Worsen |
| 6 | HLA-DRB1_p.Y89S | HLA-DRB1 | rs1059586 | Worsen |
| 7 | KANSL1_p.P1010L/P304L/P946L | KANSL1 | rs115755772 | Worsen |
| 8 | KANSL1_p.1010L/P304L/P946L | KANSL1 | rs115755772 | Worsen |
| 9 | MS4A6E_p.M59T | MS4A6E | rs12798157 | Worsen |
| 10 | RIN3_p.H215R | RIN3 | rs3829947 | Worsen |
| 11 | SIGMAR1_p.Q2P | SIGMAR1 | rs1800866 | Worsen |
| 12 | SIGMAR1_p.Q2P | SIGMAR1 | rs1800866 | Worsen |

| Trial # | timepoint | endpoint | Support | Conf. | Lift | Pvalue (Fisher's exact test) | Pvalue (Mann-Whitney-Wilcoxon) | d.cohen | MAF (Minor allele frequency) |
|---|---|---|---|---|---|---|---|---|---|
| 1 | Week 57 | ADCSADL | 5 | 1.00 | 1.62 | 0.0632 | 0.0071 | 0.57 | 0.2326 |
| 2 | Week 57 | MMSE | 5 | 1.00 | 1.75 | 0.0389 | 0.1056 | 0.81 | 0.2326 |
| 3 | Week 57 | ADCSADL | 11 | 0.79 | 1.27 | 0.0408 | 0.0516 | 1.06 | 0.2436 |
| 4 | Week 57 | MMSE | 4 | 1.00 | 1.75 | 0.0827 | 0.0477 | 0.82 | — |
| 5 | Week 57 | ADCSADL | 6 | 0.86 | 1.38 | 0.1328 | 0.0361 | 0.49 | 0.1749 |
| 6 | Week 57 | MMSE | 6 | 0.86 | 1.50 | 0.0783 | 0.0392 | 0.96 | 0.0786 |
| 7 | Week 57 | ADCSADL | 12 | 0.75 | 1.21 | 0.0475 | 0.0424 | 1.10 | 0.3129 |
| 8 | Week 57 | MMSE | 11 | 0.69 | 1.20 | 00.0805 | 0.0464 | 1.70 | 0.3129 |
| 9 | Week 57 | ADCSADL | 6 | 1.00 | 1.62 | 0.0316 | 0.1010 | 0.28 | 0.2274 |
| 10 | Week 57 | ADCSADL | 9 | 0.82 | 1.32 | 0.0635 | 0.0405 | 0.86 | 0.4425 |
| 11 | Week 57 | ADCSADL | 5 | 1.00 | 1.62 | 0.0632 | 0.0346 | 0.43 | 0.2173 |
| 12 | Week 57 | MMSE | 5 | 1.00 | 1.75 | 0.0389 | 0.0814 | 0.81 | 0.2173 |

Presence of altered COMT (stop after L146), or DHCR7 T220 (DHCR7_p.M220T), or HLA-DRB1 T244 or T66 or S89 (HLA-DRB1_p.A244T or S66Y or Y89S), or KANSL1 Pro304/946/1010 (KANSL1_p.P1010L/P304L/P946L) or MS4A6E T59 (MS4A6E.p.M59T), or RIN3R 215 (RIN3_p.H215R) or SIGMAR1 Pro2 (SIGMAR1_p.Q2P) mutations are associated with ADCS-ADL or MMSE Delta Low at week 57 versus baseline.

Table 19 presents data on three mutations (SIGMAR1 Q2P; COMT_p.Li46fs, KANSL1_p.P1010L/P304L/P946L) associated with both MMSE and ADCS-ADL delta at week 57. Systematic analysis of the genomic data (185 gene panel and 837 mutations) identifies significant strong relation between SIGMAR1 Pro2 mutation and absence of response as measured both using MMSE and ADCS-ADL.

TABLE 19

| Trial # | Variants | Gene | dbsnp ID | Minor Allele Freq. |
|---|---|---|---|---|
| 1 | COMT_p.L146 FS | COMT | rs113895332/rs61143203 | 0.23 |
| 2 | DHCR7_p.M220T | DHCR7 | rs760241 | 0.24 |
| 3 | HLA-DRB1_p.A244T | HLA_DRB1 | — | |
| 4 | HLA-DRB1_p.S66T | HLA_DRB1 | rs168222820 | 0.17 |
| 5 | HLA-DRB1_p.Y89S | HLA_DRB1 | rs1059586 | 0.08 |
| 6 | KANSL1_p.P1010L/P304L/P946L | KANSL1 | rs115755772 | 0.31 |
| 7 | MS4A6E_p.M59T | MS4A6E | rs12798157 | 0.23 |
| 8 | RIN3_p.H215R | RIN3 | rs3829947 | 0.44 |
| 9 | SIGMAR1_p.Q2P | SIGMAR1 | rs1800866 | 0.22 |

| | Variants | Gene | dbsnp ID | |
|---|---|---|---|---|
| 10 | DPYD_p.I543V | DPYD | rs1801159 | 0.18 |
| 11 | HLA-DRB1_p.LysThr134LysAsp | HLA-DRB1 | | |

| | MMSE | | | ADCSADL | | | |
|---|---|---|---|---|---|---|---|
| Trial # | p Fisher | p MW Wilcox | p Fisher | p MW Wilcox | p Fisher | p MW Wilcox | Incl/Excl |
| 1 | 0.039 | 0.106 | 0.063 | 0.007 | 0.063 | 0.007 | Exclusion |
| 2 | | | 0.041 | 0.052 | 0.041 | 0.052 | Exclusion |
| 3 | 0.083 | 0.048 | | | | | Exclusion |
| 4 | | | 0.133 | 0.036 | 0.133 | 0.036 | Exclusion |
| 5 | 0.078 | 0.039 | | | | | Exclusion |
| 6 | 0.080 | 0.046 | 0.047 | 0.042 | 0.047 | 0.042 | Exclusion |
| 7 | | | 0.032 | 0.101 | 0.032 | 0.101 | Exclusion |
| 8 | | | 0.063 | 0.040 | 0.063 | 0.040 | Exclusion |
| 9 | 0.039 | 0.081 | 0.063 | 0.035 | 0.063 | 0.035 | Exclusion |

| | MMSE | | | ADCSADL | | | |
|---|---|---|---|---|---|---|---|
| | p Student | p MW Wilcox | p Student | p MW Wilcox | p Student | p MW Wilcox | Incl/Excl |
| 10 | 0.080 | 0.043 | | | | | Inclusion |
| 11 | | | 0.047 | 0.038 | 0.047 | 0.038 | Inclusion |

Table 20 is a representation of one association rule showing the presence of Pro2 mutation in SIGMA1R implies a Low delta of MMSE with details on the rule metrics, extracted from data shown in Table 18).

TABLE 20

| Pro2 mutation {PRESENT} → MMSE Delta {Low} | | | | |
|---|---|---|---|---|
| Left | Right | Support | Confidence | Lift |
| Presence of Pro2 | MMSE Delta: Low | 5 | 1 | 1.75 |

Support: 5 patients with the Pro2 mutation have a Low Delta of MMSE from Baseline.
Confidence: 100% of individuals with the Pro2 mutation have a Low Delta of MMSE from Baseline.
Lift: It is 1.75x more probable to have a Low Delta of MMSE from Baseline when patients have the Pro2 mutation.

The mutation of SIGMAR1 Gln (Glutamine) 2 changed into Pro (Proline) 2 (SIGMAR1_p.Q2P) may have structural implication for the 3D conformation of the 3D structure of the SIGMAR1 protein which in turn may alter its functions and/or interactions. The crystal structure of the SIGMAR1 shows a trimer. Each monomer displays an N terminal trans-membrane alpha helix. The N terminus of the protein is thought to face the Cytosol and is believed to interact with other ligands. The Pro2 alteration may change the conformation of the N terminus of the helix by extending it, consistent with some alteration in function.

It is possible that the Gln (Q) to Pro (P) alteration impacts the length of the side chain (extended in Gln) as well as the ability of the amino acid to form an alpha helix. Proline is considered as a "helix breaker" which, in some instances, has been attributed to unwinding of a helix.

KEM® (version 3.6.2.) relations linking presence of the SIGMAR1 Pro2 mutation with cognitive and functional endpoints are shown in Table 19. Cognitive and functional measures are both clinical endpoints in regulatory approval for therapeutics in mild and mild-to-moderate Alzheimer's disease and directed to be significantly better than placebo as primary endpoints.

Given that 57-week Phase 2a ANAVEX2-73-002 study did not include a placebo arm, the KEM® analysis measured the two endpoints consisting of cognition (MMSE) and function (ADCS-ADL) with the following two methods: Each patient's own delta of MMSE and ADCS-ADL score (delta between Week 57 and Baseline).

Importantly, since Alzheimer's disease is understood to be a progressing degenerative disease, an increase of MMSE (positive delta) and ADCS-ADL (positive delta) during 57 weeks in mild-to-moderate Alzheimer's disease is a rare positive event. Significantly, 100% of all patients which did improve MMSE (delta, n=9) and ADCS-ADL (delta, n=8) had no SIGMAR1 mutation. Further, 100% of patients bearing the SIGMAR1 Pro2 (n=5) mutation did not improve MMSE or ADCS-ADL delta. Available genetic data from all (100%) patients (n=21).

Similar results were obtained for the COMT variant COMT_p.L146fs (rs113895332/rs61143203). 100% of all patients which did exhibit improved MMSE (both delta and slope) and ADCS-ADL (both delta and slope) (n=6) did not have the COMT_p.L146fs mutation. Further, 100% of patients bearing the COMT_p.L146fs (n=5) mutation did not improve MMSE or ADCS-ADL slope. The COMT_p.L146fs mutation is also associated with low delta MMSE and ADCS-ADL. Available genetic data from all (100%) patients (n=21).

As such, establishing the presence/absence of these mutations can be useful in treatment decisions regarding SIGMAR1 agonist treatment. The absence of these mutations is a diagnostic for enhanced SIGMAR1 agonist therapy such as A2-73 therapy. Establishing the presence of either or both of these mutations is a diagnostic for using other therapeutics as first-line treatment for neurodegenerative disorders.

TABLE 21 presents the p-values results of the Mann-Whitney U test (also named Mann-Whitney-Wilcoxon test or MWWilc) between SIGMAR1 Pro2 and delta endpoints from Week 57 to baseline of MMSE and ADCS-ADL.

| Endpoint | Mann-Whitney U test P-value (on numerical values ADCS-ADL and MMSE Deltas) |
|---|---|
| ADCS-ADL Delta from BL | 0.035* |
| MMSE Delta from BL | 0.081 |

Figure 8:
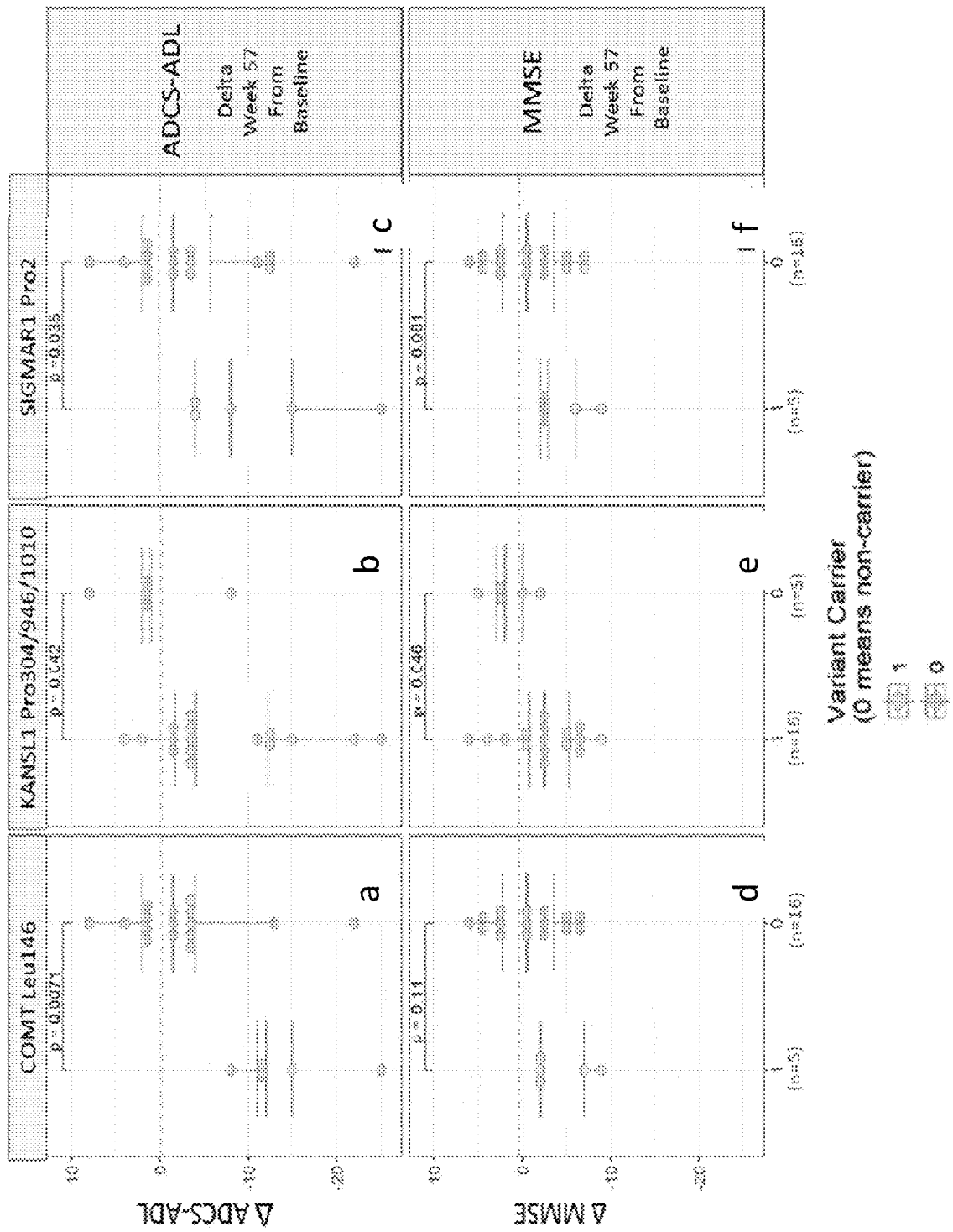
FIGS. 8A-8F.

SIGMAR1 Pro2 mutation leads to a significant difference in the numerical delta values of ADCS-ADL and MMSE delta (FIGS. 8C and 8F). The MWWilc test evaluates whether there is a significant difference in the medians of a continuous variable in two populations (i.e. the two populations here: SIGMAR1 Pro2 mutation vs SIGMAR1 Gln2 mutation). The absence of SIGMAR1 Pro2 mutation is strongly linked to high ADCS-ADL Delta from BL (improvement). Similar results were found for the COMT Leu146 mutation (FIGS. 8A and 8D) and KANSL1 Pro304/946/1010 mutation (FIGS. 8B and 8E).

As noted above, 27 RNA expressions were associated with an improved or worsened response at week 57 versus baseline. Further selecting non CYP proteins and only high levels of RNA expression (excluding low and medium expression levels), shows that high expression levels of DHCR7, GAMT, IL10, KANSL1, MTUS1, PPARG and SIGMAR1 are associated with improved ADCS-ADL or MMSE Delta at week 57 versus baseline (Table 22).

TABLE 22

| RNA Expression | status | endpoint | Support | Confidence* | Lift* | Pvalue (Fisher's exact test) | Pvalue (Mann-Whitney-Wilcoxon) | d.cohen |
|---|---|---|---|---|---|---|---|---|
| DHCR7 (High) | Improve | ADCSADL | 6 | 0.86 | 2.25 | 0.003 | 0.007 | 1.05 |
| GAMT (High) | Improve | ADCSADL | 5 | 0.71 | 1.88 | 0.041 | 0.047 | 0.54 |
| IL10 (High) | Improve | ADCSADL | 5 | 0.71 | 1.88 | 0.041 | 0.108 | 0.43 |
| KANSL1 (High) | Improve | ADCSADL | 5 | 0.71 | 1.88 | 0.041 | 0.092 | 0.45 |
| MTUS1 (High) | Improve | ADCSADL | 5 | 0.71 | 1.88 | 0.041 | 0.067 | 0.535 |
| MTUS1 (High) | Improve | MMSE | 5 | 0.71 | 1.67 | 0.080 | 0.047 | 1.33 |
| PPPARG (High) | Improve | ADCSADL | 5 | 0.71 | 1.88 | 0.041 | 0.056 | 0.48 |
| SIGMAR1 (High) | Improve | ADCSADL | 5 | 0.71 | 1.88 | 0.041 | 0.067 | 0.53 |

Focusing on the intersection between the DNA and RNA analysis and on the subset of genes that were identified through the DNA analysis and affecting outcome as measured by both MMSE and ADCS-ADL, Table 23 shows higher RNA expression of 3 gene markers (SIGMAR1; COMT; KANSL1) associated with response as measured by MMSE or ADCS-ADL.

TABLE 23

| Left | status | timepoint | endpoint | Support | Confidence* | Lift* | Pvalue (Fisher's exact test) | d.cohen |
|---|---|---|---|---|---|---|---|---|
| SIGMAR1 {High} | Improve | Week 57 | ADCSADL | 5 | 0.71 | 1.88 | 0.04 | 0.53 |
| SIGMAR1 {High} | Improve | Week 57 | MMSE | 4 | 0.57 | 1.33 | 0.32 | 1.09 |

TABLE 23-continued

| Left | status | timepoint | endpoint | Support | Confidence* | Lift* | Pvalue (Fisher's exact test) | d.cohen |
|---|---|---|---|---|---|---|---|---|
| KANSL1 {High} | Improve | Week 57 | ADCSADL | 5 | 0.71 | 1.88 | 0.04 | 0.45 |
| KANSL1{High} | Improve | Week 57 | MMSE | 4 | 0.57 | 1.33 | 0.32 | 0.79 |
| SIGMAR1 {Low} | Worsen | Week 57 | ADCSADL | 5 | 0.71 | 1.15 | 0.44 | 0.33 |
| COMT {Low} | Worsen | Week 57 | ADCSADL | 5 | 0.71 | 1.15 | 0.44 | 0.36 |

Figure 9:
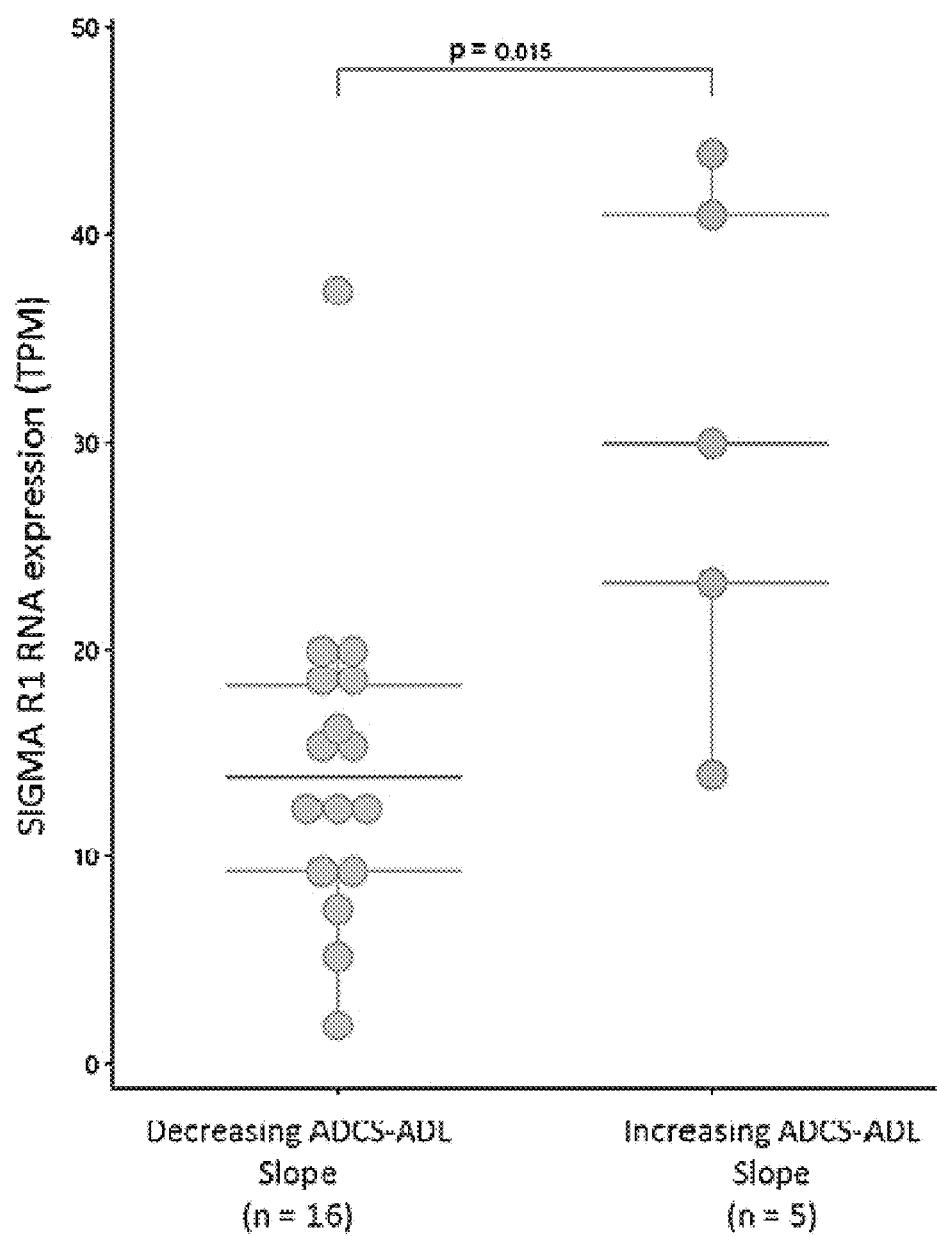
FIG. 9 is a plot showing high SIGMAR1 RNA expression is strongly linked to high ADCS-ADL slope values from BL (improvement). The analysis includes data of 100% of all patients (N=21). TPM means transcripts per kilobase million.

Notably, high RNA expression of SIGMAR1 is linked to high ANAVEX®2-73 response (improvement) as shown in Table 24 and FIG. 9.

TABLE 24

| SIGMAR1 RNA expression (Left side of rule) | Endpoint (Right side of rule) | Endpoint Outcome | Support | Confidence | Lift | Pvalue |
|---|---|---|---|---|---|---|
| Low | ADCSADL_SlopeFromBL {Decreasing} | Worsen | 7 | 1.00 | 1.31 | 0.098 |
| High | ADCSADL_DeltaFromBL {High} | Improve | 5 | 0.71 | 1.88 | 0.041 |
| High | ADCSADL_SlopeFromBL {Increasing} | Improve | 4 | 0.57 | 2.40 | 0.025 |
| High | MMSE_DeltaFromBL {High} | Improve | 4 | 0.57 | 1.33 | 0.319 |

100% of patients with low SIGMAR1 RNA expression did not improve in ADCS-ADL slope. Available genetic data from all (100%) patients. (N=21). Lift≥1.2; Conf.≥50%; Support≥3

Both DNA and RNA analysis provide convergent evidence as to the role of SIGMAR1, KANSL1 and COMT as predictors of outcome of SIGMAR1 therapy at week 57 as measured by a variation of MMSE and ADCS-ADL.

Table 25 shows a systematic analysis of the CYP genomic data (111 gene panel, from Table 15) identifies 11 SNPs significantly linked with outcome as measured by delta MMSE or delta ADCS-ADL at week 57. Correlations with improvement of MMSE and/or ADCS-ADL scores are the inclusion of variants CYP4V2, CYP271B1, CYP26C1. Correlations with an exclusion based on decline of MMSE and/or ADCS-ADL scores are the variants CYP39A1, CYP2D6, CYP2C8.

TABLE 25

| Variants | Gene | dbsnp ID | status | timepoint | endpoint | Support | Confidence* | Lift* | Pvalue Fisher | P value MW Wilc | d.cohen |
|---|---|---|---|---|---|---|---|---|---|---|---|
| CYP2C8_p.K297R/K399R | CYP2C8 | rs10509681 | Worsen | Week 57 | MMSE | 5 | 1.00 | 1.75 | 0.039 | 0.06 | 0.85 |
| CYP2C8_p.K297R/K399R | CYP2C8 | rs10509681 | Worsen | Week 57 | ADCSADL | 5 | 1.00 | 1.62 | 0.063 | 0.01 | 0.68 |
| CYP2C8_p.R139K/R37K/R53/K | CYP2C8 | rs11572080 | Worsen | Week 57 | MMSE | 5 | 1.00 | 1.75 | 0.039 | 0.06 | 0.85 |
| CYP2C8_p.R139K/R37K/R53/K | CYP2C8 | rs11572080 | Worsen | Week 57 | ADCSADL | 5 | 1.00 | 1.62 | 0.063 | 0.01 | 0.68 |
| CYP2D6_p.H34R | CYP2D6 | rs28371704 | Worsen | Week 57 | MMSE | 7 | 0.88 | 1.53 | 0.037 | 0.10 | 0.91 |
| CYP2d6_P.H94R | CYP2D6 | rs28371704 | Worsen | Week 57 | MMSE | 7 | 0.88 | 1.53 | 0.037 | 0.10 | 0.91 |
| CYP2D6_p.L31M | CYP2D6 | rs28371703 | Worsen | Week 57 | MMSE | 7 | 0.88 | 1.53 | 0.037 | 0.10 | 0.91 |
| CYP2D6_P.L91M | CYP2D6 | rs28371703 | Worsen | Week 57 | MMSE | 7 | 0.88 | 1.53 | 0.037 | 0.10 | 0.91 |
| CYP2D6_p.R314H | CYP2D6 | rs1058172 | Worsen | Week 57 | MMSE | 6 | 1.00 | 1.75 | 0.017 | 0.02 | 0.97 |
| CYP2D6_p.R365H | CYP2D6 | rs1058172 | Worsen | Week 57 | MMSE | 6 | 1.00 | 1.75 | 0.017 | 0.02 | 0.97 |
| CYP39A1_p.N324K | CYP39A1 | rs7761731 | Worsen | Week 57 | ADCSADL | 6 | 0.86 | 1.38 | 0.133 | 0.04 | 0.48 |
| CYP26C1_p.R24SQ | CYP26C1 | rs11187265 | Improve | Week 57 | ADCSADL | 5 | 0.83 | 2.19 | 0.014 | 0.09 | 0.78 |
| CYP27B1_p.I10T | CYP27B1 | rs703842 | Improve | Week 57 | MMSE | 6 | 0.60 | 1.40 | 0.142 | 0.02 | 1.37 |
| CYP4F2_p.V433M | CYP4F2 | rs2108622 | Improve | Week 57 | ADCSADL | 5 | 0.56 | 1.46 | 0.166 | 0.04 | 0.82 |
| CYP4F2_p.W12G | CYP4F2 | rs309310S | Improve | Week 57 | ADCSADL | 5 | 1.00 | 2.63 | 0.003 | 0.00 | 1.68 |
| CYP4V2_p.L22V | CYP4V2 | rs1055138 | Improve | Week 57 | MMSE | 8 | 0.57 | 1.33 | 0.078 | 0.04 | 0.96 |

Rules: n>3 patients, Conf.>0.5, Lift>=1.2, p-Value (Fisher Test or MWWilc.)<0.05

Table 26 shows RNA expression of CYP4F2, CYP26A1 and CYP2D6 associated with response as measured by MMSE or ADCS-ADL.

TABLE 26

| Gene Expression | status | timepoint | endpoint | Support | Confidence* | Lift* | Pvalue (Fisher's Test) | d.cohen |
|---|---|---|---|---|---|---|---|---|
| CYP4F2 {Low} | Improve | Week 57 | ADCSADL | 6 | 0.86 | 2.25 | 0.003 | 1.19 |
| CYP4F2 {High} | Worsen | Week 57 | ADCSADL | 7 | 1.00 | 1.62 | 0.015 | 0.27 |
| CYP26A1 {High} | Worsen | Week 57 | ADCSADL | 5 | 1.00 | 1.62 | 0.063 | 0.47 |
| CYP2D6 {Low} | Worsen | Week 57 | ADCSADL | 7 | 1.00 | 1.62 | `0.015 | 0.47 |

Rules: n>3 patients, Conf.>0.5, Lift>=1.2, p-Value (Fisher Test or MWWilc.)<0.05

Example 5. σ-1 Agonist Responder/Non-Responder Determination

Twelve subjects diagnosed with Alzheimer's disease, aged 57 to 71, are tested for the Q2P polymorphism in the SIGMAR1 gene. It is determined that two subjects carry the amino acid proline at the 2 position of the SIGMAR1 protein. It is further determined that the remaining 10 subjects carry a glutamine at that position on the receptor protein. The group with amino acid proline at the 2 position of the SIGMAR1 protein is determined unsuitable for Sigma-1 agonist therapy. The group with amino acid glutamine at the 2 position of the SIGMAR1 protein is determined suitable for Sigma-1 agonist therapy.

Example 6. σ-1 Agonist Responder Determination and Therapy

A 74 year old male presents with diagnosed Alzheimer's disease. His SIGMAR1 gene is analyzed to the extent that it is determined that he carries glutamine at the 2 position of the SIGMAR1 gene. This is the wildtype. He is treated with A2-73 daily with a 30 mg oral dose. For 6 months. His disease is seen to be stable and not progress over that period.

Example 7. σ-1 Agonist Responder Determination and Therapy

A 74 year old male presents with diagnosed Alzheimer's disease. A cheek swab is taken and a genotype assay is performed to determine the presence of the SIGMAR1 2P genotype. By such analysis it is determined that the subject carries glutamine at the 2 position of the SigmaR1 gene receptor (protein). He is treated with ANAVEX2-73 daily with a 30 mg oral dose. For 6 months. His disease is seen to be stable and not progress over that period.

Example 8. σ-1 Agonist Responder Determination and Therapy

A 66 year old female presents with diagnosed dementia. Her SIGMAR1 gene is analyzed to the extent that it is determined that she carries proline at the 2 position of the SIGMAR1 gene. She is declined treatment with a sigma-1 agonist. She is referred for other therapeutic treatment options.

Example 9. σ-1 Agonist Responder Determination and Therapy

A 60 year old female presents with diagnosed dementia. Her SIGMAR1 gene is analyzed to the extent that it is determined that she carries proline at the 2 position of the SIGMAR1 gene. She is treated with ANAVEX2-73 daily with a 80 mg oral dose in combination with 1.5 mg oral rivastigmine twice per day for 6 months. Her disease is seen to be stable and not progress over that period.

Example 10. σ-1 Agonist Responder Determination and Therapy

A 64 year old male presents with diagnosed Alzheimer's disease. His COMT gene is analyzed to the extent that it is determined that he does not carry COMT dbsnp ID rs113895332/rs61143203 mutation. He is treated with the A2-73 daily with a 30 mg oral dose. For 6 months. His disease is seen to be stable and not progress over that period.

Example 11. σ-1 Agonist Responder Determination and Therapy

A 71 year old female presents with diagnosed Alzheimer's disease. Her SIGMAR1 gene is analyzed to the extent that it is determined that she does not carry SIGMAR1 rs1800866. She is treated with A2-73 daily with a 30 mg oral dose. For 6 months. Her disease is seen to be stable and not progress over that period.

Example 12. σ-1 Agonist Responder Determination and Therapy

An 81 year old male presents with diagnosed dementia. It is determined that he carries the KANSL1_p.P1010L/P304L/P946L mutation. He is declined treatment with a sigma-1 agonist, and referred for other therapeutic treatment options.

Example 13. σ-1 Agonist Responder Determination and Therapy

An 78 year old male presents with diagnosed dementia. He carries glutamine at the 2 position of the SIGMAR1 gene. It is determined that he carries the KANSL1_p.P1010L/P304L/P946L mutation. He is treated with ANAVEX2-73 daily with a 70 mg oral dose in combination with 7 mg oral memantine daily for 6 months. His disease is seen to be stable and not progress over that period.

The invention claimed is:

1. A method of treating Alzheimer's disease, the method comprising:
   (a) identifying or having identified a subject diagnosed or suspected of having Alzheimer's disease, wherein the subject has a baseline Mini-Mental State Examination (MMSE) score of greater than or equal to 20;
   (b) obtaining or having obtained results of a test of a biological sample from the subject which determines the presence or absence of at least one polymorphism selected from Single Nucleotide Polymorphism (SNP) rs113895332 and rs61143203 in COMT gene in the subject;
   (c) determining with a confidence of 1 that the subject will not be responsive to therapy with tetrahydro-N, N-dimethyl-2,2-diphenyl-3-furanmethanamine hydrochloride (A2-73) in the presence of the at least one polymorphism in (b), and determining that the subject will be responsive to the A2-73 therapy in the absence of the at least one polymorphism in (b); and
   (d) administering A2-73 to the subject when the subject is determined to be responsive to therapy with A2-73 in step (c), thereby treating the Alzheimer's disease in the subject.

2. The method of claim 1, wherein in step (b) the at least one polymorphism comprises an additional polymorphism rs1800866 (SIGMAR1_Q2P), and the results of the test of the biological sample further determine the presence or absence of rs1800866 (SIGMAR1 Q2P) in the biological sample, wherein the presence of the at least one polymorphism and the absence of the at least one polymorphism in step (c) further comprises the additional polymorphism rs1800866 (SIGMAR1_Q2P).

3. The method of claim 1, wherein the A2-73 administered in step (d) comprises a crystalline form of A2-73, A2-73 free base, a crystalline form of A2-73 free base, a salt of A2-73 free base, or a combination thereof.

4. The method of claim 1, wherein the A2-73 administered in step (d) is a crystalline form of A2-73, A2-73 free base, a crystalline form of A2-73 free base, a salt of A2-73 free base, or a combination thereof.

5. The method of claim 1, wherein the A2-73 administered in step (d) comprises A2-73 in the amount of about 20 mg to about 60 mg when administered orally.

6. The method of claim 1, wherein the A2-73 administered in step (d) comprises A2-73 in the amount of about 1 mg to about 10 mg when administered intravenously.

7. The method of claim 1, wherein the A2-73 administered in step (d) comprises A2-73 in the amount of about 40 mg/day to about 60 mg/day.

8. The method of claim 1, wherein the A2-73 administered in step (d) provides a blood concentration of A2-73 in the subject of about 4 ng/mL.

* * * * *